United States Patent
Stoessel et al.

(10) Patent No.: US 10,381,576 B2
(45) Date of Patent: Aug. 13, 2019

(54) ELECTRONIC DEVICE HAVING AN AMINE CONTAINING LAYER PROCESSED FROM SOLUTION

(71) Applicant: Merck Patent GmbH, Darmstadt (DE)

(72) Inventors: Philipp Stoessel, Frankfurt am Main (DE); Amir Hossain Parham, Frankfurt am Main (DE); Christof Pflumm, Darmstadt (DE); Anja Jatsch, Frankfurt am Main (DE); Joachim Kaiser, Darmstadt (DE); Herwig Buchholz, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 104 days.

(21) Appl. No.: 15/534,780

(22) PCT Filed: Nov. 16, 2015

(86) PCT No.: PCT/EP2015/002286
§ 371 (c)(1),
(2) Date: Jun. 9, 2017

(87) PCT Pub. No.: WO2016/091351
PCT Pub. Date: Jun. 16, 2016

(65) Prior Publication Data
US 2018/0269406 A1    Sep. 20, 2018

(30) Foreign Application Priority Data
Dec. 9, 2014 (EP) ..................... 14004144

(51) Int. Cl.
*H01L 51/00* (2006.01)
*C07D 403/04* (2006.01)
*C09K 11/06* (2006.01)
*H01L 51/50* (2006.01)

(52) U.S. Cl.
CPC ........ *H01L 51/0072* (2013.01); *C07D 403/04* (2013.01); *C09K 11/06* (2013.01); *H01L 51/0003* (2013.01); *H01L 51/0035* (2013.01); *H01L 51/0043* (2013.01); *H01L 51/0067* (2013.01); *H01L 51/5004* (2013.01); *H01L 51/5012* (2013.01); *H01L 51/5056* (2013.01); *C09K 2211/1018* (2013.01); *H01L 51/006* (2013.01); *H01L 51/0052* (2013.01); *H01L 2251/55* (2013.01); *H01L 2251/552* (2013.01); *H01L 2251/558* (2013.01)

(58) Field of Classification Search
None
See application file for complete search history.

(56) References Cited

U.S. PATENT DOCUMENTS

| | | |
|---|---|---|
| 2016/0035992 A1 | 2/2016 | Stoessel et al. |
| 2017/0084844 A1 | 3/2017 | Parham et al. |
| 2017/0194585 A1 | 7/2017 | Yan |
| 2018/0212157 A1* | 7/2018 | Oshiyama ............ C07D 403/12 |

FOREIGN PATENT DOCUMENTS

| | | |
|---|---|---|
| CN | 103985822 A | 8/2014 |
| EP | 2733762 A1 | 5/2014 |
| EP | 3229288 A1 | 10/2017 |
| WO | WO-2014166572 A1 | 10/2014 |
| WO | WO-2015135625 A1 | 9/2015 |

OTHER PUBLICATIONS

International Search Report for PCT/EP2015/002286 dated Feb. 23, 2016.
Written Opinion of the International Searching Authority for PCT/EP2015/002286 dated Feb. 23, 2016.

* cited by examiner

*Primary Examiner* — Daniel Whalen
(74) *Attorney, Agent, or Firm* — Drinker Biddle & Reath LLP

(57) ABSTRACT

The present application relates to an organic electroluminescent device (OLED) comprising an emitting layer, where the emitting layer includes a compound having a small difference between the energies of the $S_1$ and $T_1$ states, and further comprising a layer which has been applied from solution between the emitting layer and anode and comprises an amine compound. The present application further relates to a process for producing such an OLED.

13 Claims, No Drawings

ELECTRONIC DEVICE HAVING AN AMINE CONTAINING LAYER PROCESSED FROM SOLUTION

CROSS-REFERENCE TO RELATED APPLICATIONS

This application is a national stage application (under 35 U.S.C. § 371) of PCT/EP2015/002286, filed Nov. 16, 2015, which claims benefit of European Application No. 14004144.3, filed Dec. 9, 2014, both of which are incorporated herein by reference in their entirety.

The present application relates to an organic electroluminescent device (OLED) comprising an emitting layer, where the emitting layer includes a compound having a small difference between the energies of the $S_1$ and $T_1$ states, and further comprising a layer which has been applied from solution between the emitting layer and anode and comprises an amine compound. The present application further relates to a process for producing such an OLED.

BACKGROUND OF THE INVENTION

In general, the term OLED is understood to mean an electronic device which contains at least one organic material and which emits light on application of electrical voltage. The basic structure of OLEDs is known to those skilled in the art and described, inter alia, in U.S. Pat. Nos. 4,539,507, 5,151,629, EP 0676461 and WO 98/27136.

The energies of the $S_1$ and $T_1$ states of a compound, in the context of the present application, are defined as those energies which are obtained by quantum-chemical calculations for the states of the compound in question. The $S_1$ state is the energetically lowest-lying excited singlet state, and the $T_1$ state is the energetically lowest-lying triplet state. The exact way in which the quantum-chemical calculations are conducted is described in the working examples.

An amine compound in the context of the present application is understood to mean a compound containing at least one amino group, especially a compound containing at least one arylamino group.

The prior art discloses that it is possible to obtain OLEDs having very good efficiencies with particular purely organic emitting compounds which do not phosphoresce but fluoresce. For example, H. Uoyama et al., Nature 2012, 492, 234, discloses that, with carbazolyl-cyanobenzene compounds as emitting compounds, it is possible to obtain OLEDs having external quantum efficiencies that are similarly good or better than those obtainable with phosphorescent emitters. Such emitting compounds are characterized in that they have a small difference between the energies of the $S_1$ and $T_1$ states. The mechanism of emission on which they are based is referred to as thermally activated delayed fluorescence (TADF). Mehes et al., Angew. Chem. Int. Ed. 2012, 51, 11311, likewise describes the use of compounds that exhibit TADF in OLEDs.

Said documents relate exclusively to OLEDs in which the organic functional layers, especially those layers disposed between the anode and emitting layer, have been applied by gas phase deposition. However, there is great interest in applying TADF emitter technology also to OLEDs having layers applied from solution. There is a particular interest in at least the layers between the anode and emitting layer being applied from solution.

However, the results shown in the prior art are not completely satisfactory. It is especially desirable for the OLEDs based on the TADF emission mechanism to have a high lifetime and very good performance data, especially low operating voltage and high quantum efficiency, and there is a need for improvement in this regard. Moreover, it is of great significance that OLEDs based on the TADF emission mechanism have only a minor proportion of rejects, meaning that only a small proportion of the OLEDs produced, preferably a negligibly small proportion, does not work. This is of particular significance when thin layers of thickness less than 30 nm are applied.

BRIEF SUMMARY OF THE INVENTION

In this connection, it has now been found that, surprisingly, OLEDs which contain a TADF emitter in the emitting layer and which have a layer which has been applied from solution between the anode and emitting layer and contains an amine compound exhibit excellent performance data. More particularly, the performance data are improved over otherwise identical OLEDs that do not have a layer containing an amino compound between the anode and emitting layer. Moreover, it has been found that, surprisingly, the above-described OLEDs have a small proportion of rejects in production, meaning that only a negligibly small proportion thereof does not work. In contrast, in the case of otherwise identical OLEDs where the layer disposed between the anode and emitting layer has not been applied from solution, the proportion of rejects is much higher.

DETAILED DESCRIPTION OF THE INVENTION

The present invention thus provides an organic electroluminescent device comprising
  anode,
  cathode,
  an emitting layer comprising an emitting compound having a magnitude of the difference between the energies of its $S_1$ and $T_1$ states of not more than 0.15 eV, and
  a layer which is disposed between the anode and emitting layer and comprises an amine compound and has been applied from solution, where the energies of the $S_1$ and $T_1$ states of the emitting compound are determined as specified in the working examples.

The result of application of the layer containing an amine compound from solution is that a differently shaped surface of the layer is obtained from when the layer containing the amine compound has been applied from the gas phase. More particularly, the surface of such a layer applied from solution is planarized, meaning that it has a smooth, flat surface. If the layer containing an amine compound, in contrast, is applied from the gas phase, unevenness in the surface of the layer beneath likewise recurs in the surface of the newly applied layer.

A further difference lies in the order of the molecules present in the layer. In the case of a layer applied from solution, the molecules are unordered in the layer. Homogeneous orientation of the compounds occurs only to an extremely small degree. The layer is in a glassy and amorphous state. In contrast, in the case of a layer applied from the gas phase, there is a certain order of the molecules in the layer. The degree of order is especially much higher than in the case of a layer applied from solution. This is described in the literature, for example by X. Xing et al., J. Phys. Chem. C, 2013, 117, 25405-25408.

Preferably, the emitting compound is an organic compound. An organic compound in the context of the present invention is understood to mean a carbonaceous compound that does not contain any metals. Preferably, an organic compound according to the present invention is formed from the elements C, H, D, B, Si, N, P, O, S, F, Cl, Br and I.

Further preferably, the emitting compound is a luminescent compound. A luminescent compound in the context of the present application is understood to mean a compound capable of emitting light at room temperature under optical excitation in an environment as exists in the organic electroluminescent device. The emitting compound preferably has a luminescence quantum efficiency of at least 40%, more preferably of at least 50%, even more preferably of at least 60% and especially preferably of at least 70%. The luminescence quantum efficiency is determined in a layer like that which is to be used in the organic electroluminescent device. The way in which the determination of the luminescence quantum yield is conducted in the context of the present invention is described in the examples section (Photoluminescence quantum efficiency section).

It is additionally preferable when the emitting compound has a short decay time. The decay time is preferably ≤50 μs. The way in which the determination of the decay time is conducted in the context of the present invention is described in the examples section.

According to the invention, the magnitude of the difference between the energies of the $S_1$ and $T_1$ states of the emitting compound is not more than 0.15 eV. Preferably, the magnitude of the difference is ≤0.10 eV, more preferably ≤0.08 eV, most preferably ≤0.05 eV.

The emitting compound is preferably an aromatic compound having both at least one donor substituent and at least one acceptor substituent, with only minor spatial overlap between the LUMO and HOMO of the compound. What is understood by donor and acceptor substituents is known in principle to those skilled in the art. Suitable donor substituents are especially diaryl- or diheteroarylamino groups and carbazole groups or carbazole derivatives, each preferably bonded to an aromatic compound via N. These groups may also have further substitution. Suitable acceptor substituents are especially cyano groups and electron-deficient heteroaryl groups which may also have further substitution.

Examples of suitable emitting compounds in the context of the present application are the following structures:

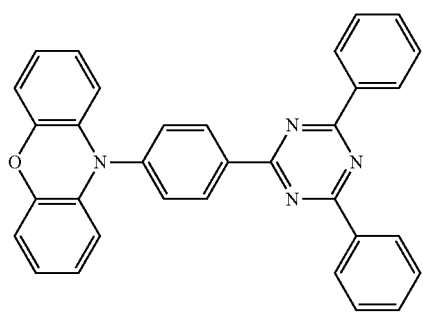

T-1

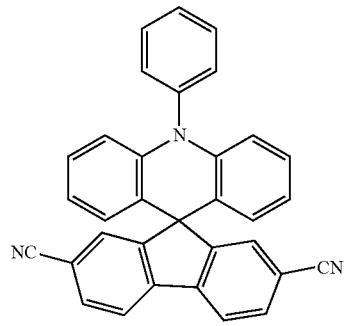

T-2

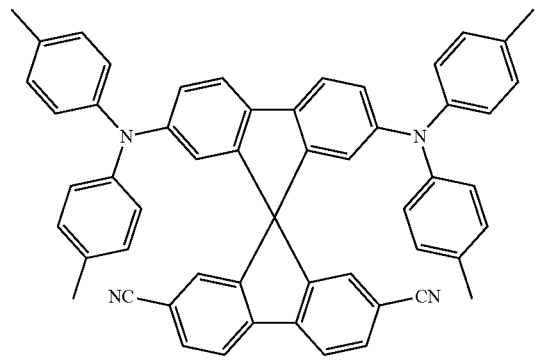

T-3

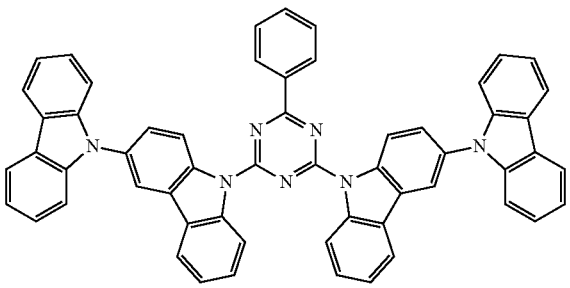

T-4

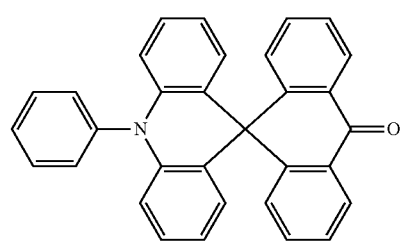

T-5

T-6
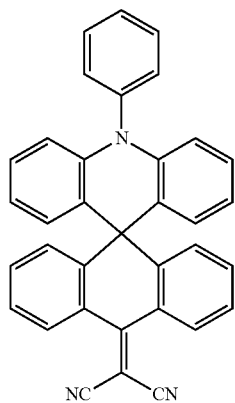
T-7
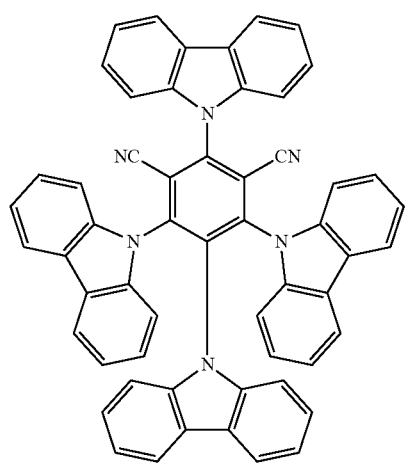
T-8
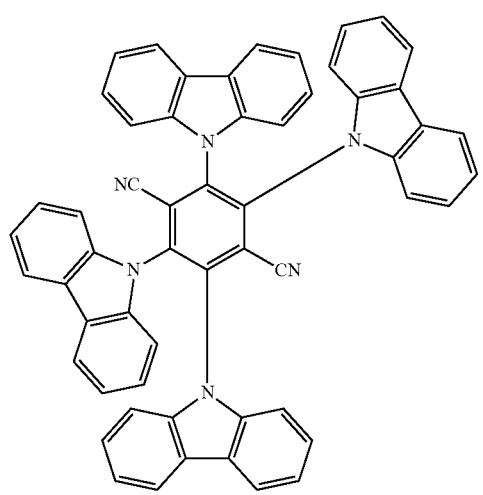
T-9
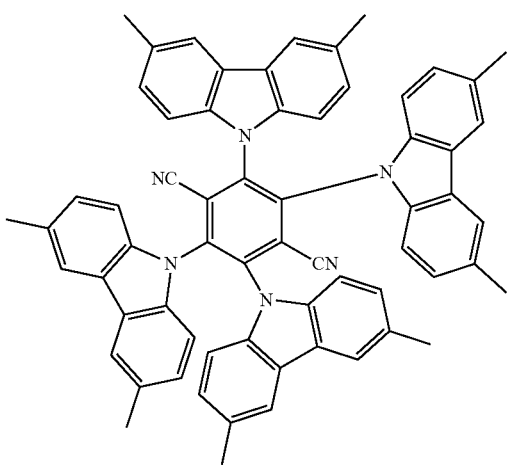
T-10
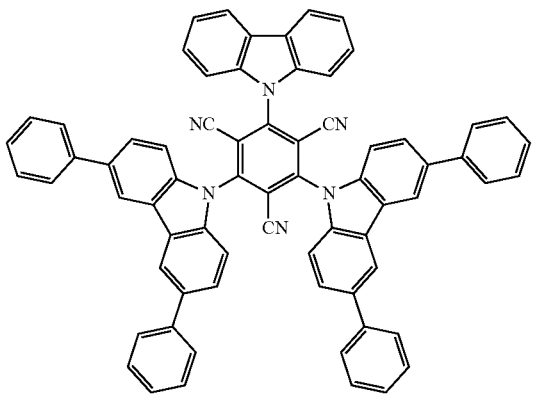
T-11
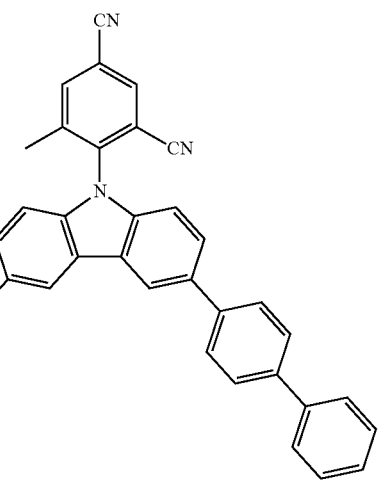

T-12
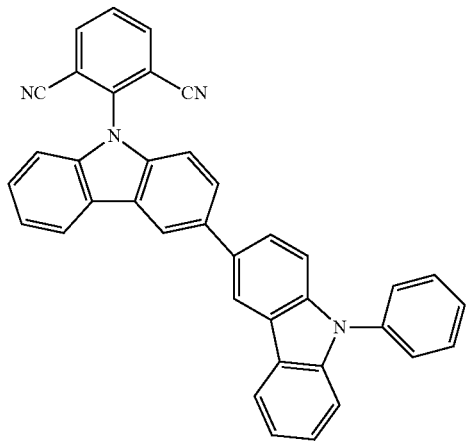
T-13
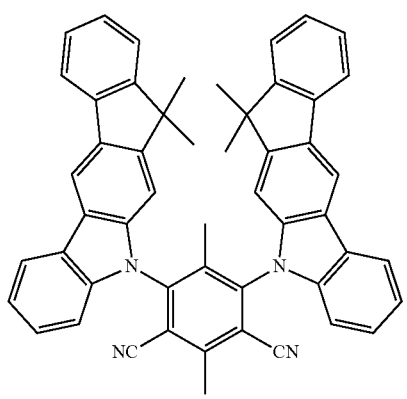
T-14
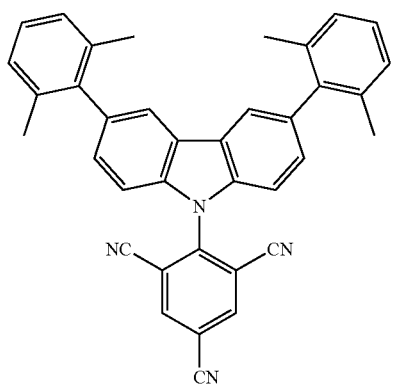
T-15
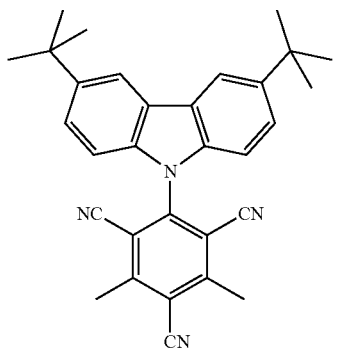
T-16
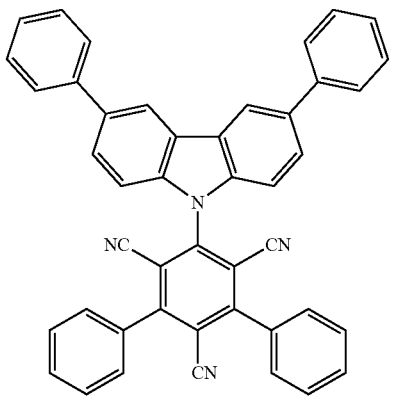
T-17
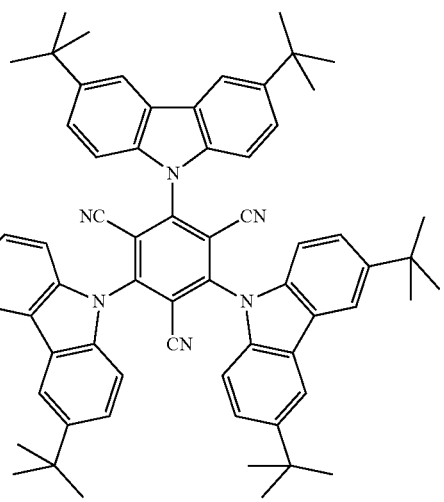
T-18
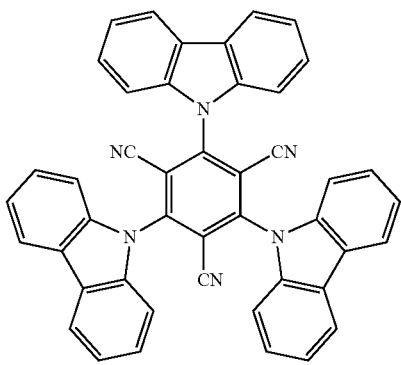

T-19

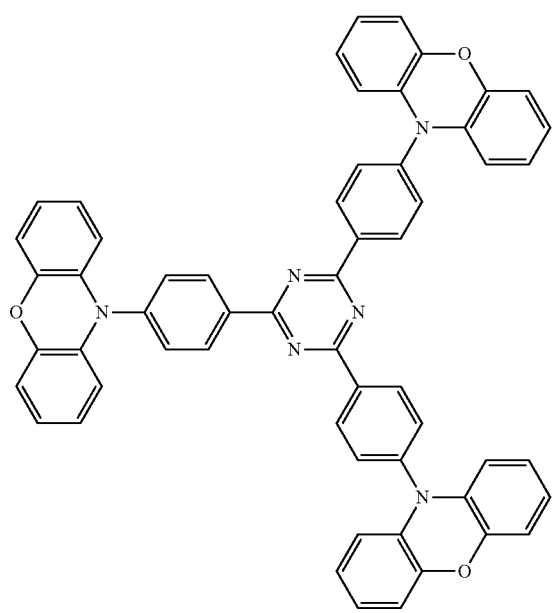

T-20

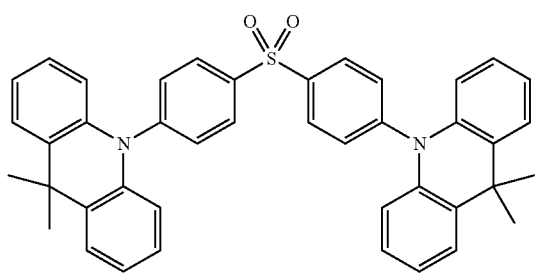

T-21

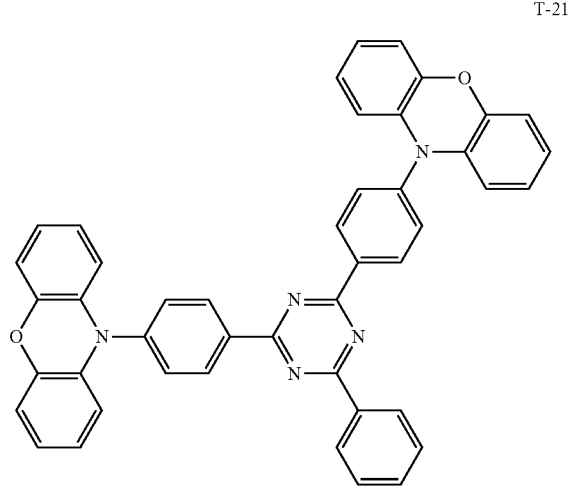

T-22

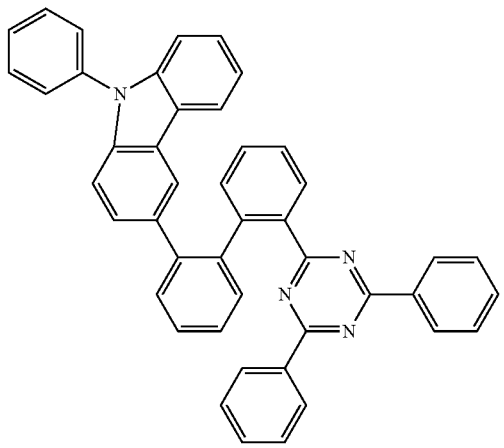

Additionally known in the prior art are a multitude of emitting compounds which fulfil the abovementioned condition for the gap between the $S_1$ and $T_1$ energy levels and from which the person skilled in the art is able to select in order to obtain suitable emitting compounds for the OLED described in the present application, for example, Tanaka et al., Chemistry of Materials 25(18), 3766 (2013), Zhang et al., Nature Photonics Volume 8, p. 326-332, Serevicius et al., Physical Chemistry Chemical Physics 15(38), 15850 (2013), Youn Lee et al., Applied Physics Letters 101(9), 093306 (2012), Nasu et al., ChemComm, 49, 10385 (2013), WO 2013/154064, WO 2013/161437, WO 2013/081088 and WO 2013/011954.

The emitting layer preferably comprises, as well as the emitting compound, one or more matrix compounds, more preferably exactly one or two matrix compounds, most preferably exactly one matrix compound. Preferably, the one or more matrix compounds make no contribution to the emission of the device in operation.

Preferably, the emitting compound is present in the emitting layer in a proportion of 1% to 25% by volume, more preferably of 2% to 20% by volume, even more preferably of 4% to 15% by volume and most preferably of 5% to 12% by volume. Preferably, in this case, apart from the emitting compound, the only further compounds present in the emitting layer are one or more matrix compounds, and so these make up the residual proportion.

It is preferable when the following applies to LUMO(E), i.e. the LUMO energy level of the emitting compound, and HOMO(matrix), i.e. the HOMO energy level of the matrix compound:

$$\text{LUMO}(E) - \text{HOMO}(\text{matrix}) > S_1(E) - 0.4 \text{ eV};$$

more preferably:

$$\text{LUMO}(E) - \text{HOMO}(\text{matrix}) > S_1(E) - 0.3 \text{ eV};$$

and even more preferably:

$$\text{LUMO}(E) - \text{HOMO}(\text{matrix}) > S_1(E) - 0.2 \text{ eV}.$$

In this case, $S_1(E)$ is the energy of the first excited singlet state of the emitting compound.

It is additionally preferable that the energy of the $T_1$ state of the matrix compound of the emitting layer, referred to hereinafter as $T_1(\text{matrix})$, is not more than 0.1 eV lower than the energy of the $T_1$ state of the emitting compound, referred to hereinafter as $T_1(E)$. More preferably, $T_1(\text{matrix}) \geq T_1(E)$.

Even more preferably: $T_1$(matrix)−$T_1$(E)≥0.1 eV, most preferably $T_1$(matrix)−$T_1$(E)≥0.2 eV.

Examples of suitable matrix compounds in the emitting layer are ketones, phosphine oxides, sulphoxides and sulphones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix compounds, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, zinc complexes, for example according to EP 652273 or WO 2009/062578, or bridged carbazole derivatives, for example according to US 2009/0136779, WO 2010/050778, WO 2011/042107 or WO 2011/088877.

Preference is given to electron-transporting organic compounds for use as matrix compounds in the emitting layer. Particular preference is given to electron-transporting organic compounds having a LUMO energy level of not more than −2.50 eV, more preferably not more than −2.60 eV, even more preferably not more than −2.65 eV and most preferably not more than −2.70 eV.

Particularly preferred matrix compounds in the emitting layer are selected from the substance classes of the triazines, the pyrimidines, the lactams, the metal complexes, especially the Be, Zn and Al complexes, the aromatic ketones, the aromatic phosphine oxides, the azaphospholes, the azaboroles substituted by at least one electron-conducting substituent, the quinoxalines, the quinolines and the isoquinolines.

Preferably, the matrix compound of the emitting layer is not the following compound:

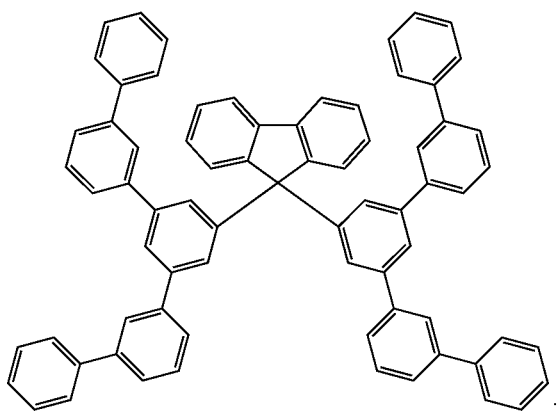 [SMILES: c1ccc(-c2cccc(-c3cc(-c4cccc(-c5ccccc5)c4)cc(C4(c5cc(-c6cccc(-c7ccccc7)c6)cc(-c6cccc(-c7ccccc7)c6)c5)c5ccccc5-c5ccccc54)c3)c2)cc1]

More preferably, the matrix compound of the emitting layer is not a wide-bandgap compound, which is understood to mean compounds having a difference between the HOMO energy and LUMO energy of at least 3.5 eV. HOMO and LUMO energies are determined as specified in the working examples.

In addition, the matrix compound of the emitting layer is preferably not the following compound:

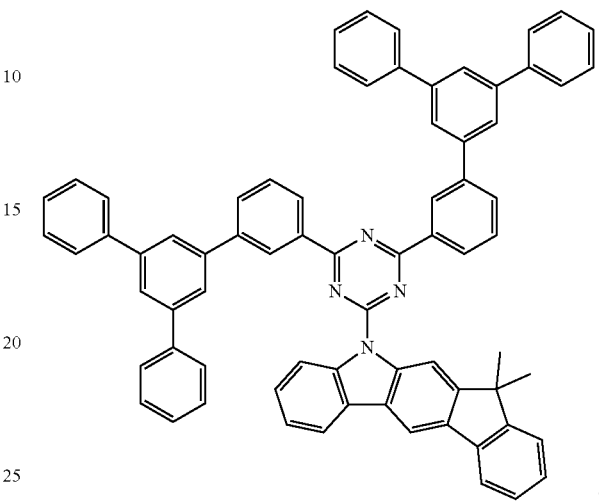

More preferably, the matrix compound of the emitting layer is not an indenocarbazole compound.

The layer which is disposed between the anode and emitting layer, has been applied from solution and comprises an amine compound preferably does not comprise any further compounds. If further compounds are present, they are preferably chosen from further amine compounds and from p-dopants.

p-dopants used according to the present invention are preferably those organic electron acceptor compounds capable of oxidizing one or more of the other compounds in the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600, WO 2012/095143 and DE 102012209523.

Particularly preferred p-dopants are quinodimethane compounds, azaindenofluorenediones, azaphenalenes, azatriphenylenes, $I_2$, metal halides, preferably transition metal halides, metal oxides, preferably metal oxides containing at least one transition metal or a metal of main group 3, and transition metal complexes, preferably complexes of Cu, Co, Ni, Pd and Pt with ligands containing at least one oxygen atom as bonding site. Preference is further given to transition metal oxides as dopants, preferably oxides of rhenium, molybdenum and tungsten, more preferably $Re_2O_7$, $MoO_3$, $WO_3$ and $ReO_3$. Preference is further given to bismuth complexes having electron-deficient carboxylate ligands, preferably fluorinated carboxylate ligands.

Preferably, the layer which is disposed between the anode and emitting layer and has been applied from solution and comprises an amine compound has a thickness of more than 10 nm, more preferably of more than 20 nm, even more preferably of more than 30 nm. This achieves a higher reliability of the OLEDs; more particularly, the failure frequency is reduced.

The amine compound, according to a preferred embodiment of the invention, is a small organic molecule, more preferably a low molecular weight compound. Preferably, its molecular weight is less than or equal to 1500 g/mol, more preferably less than or equal to 1000 g/mol, most preferably less than or equal to 700 g/mol.

Among these, preference is given to triarylamine compounds. Triarylamine compounds are understood to mean compounds in which three aryl or heteroaryl groups are bonded to a nitrogen atom. Preference is given to aryl groups. Very particularly preferred amine compounds are monotriarylamine compounds. This is understood to mean compounds comprising not more than one chemical group which is a triarylamine as defined above.

An aryl group in the context of this invention contains 6 to 60 aromatic ring atoms; a heteroaryl group in the context of this invention contains 5 to 60 aromatic ring atoms, at least one of which is a heteroatom. The heteroatoms are preferably selected from N, O and S. This is the fundamental definition.

An aryl group or heteroaryl group is understood here to mean either a simple aromatic cycle, i.e. benzene, or a simple heteroaromatic cycle, for example pyridine, pyrimidine or thiophene, or a fused (annelated) aromatic or heteroaromatic polycycle, for example naphthalene, phenanthrene, quinoline or carbazole. A fused (annelated) aromatic or heteroaromatic polycycle, in the context of the present application, consists of two or more simple aromatic or heteroaromatic cycles fused to one another.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preferably, the low molecular weight amine compound is selected from the formulae (M-1) to (M-6)

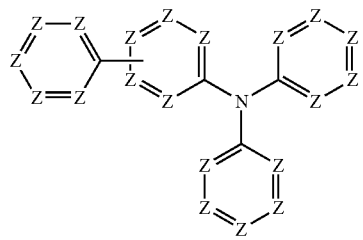

Formula (M-1)

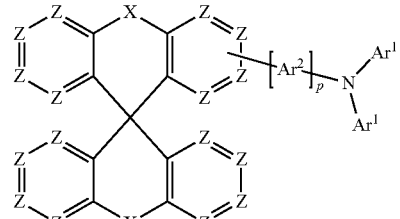

Formula (M-2)

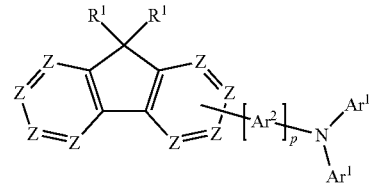

Formula (M-3)

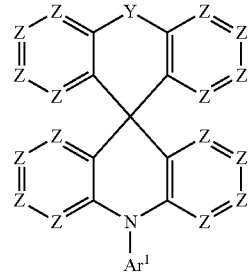

Formula (M-4)

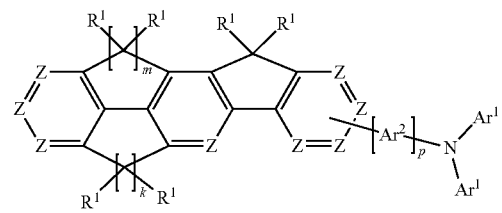

Formula (M-5)

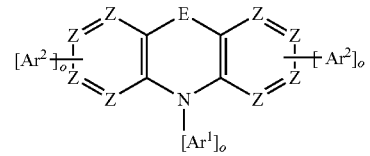

Formula (M-6)

where:
Z is the same or different at each instance and is N or $CR^1$, where Z is C when a substituent is attached;
X is the same or different at each instance and is a single bond, O, S, $BR^1$, $C(R^1)_2$, $Si(R^1)_2$, $NR^1$, $PR^1$, $C(R^1)_2$—$C(R^1)_2$, or $CR^1$=$CR^1$;
Y is a single bond, O, S, $BR^1$, $C(R^1)_2$, $Si(R^1)_2$, $NR^1$, $PR^1$, $C(R^1)_2$—$C(R^1)_2$, or $CR^1$=$CR^1$;
E is O, S, $BR^1$, $C(R^1)_2$, $Si(R^1)_2$, $NR^1$, $PR^1$, $C(R^1)_2$—$C(R^1)_2$, or $CR^1$=$CR^1$;
$Ar^1$ is the same or different at each instance and is an aromatic or heteroaromatic ring system which has 5 to 30 aromatic ring atoms and may be substituted by one or more $R^1$ radicals;
$Ar^2$ is an aromatic or heteroaromatic ring system which has 6 to 18 aromatic ring atoms and may be substituted by one or more $R^1$ radicals;
$R^1$ is the same or different at each instance and is selected from H, D, F, C(=O)$R^2$, CN, Si($R^2$)$_3$, N($R^2$)$_2$, P(=O)($R^2$)$_2$, O$R^2$, S(=O)$R^2$, S(=O)$_2R^2$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more radicals may be joined to one another and may form a ring; where the alkyl, alkoxy, alkenyl and alkynyl groups mentioned and the aromatic ring systems and heteroaromatic ring systems mentioned may each be substituted by one or more $R^2$ radicals; and where one or more $CH_2$ groups in the alkyl, alkoxy, alkenyl and alkynyl groups mentioned may be replaced by $-R^2C=CR^2-$, $-C\equiv C-$, $Si(R^2)_2$, $C=O$, $C=NR^2$, $-C(=O)O-$, $-C(=O)NR^2-$, $NR^2$, $P(=O)(R^2)$, $-O-$, $-S-$, $SO$ or $SO_2$;

$R^2$ is the same or different at each instance and is selected from H, D, F, CN, alkyl groups having 1 to 20 carbon atoms, aromatic ring systems having 6 to 40 aromatic ring atoms and heteroaromatic ring systems having 5 to 40 aromatic ring atoms; where two or more $R^2$ radicals may be joined to one another and may form a ring; and where the alkyl groups, aromatic ring systems and heteroaromatic ring systems mentioned may be substituted by F or CN;

o is the same or different at each instance and is 0 or 1, where the sum total of all the indices o is at least 1;

p is 0 or 1;

k, m are the same or different and are each 0 or 1, where the sum total of all the indices k and m is 1 or 2.

For the abovementioned formulae (M-1) to (M-6), it is preferably the case that not more than three Z groups in one ring are N. It is generally preferable that Z is $CR^1$.

The X group is preferably the same or different at each instance and is selected from a single bond, $C(R^1)_2$, O and S, and is more preferably a single bond.

The Y group is preferably selected from O and $C(R^1)_2$, and is more preferably O.

The E group is preferably selected from $C(R^1)_2$, O and S, and is more preferably $C(R^1)_2$.

The $Ar^1$ group in the abovementioned formulae is preferably the same or different at each instance and is selected from aromatic or heteroaromatic ring systems which have 6 to 30 aromatic ring atoms and may be substituted by one or more $R^1$ radicals. More preferably, $Ar^1$ in the abovementioned formulae is the same or different at each instance and is selected from aryl or heteroaryl groups which have 6 to 18 aromatic ring atoms and may be substituted by one or more $R^1$ radicals.

Explicit examples of the low molecular weight amine compounds in the context of the present application are as follows:

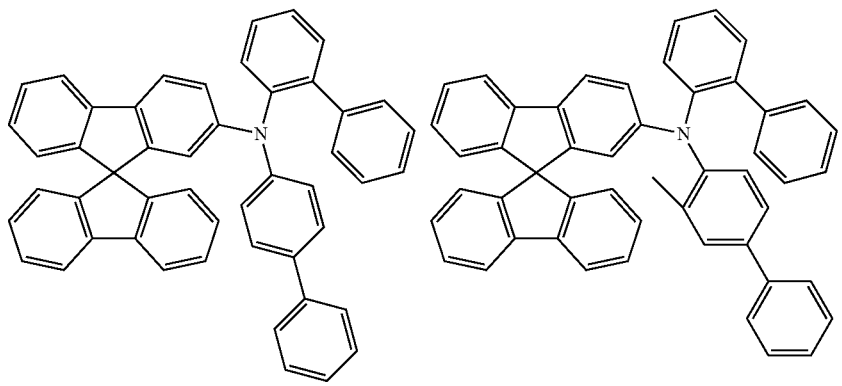

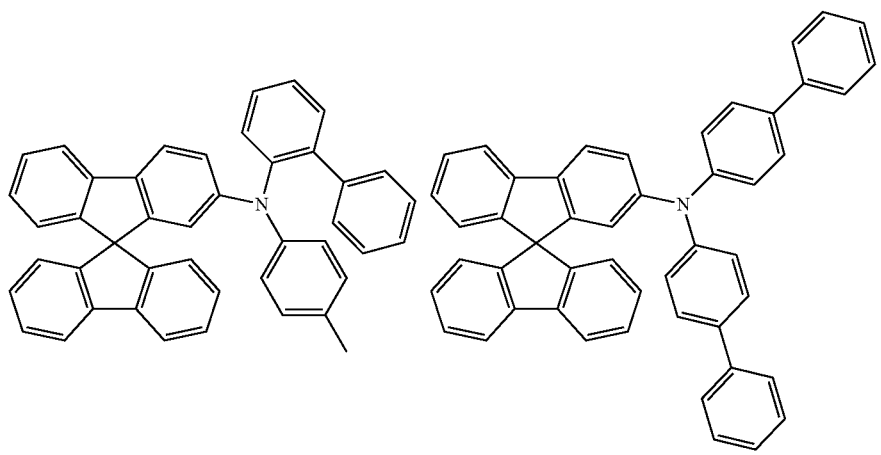

-continued
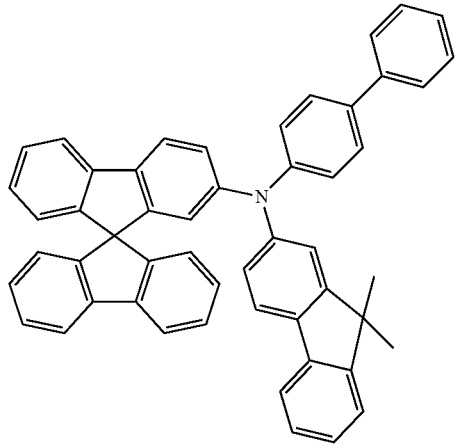
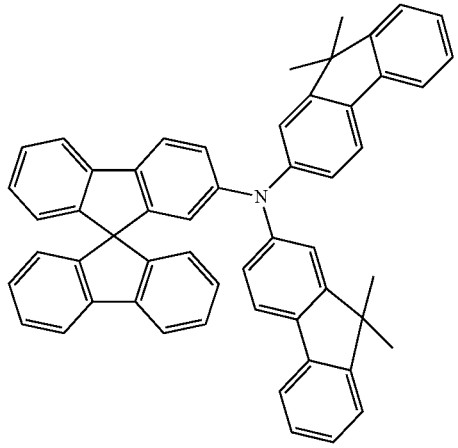
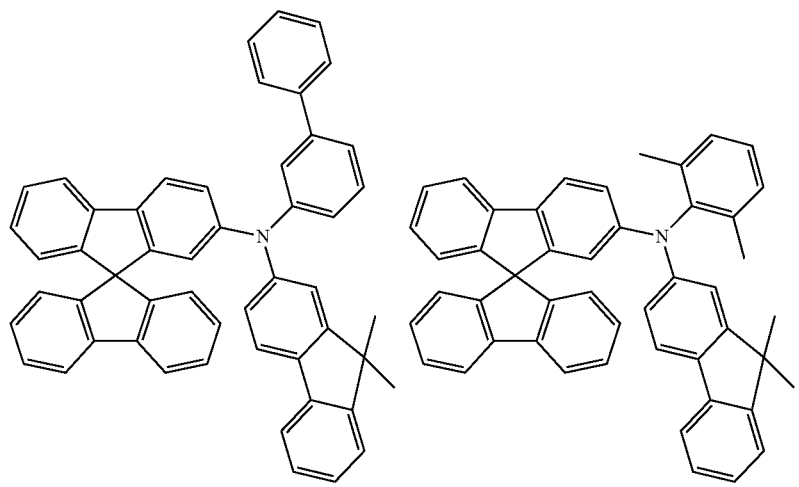
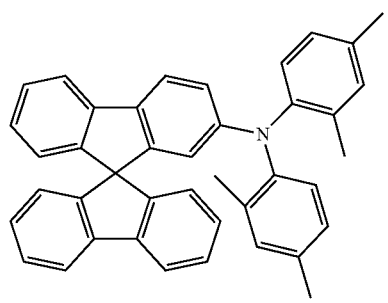
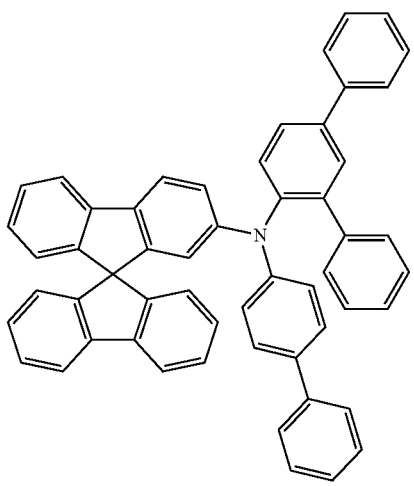

-continued
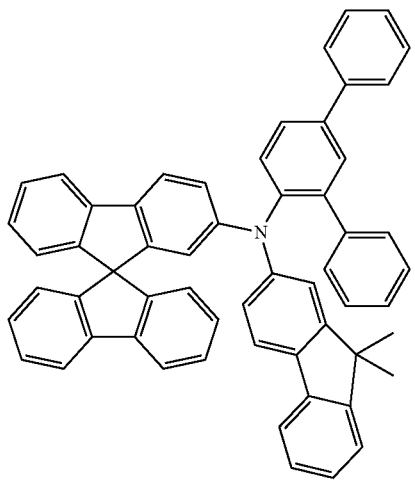
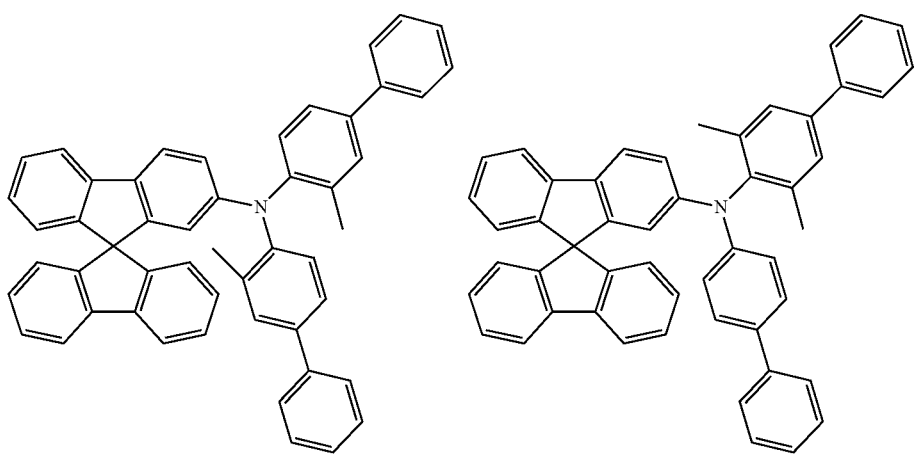 [SMILES: Cc1cc(-c2ccccc2)ccc1N(c1ccc2c(c1)C1(c3ccccc3-c3ccccc31)c1ccccc1-2)c1ccc(-c2ccccc2)cc1C ; Cc1cc(-c2ccccc2)cc(C)c1N(c1ccc(-c2ccccc2)cc1)c1ccc2c(c1)C1(c3ccccc3-c3ccccc31)c1ccccc1-2]
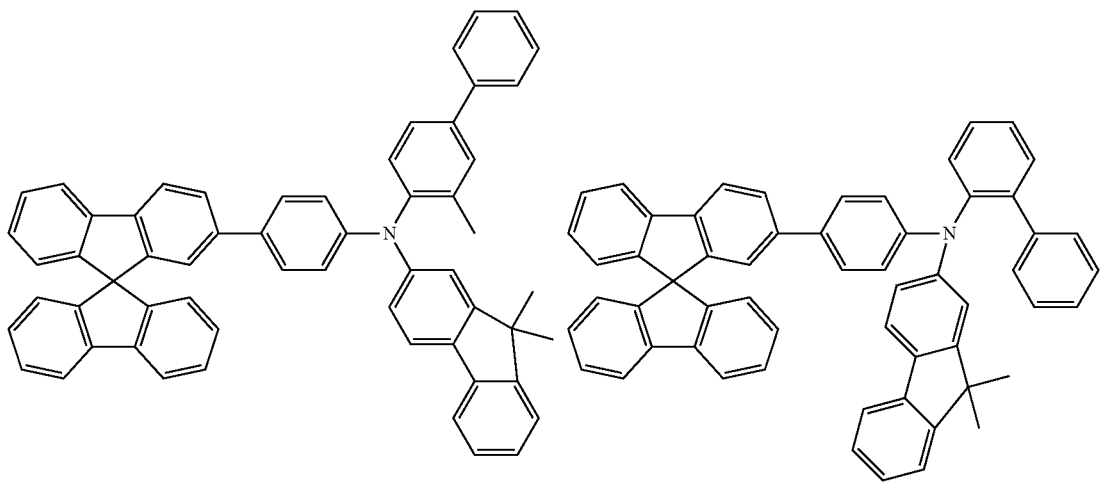

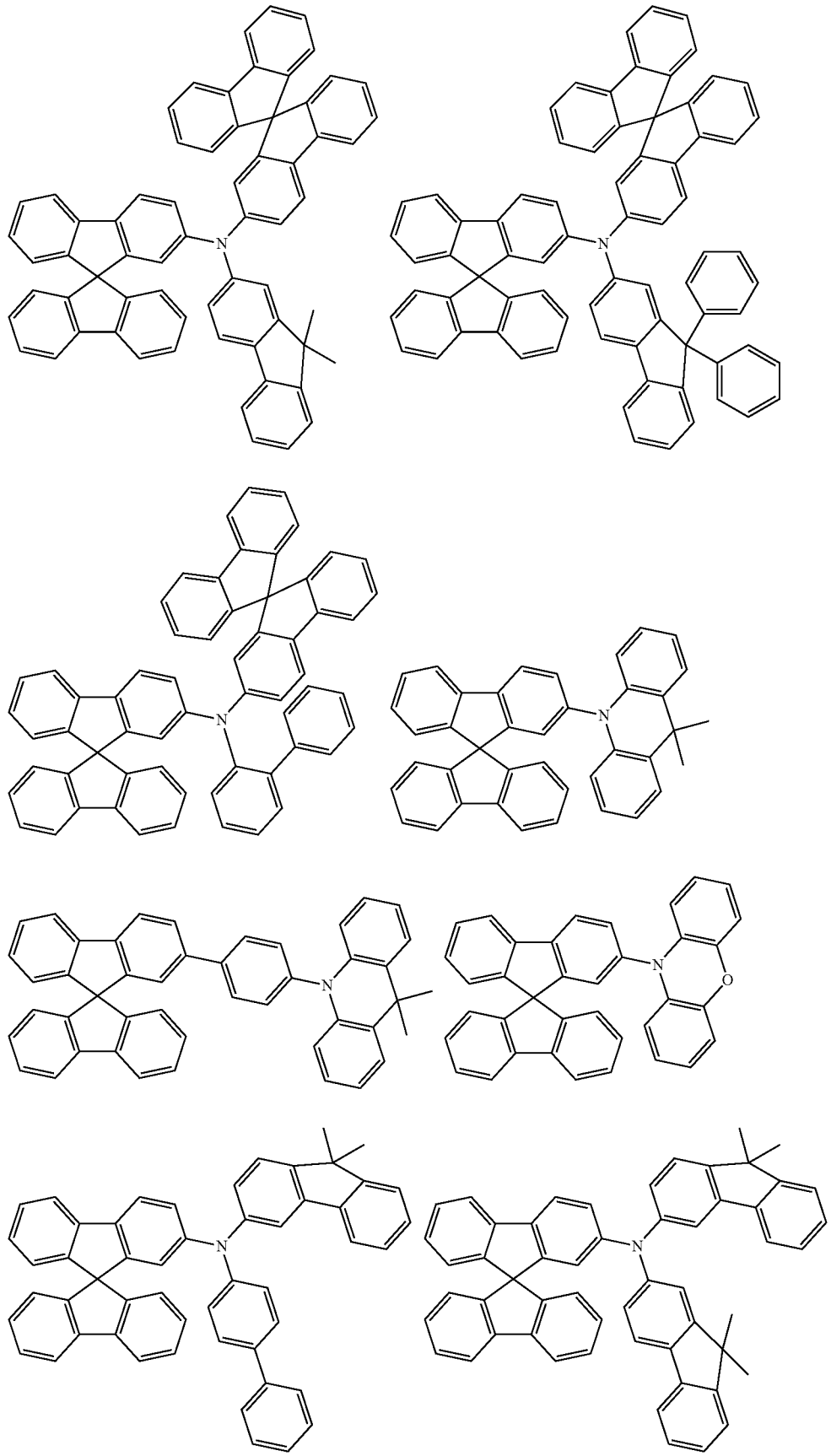

-continued
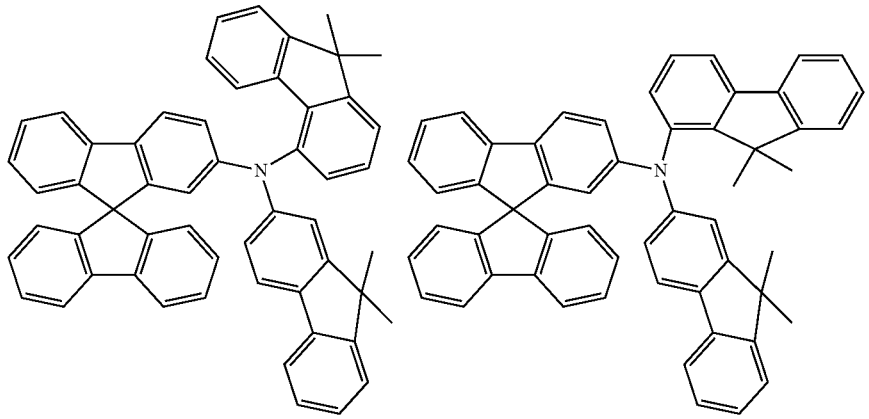
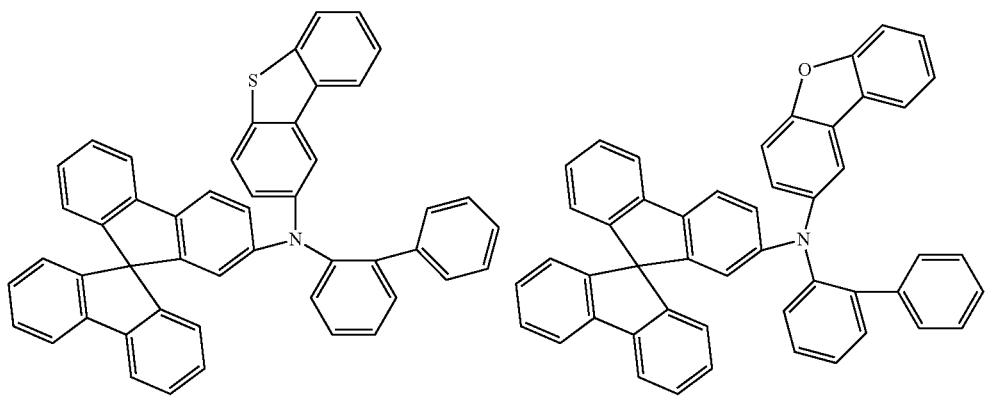
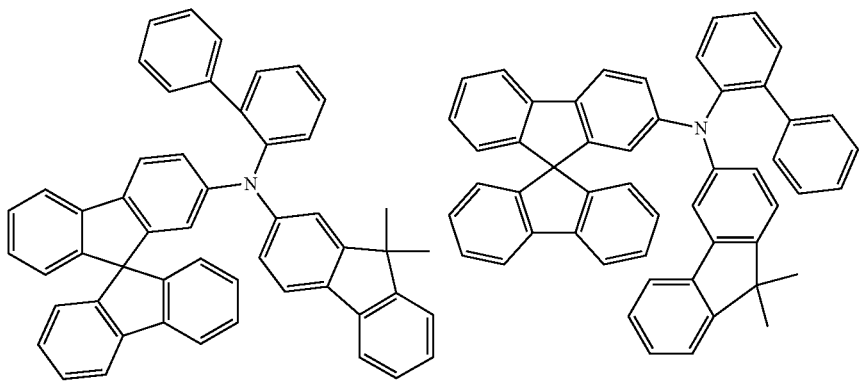
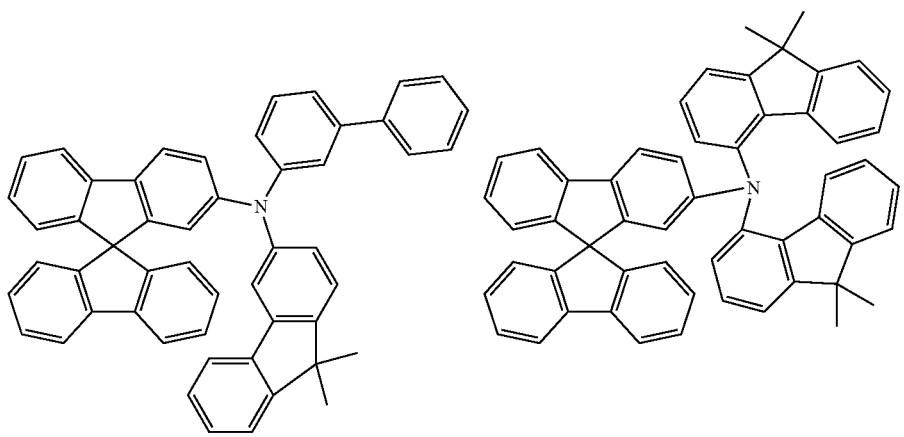

-continued
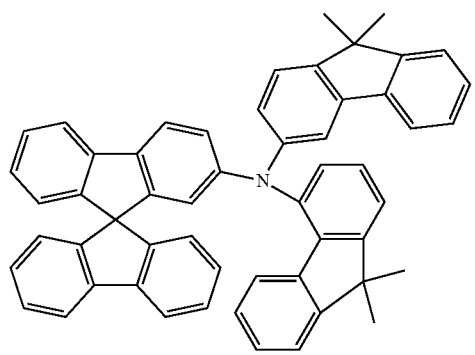
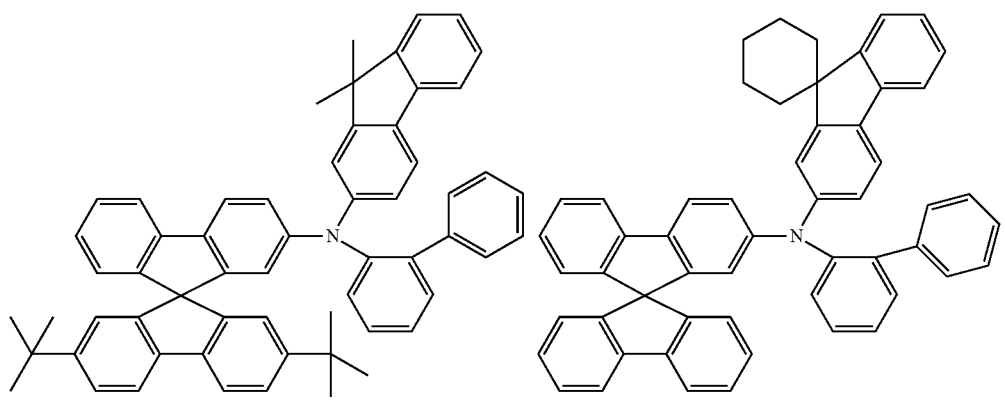
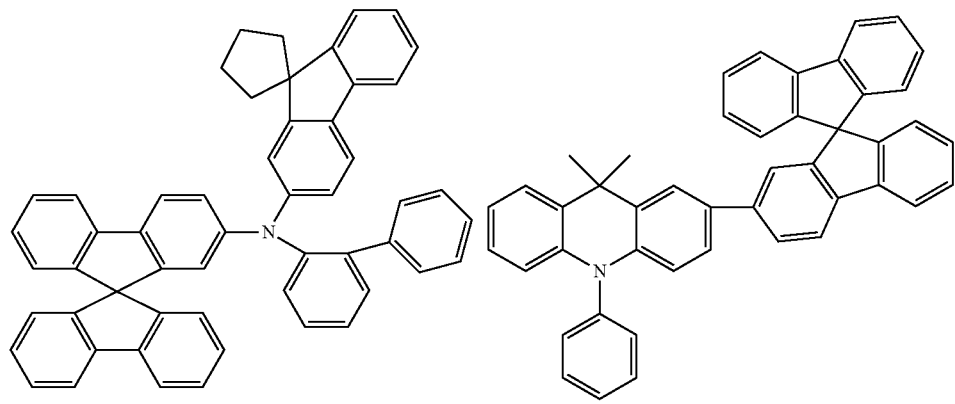

-continued
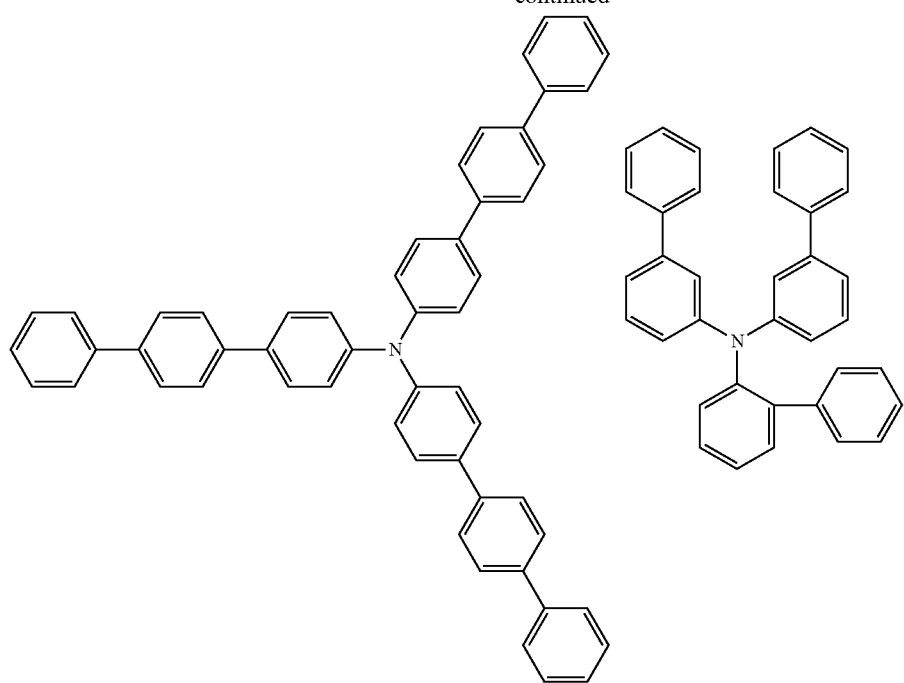
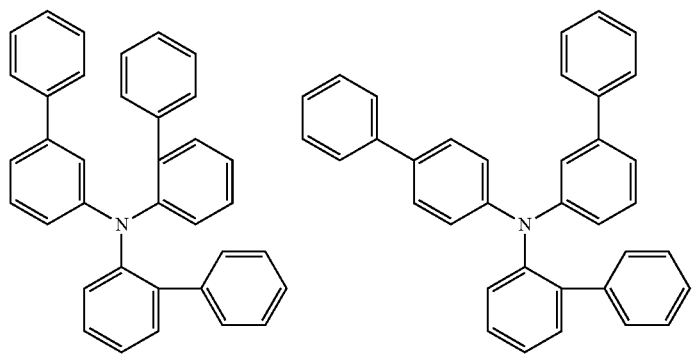
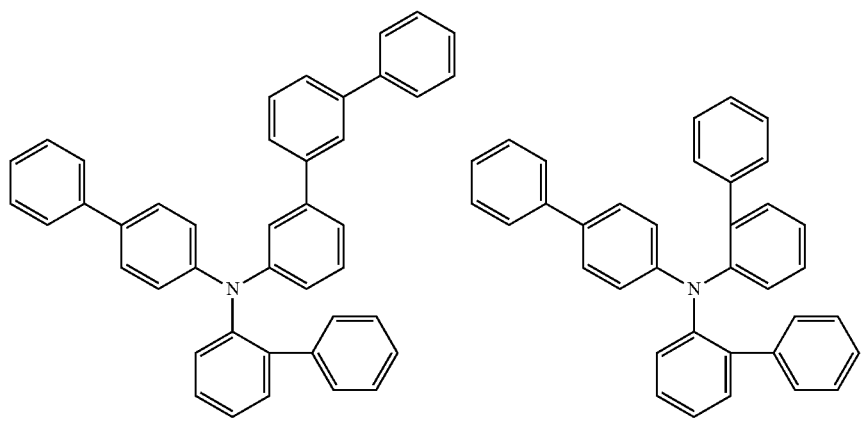

-continued
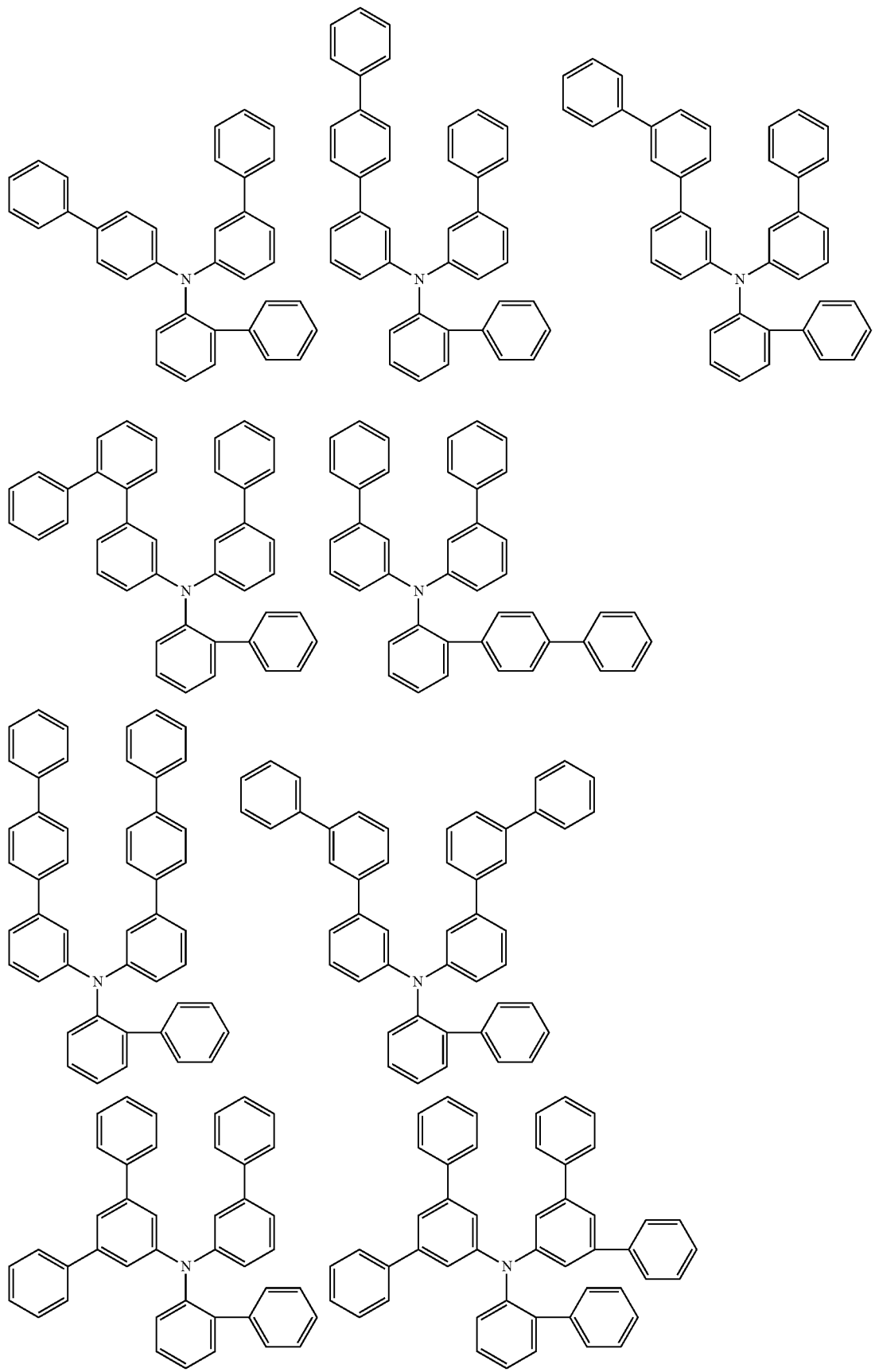

31
32
-continued
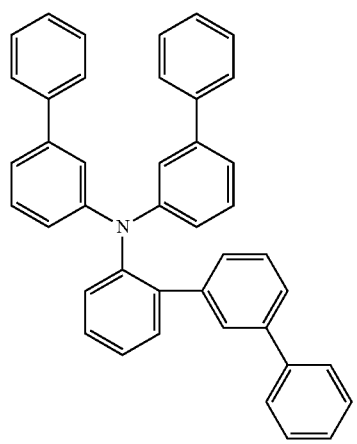
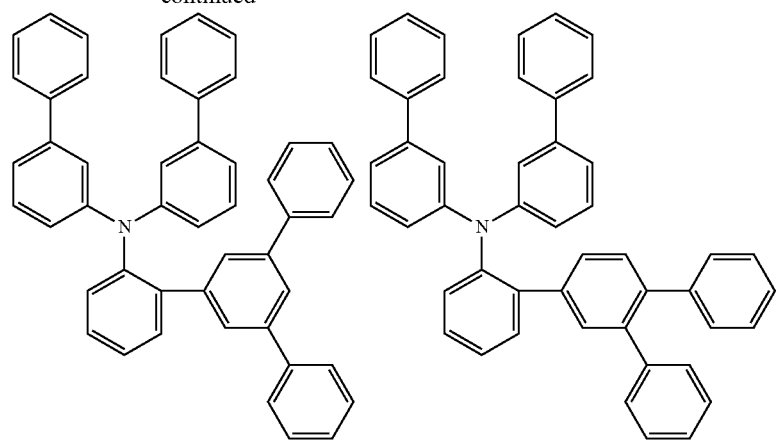
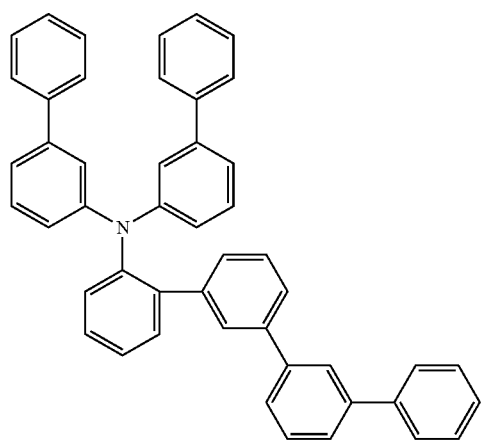
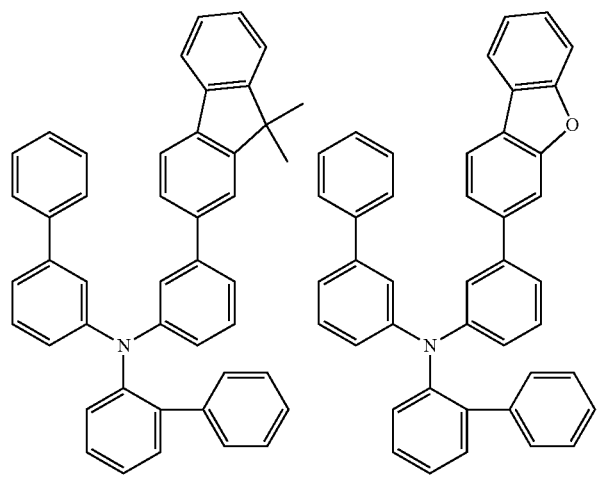
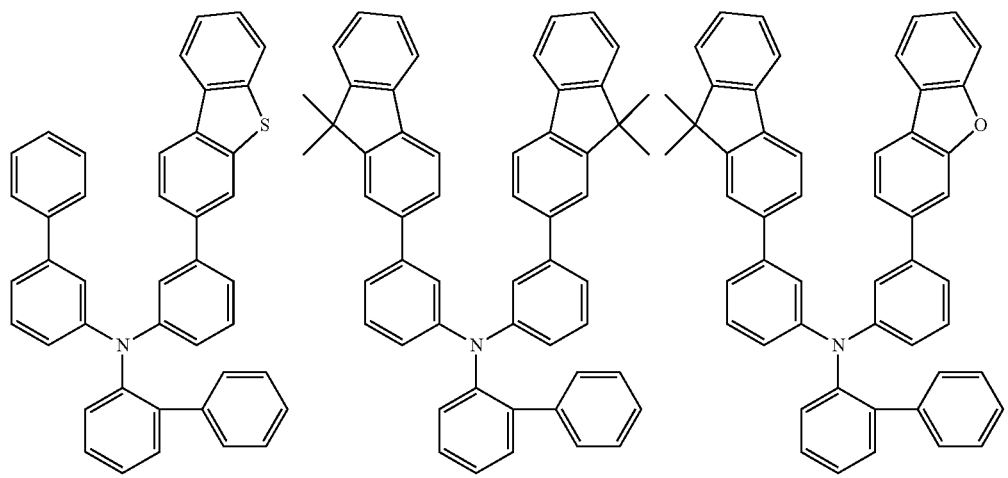

-continued
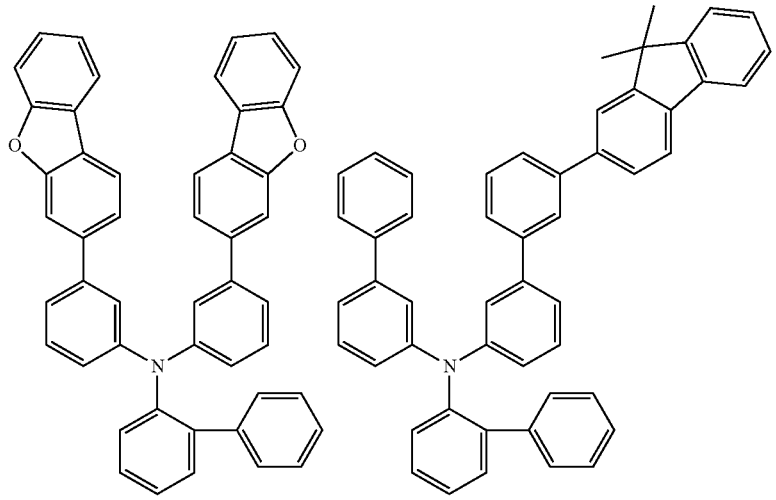
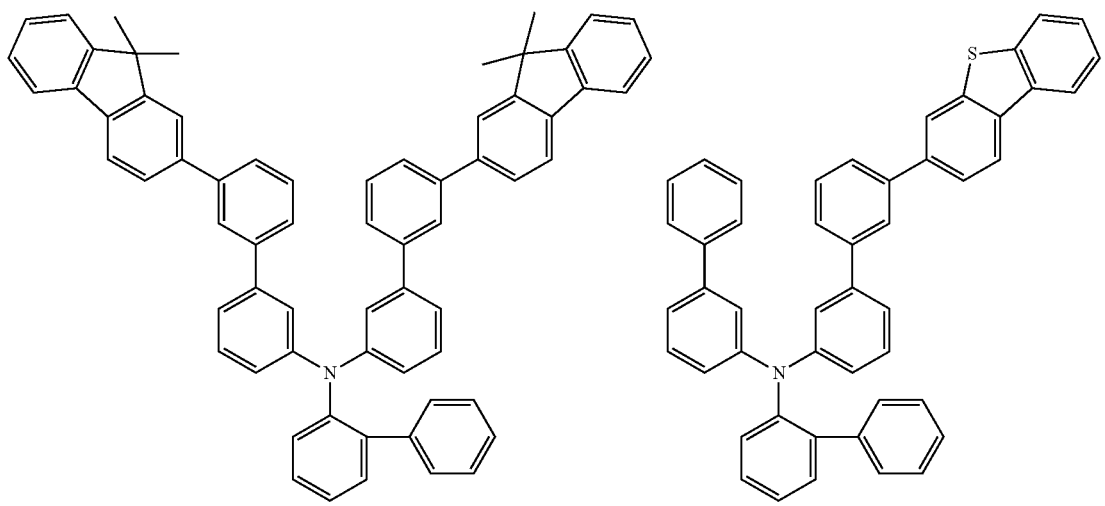
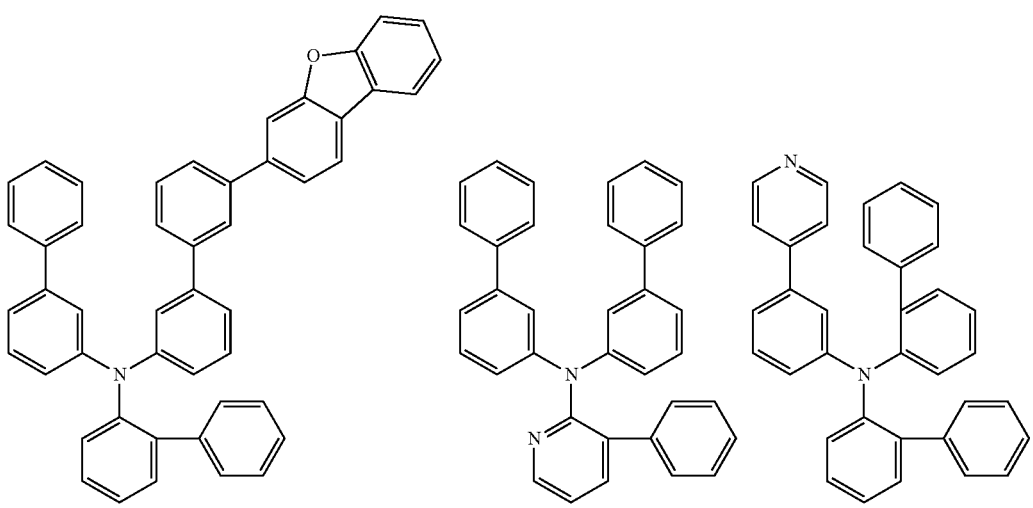

-continued
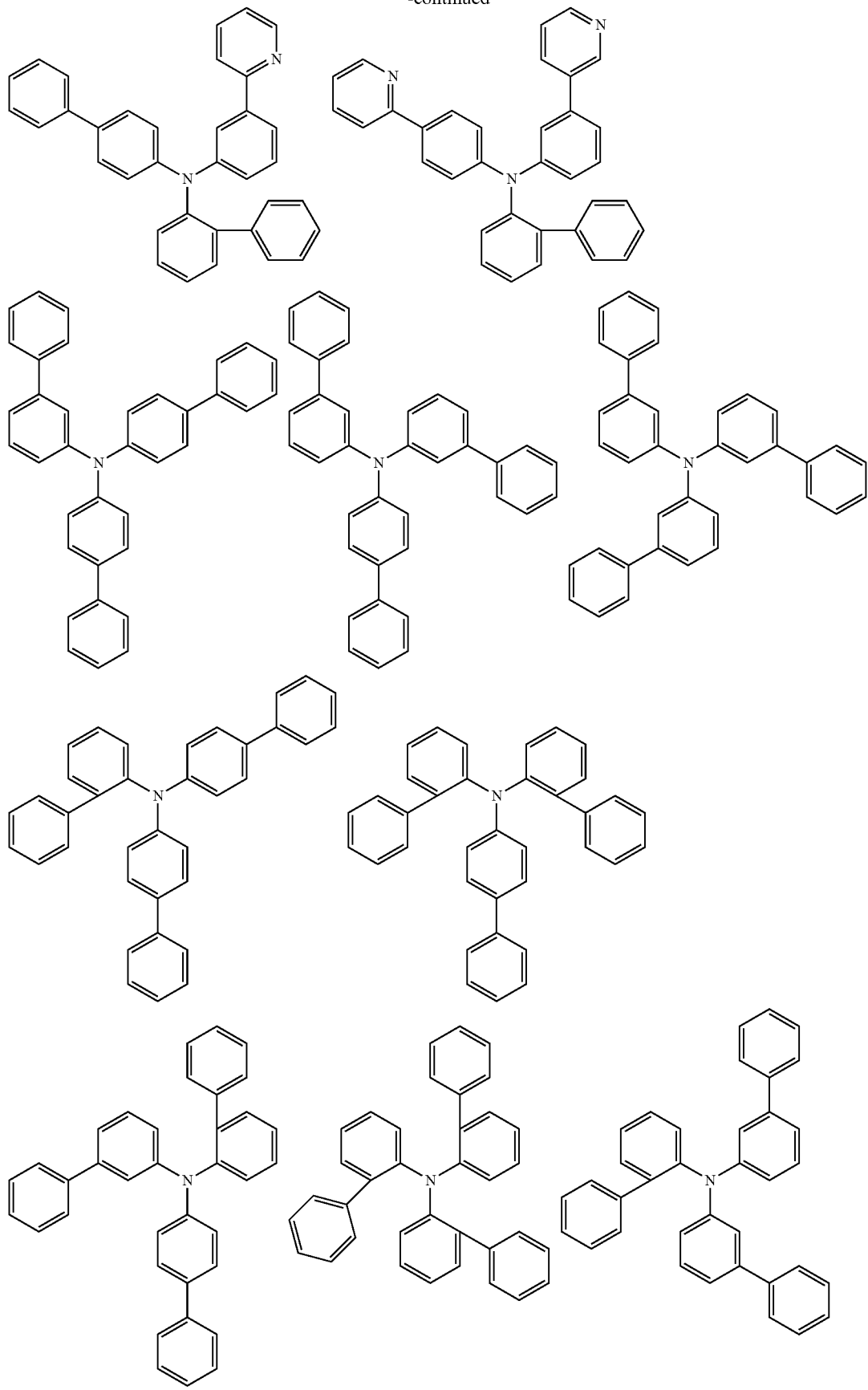

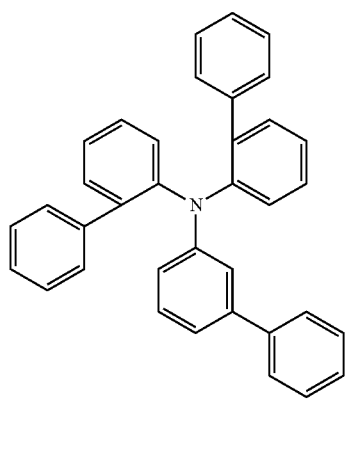
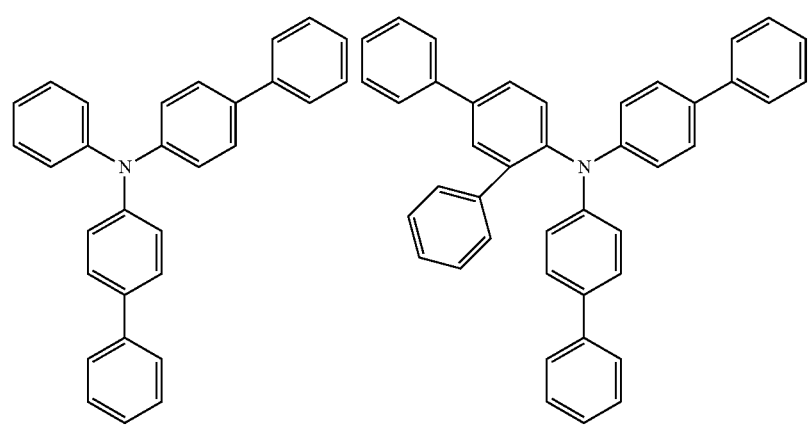
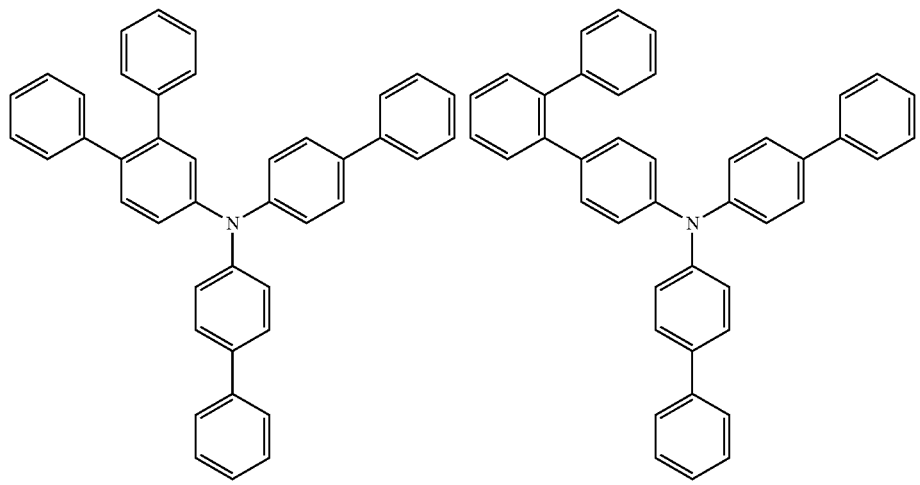
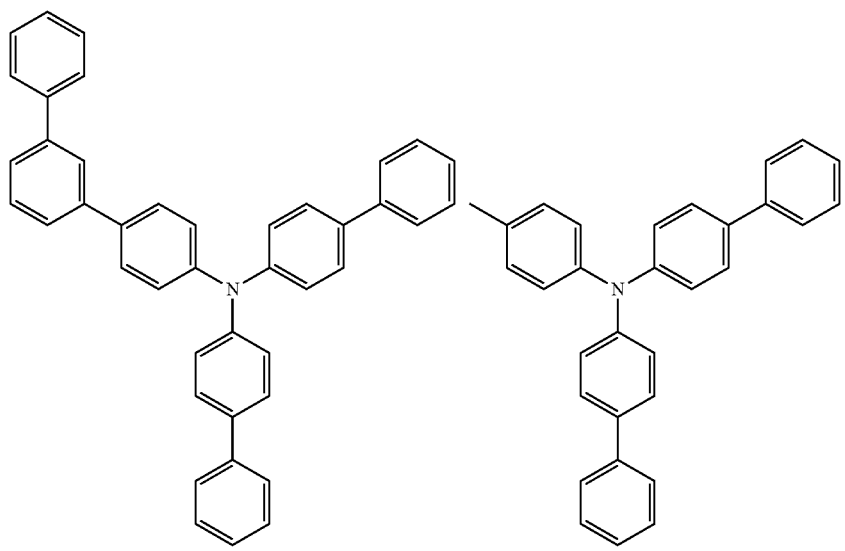

-continued
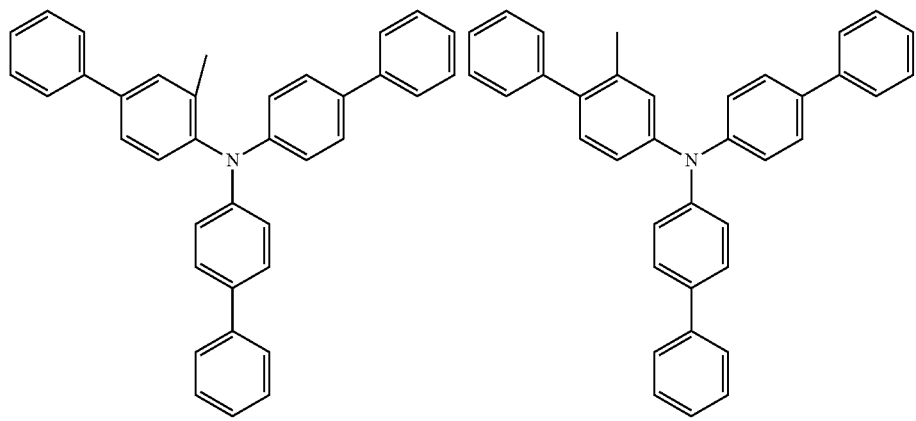
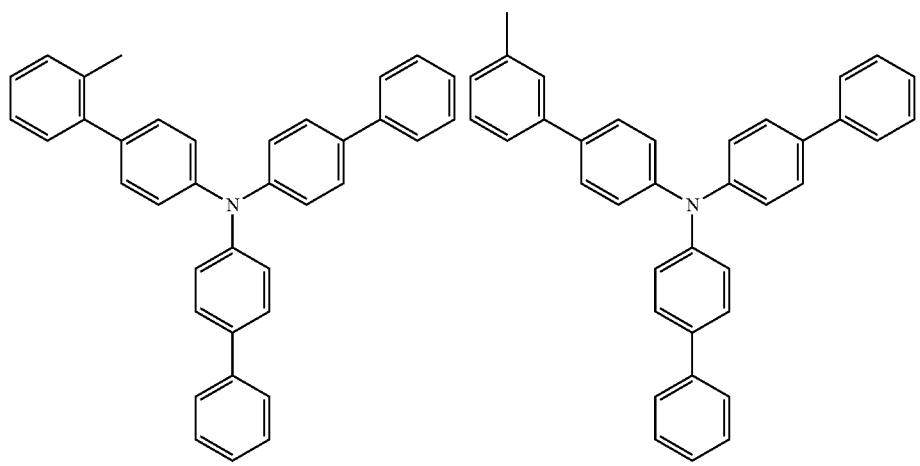
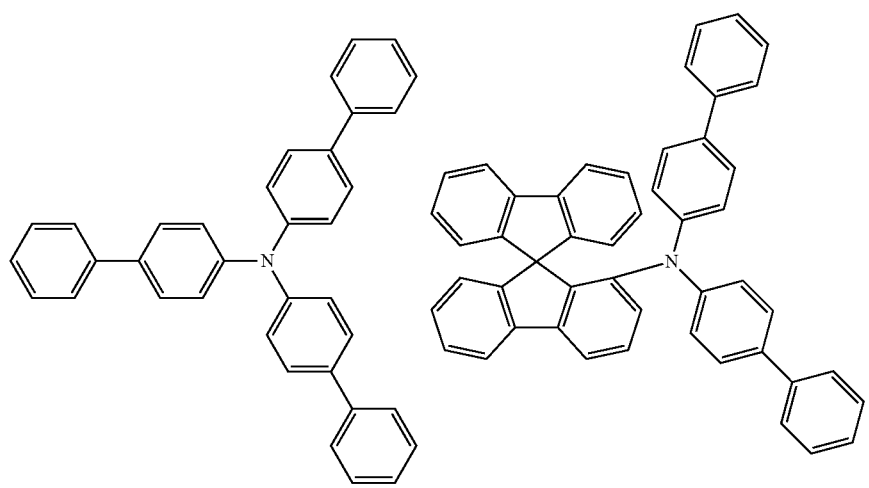

-continued
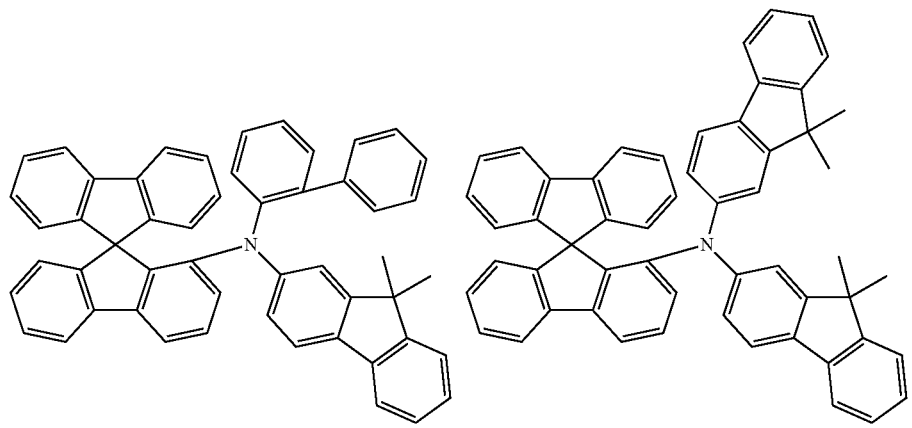
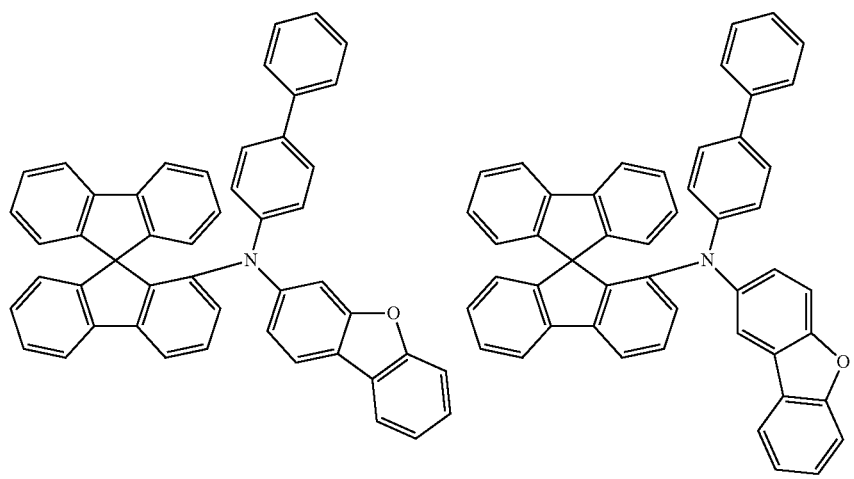
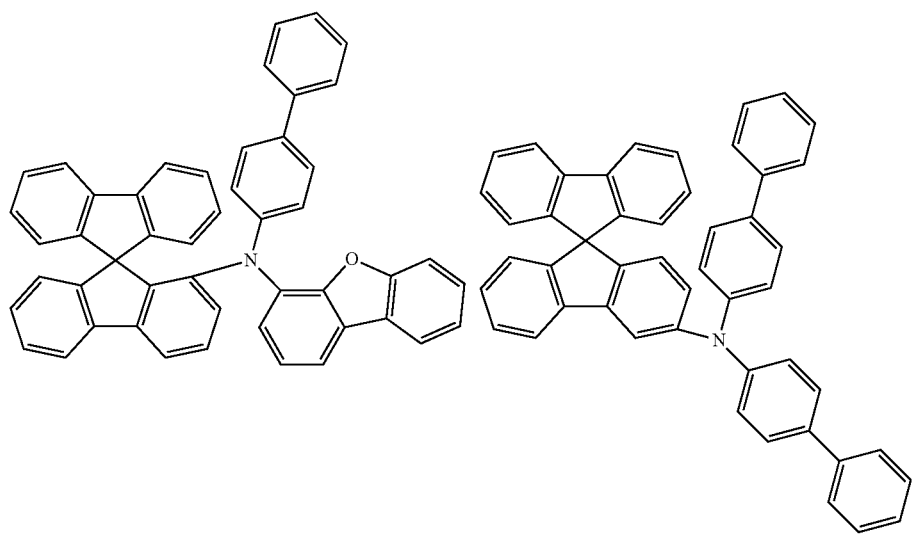

-continued
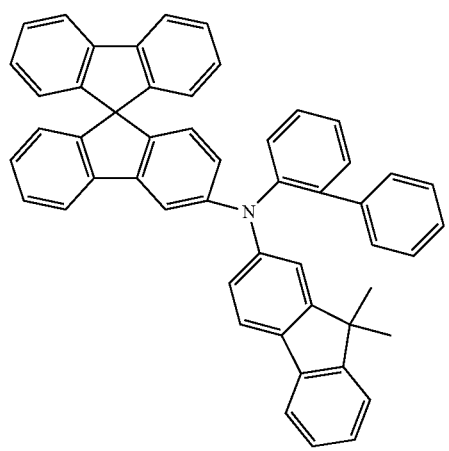
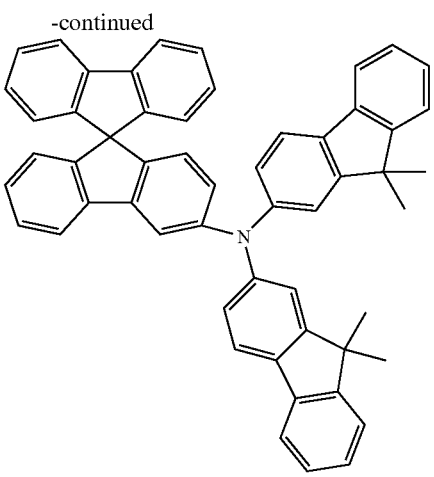
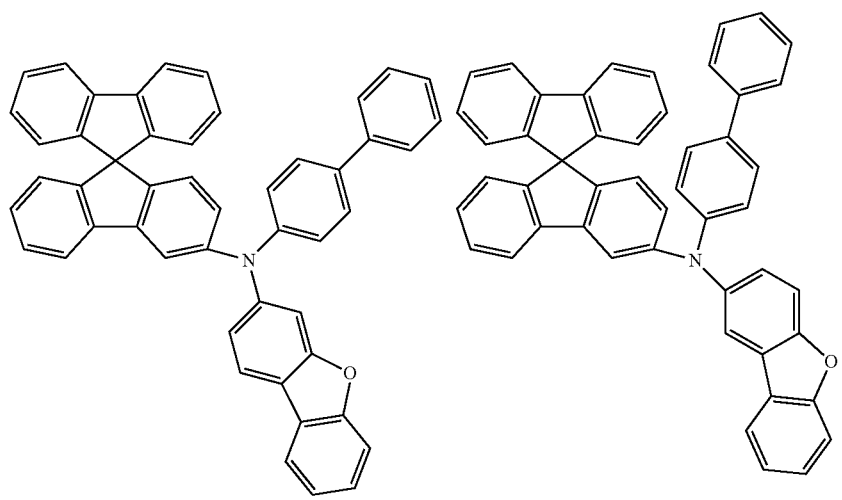
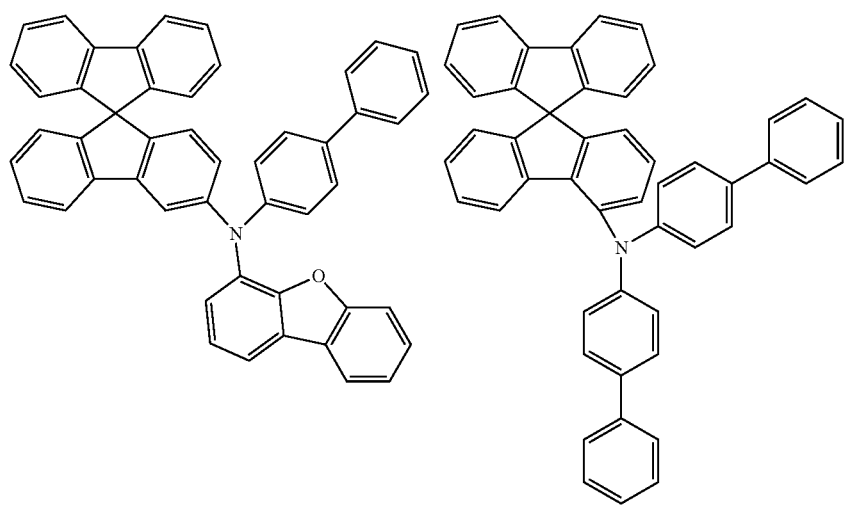

-continued
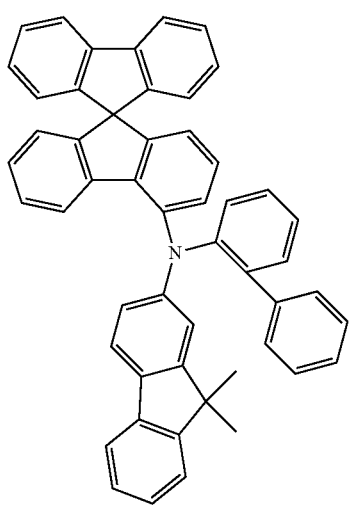
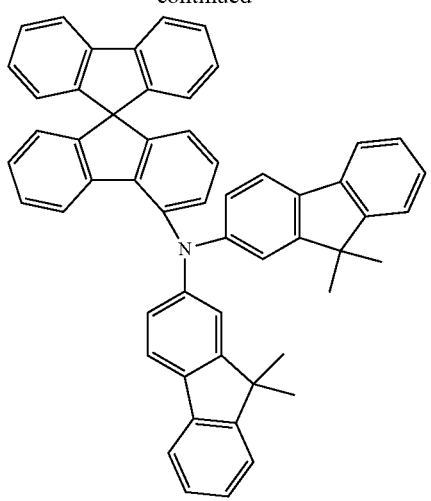
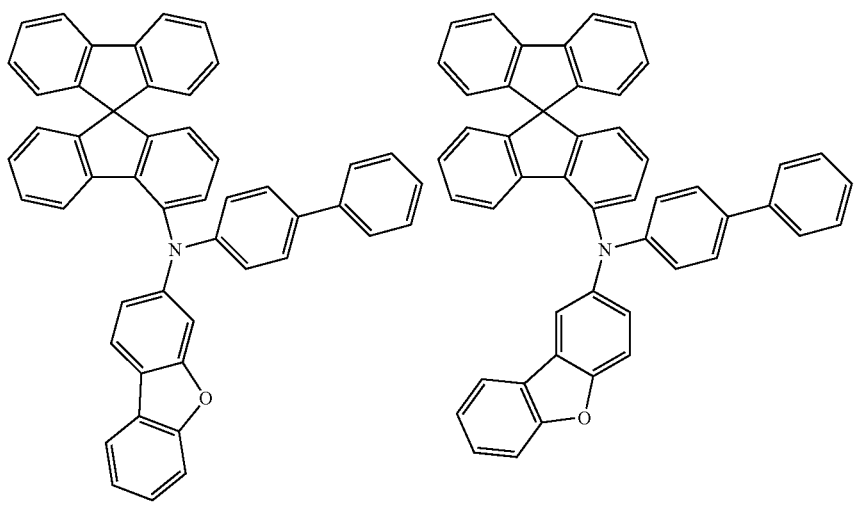
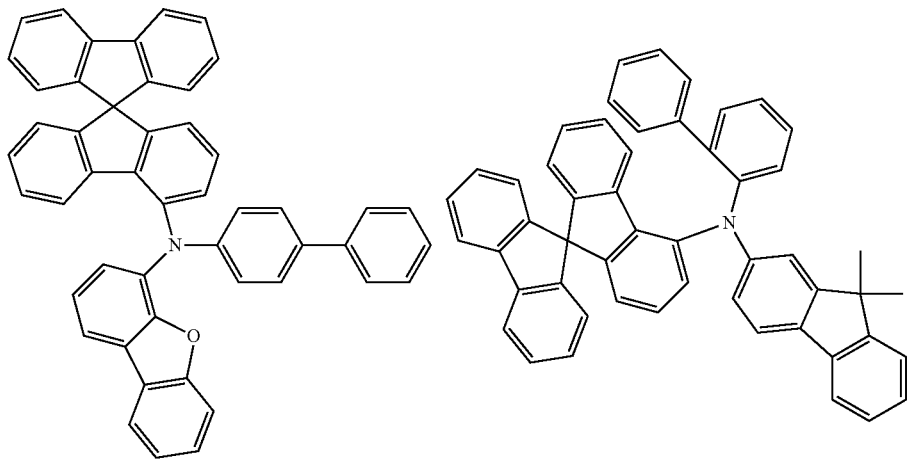

-continued
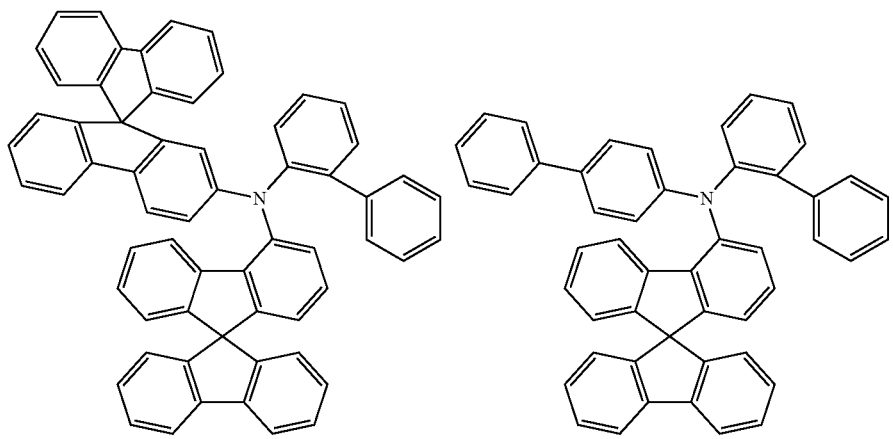
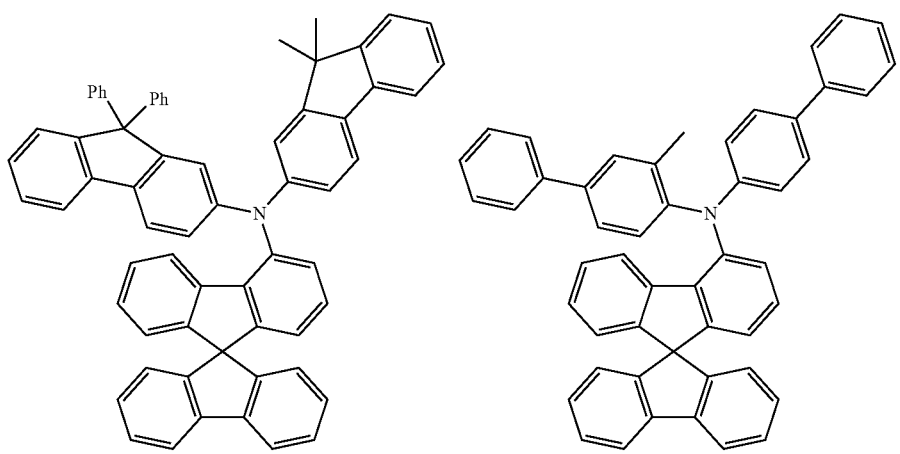
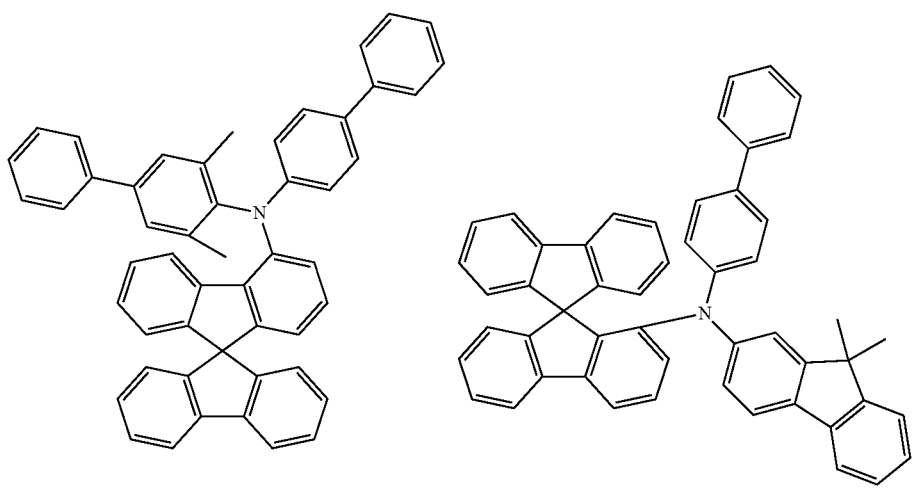

-continued
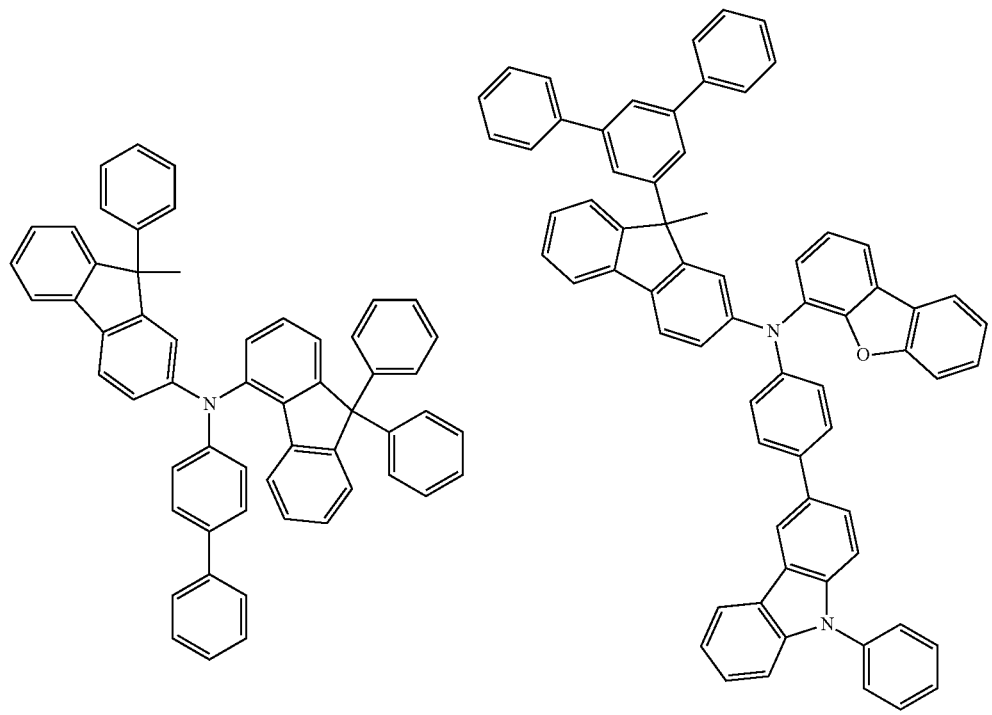
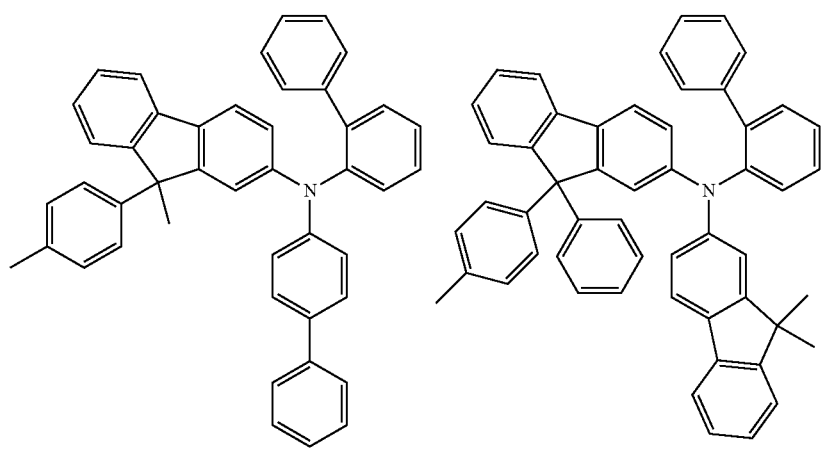
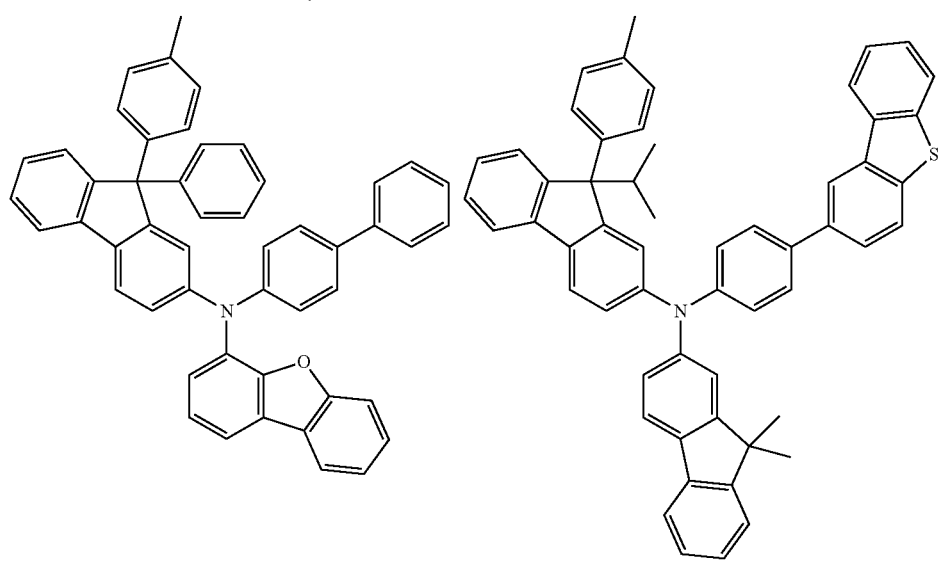

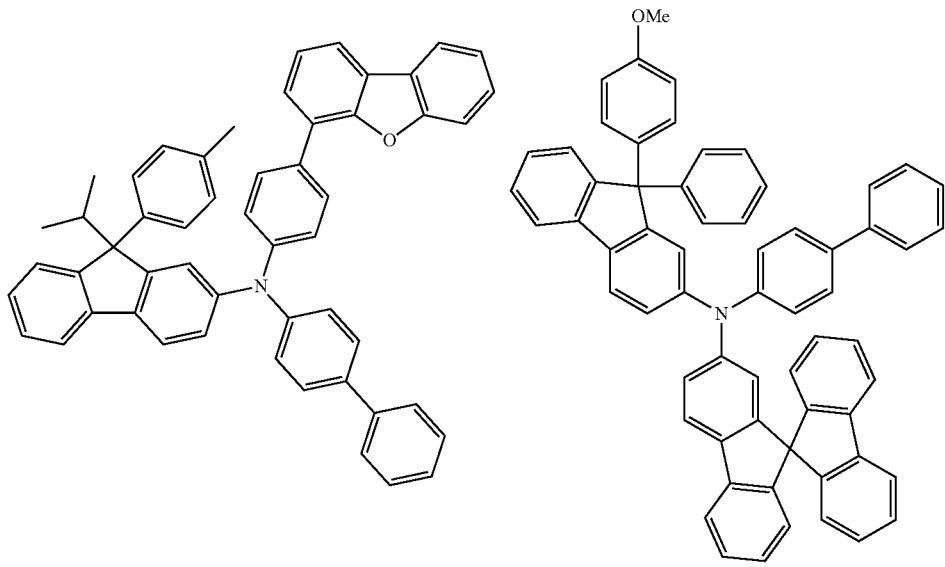
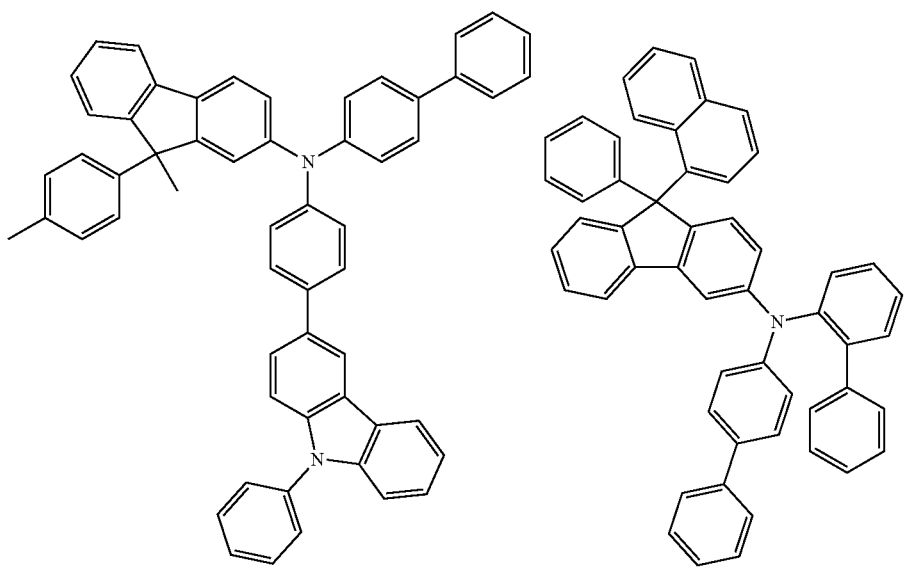
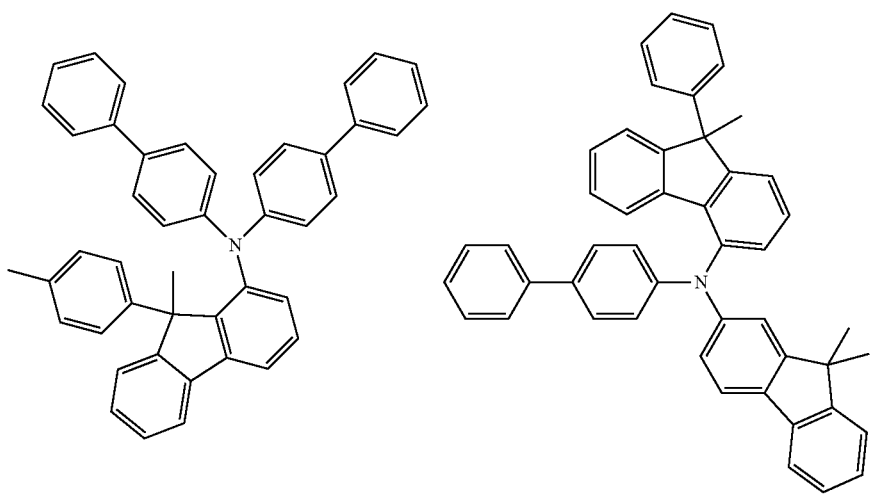

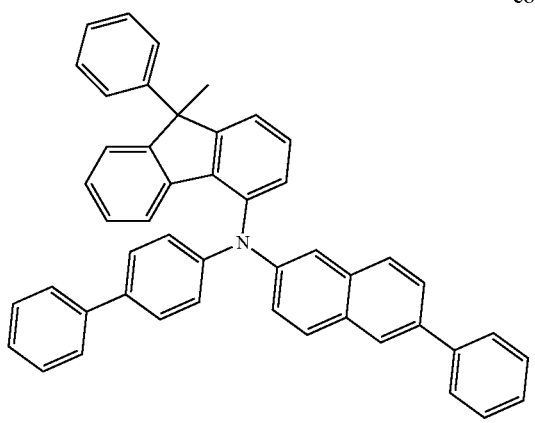
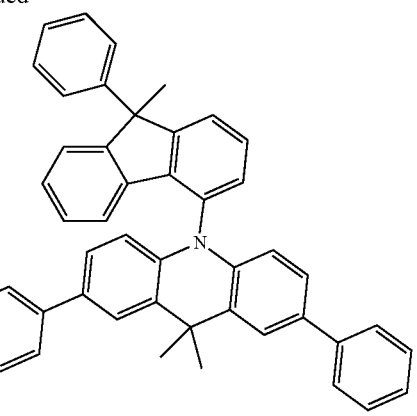
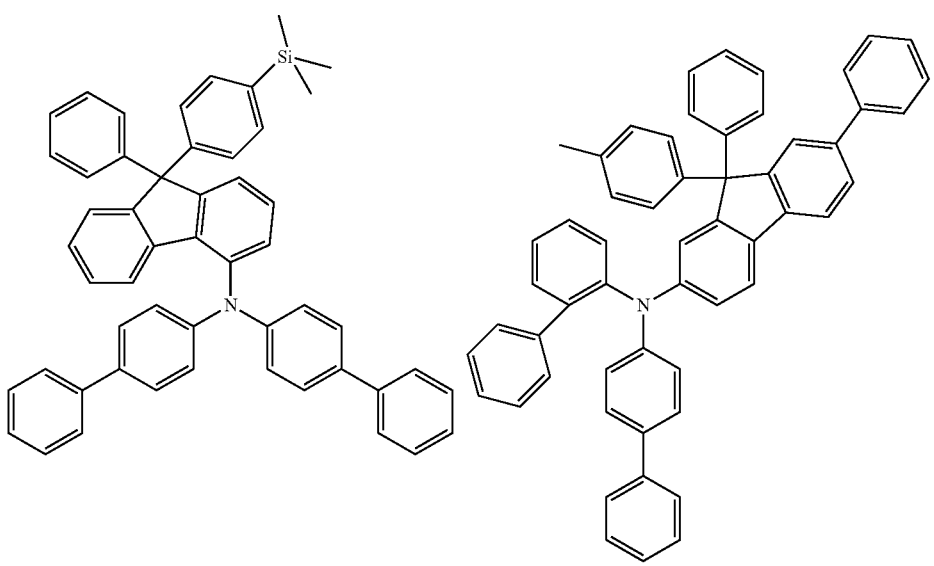
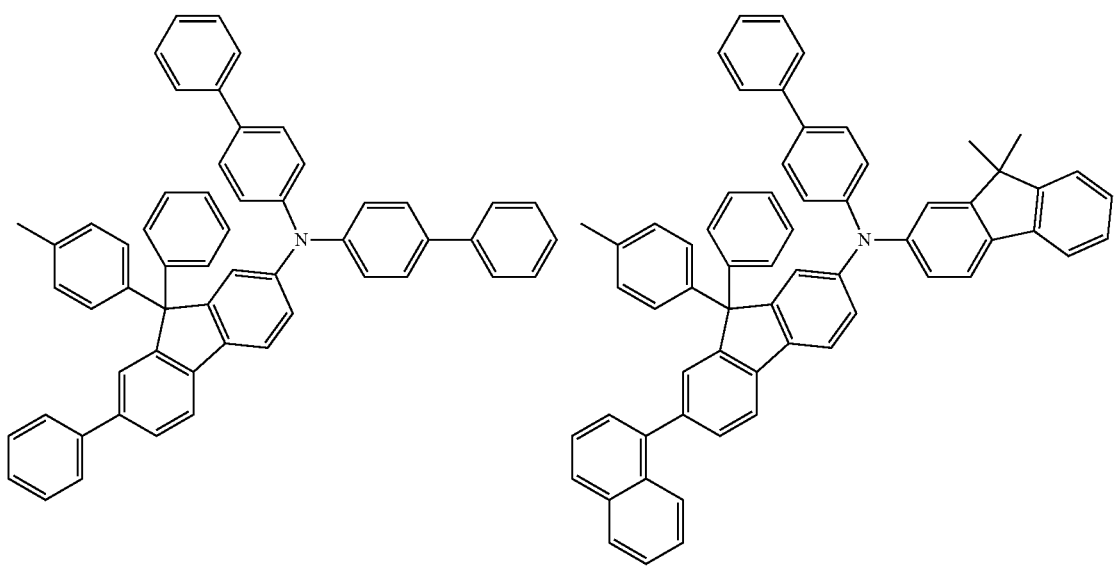

-continued
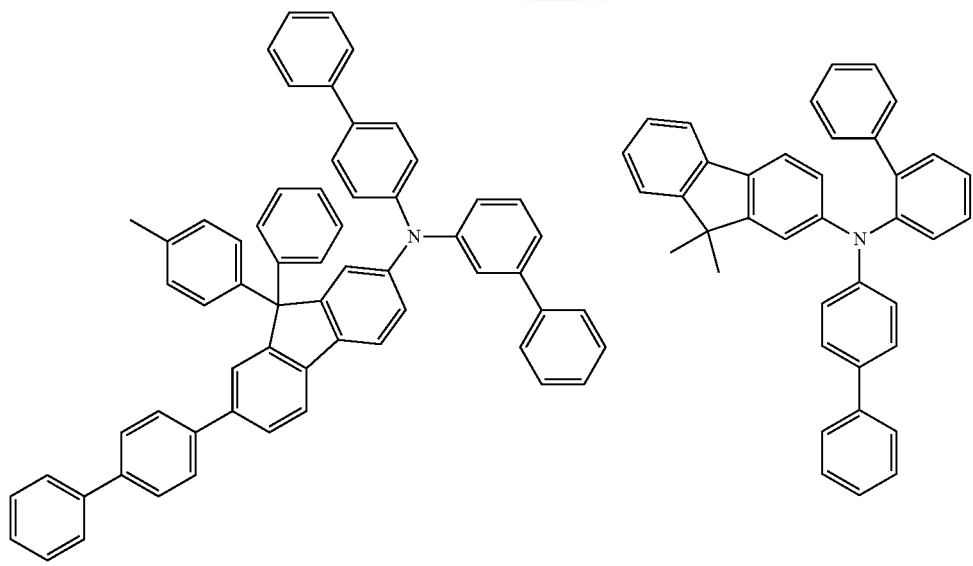
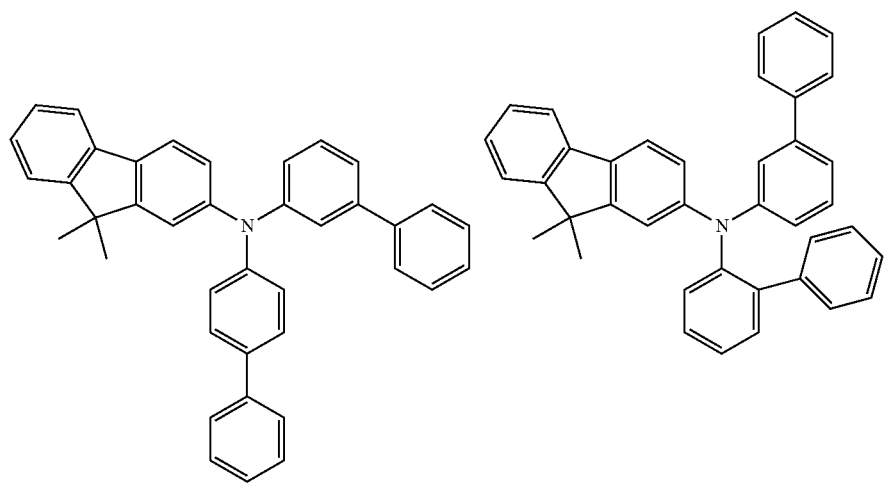
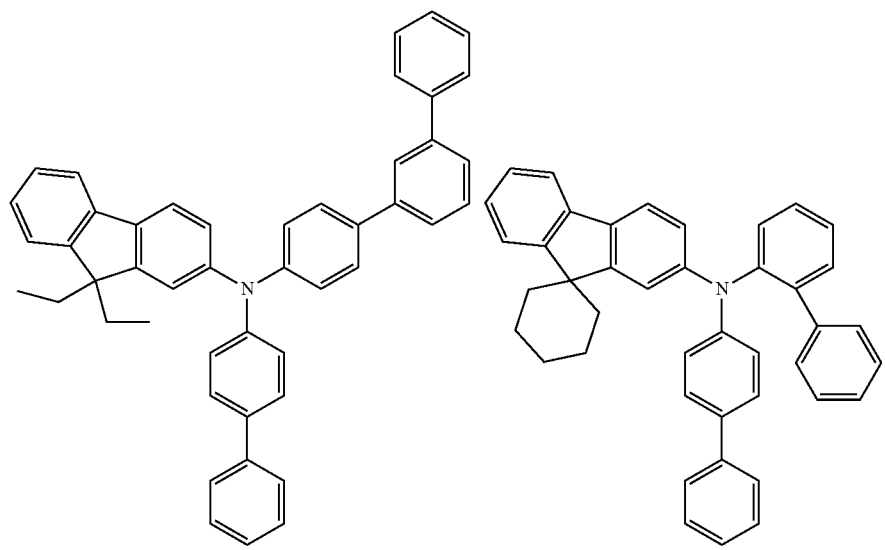

-continued
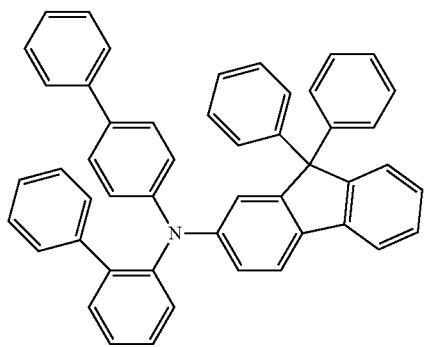
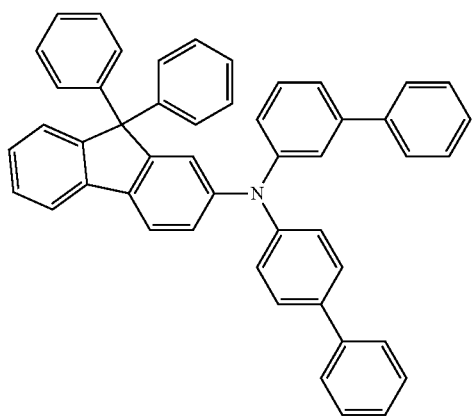
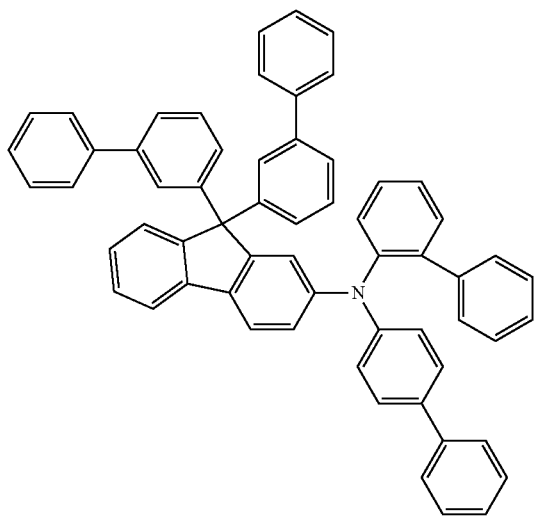
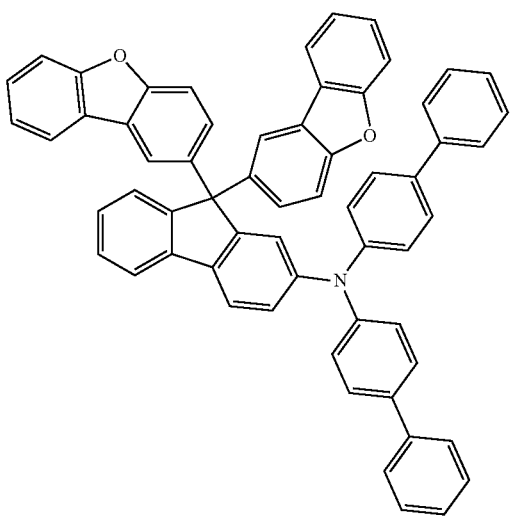
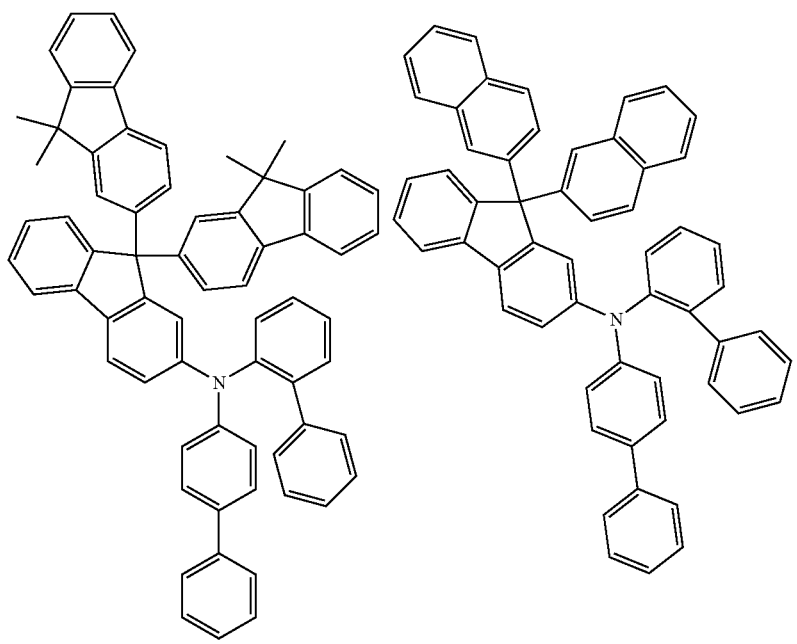

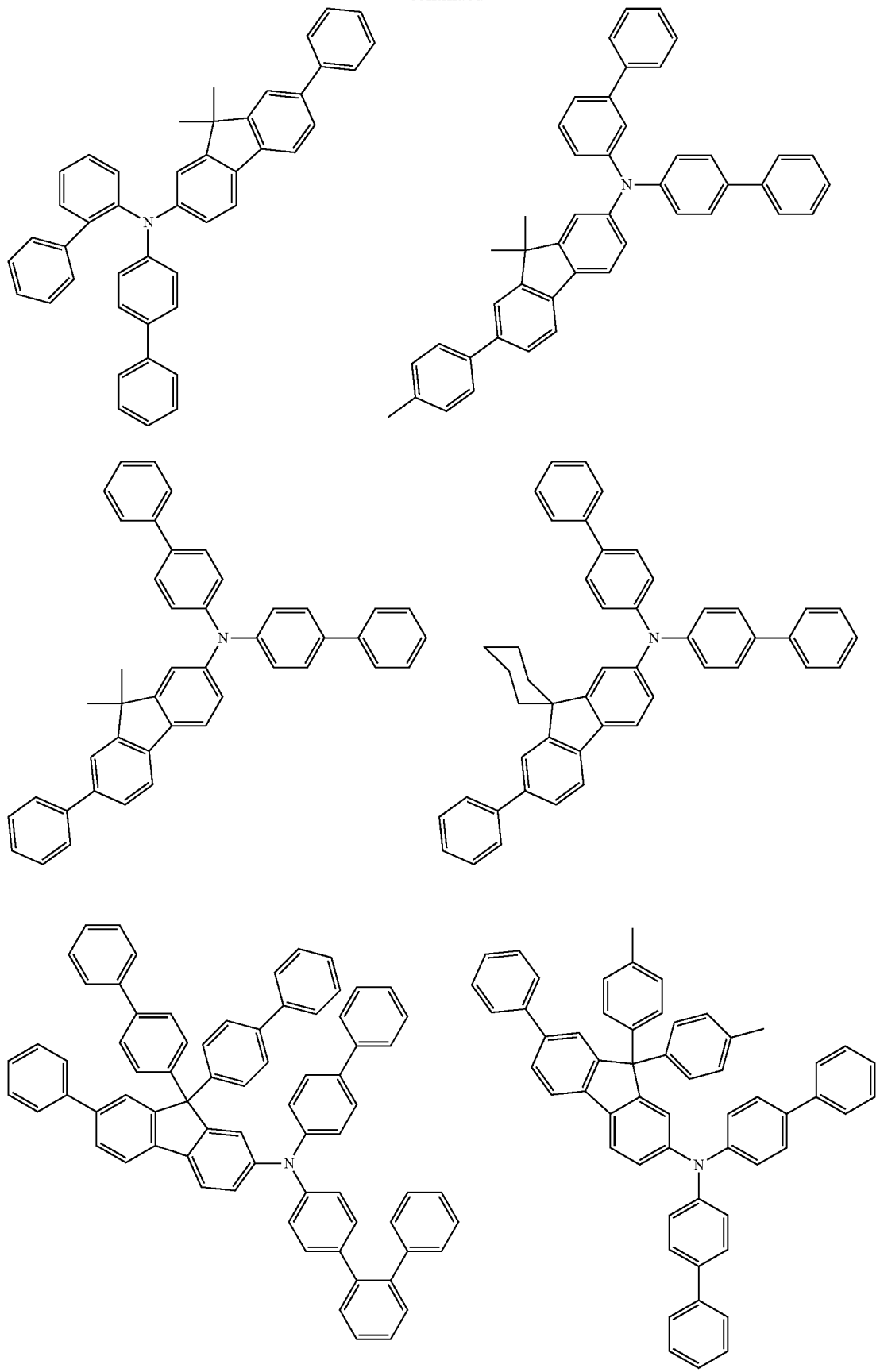

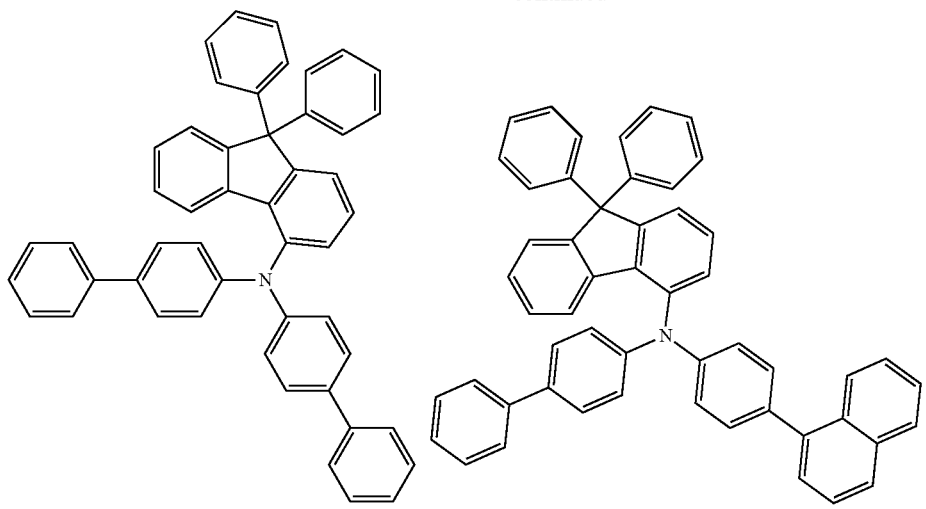
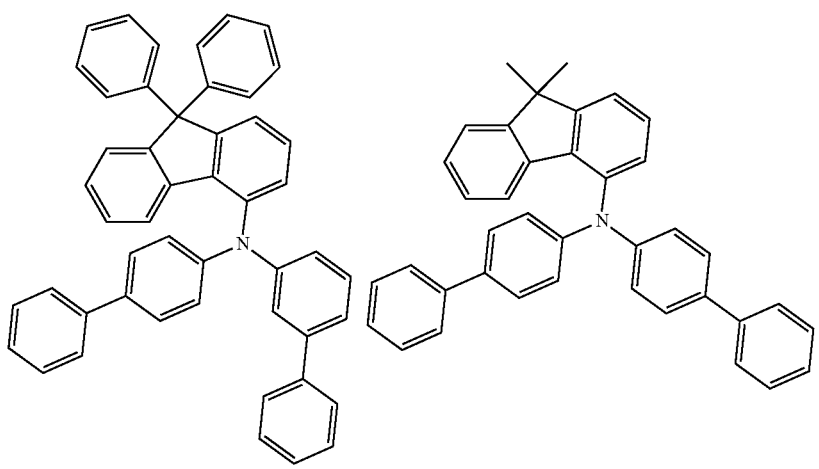
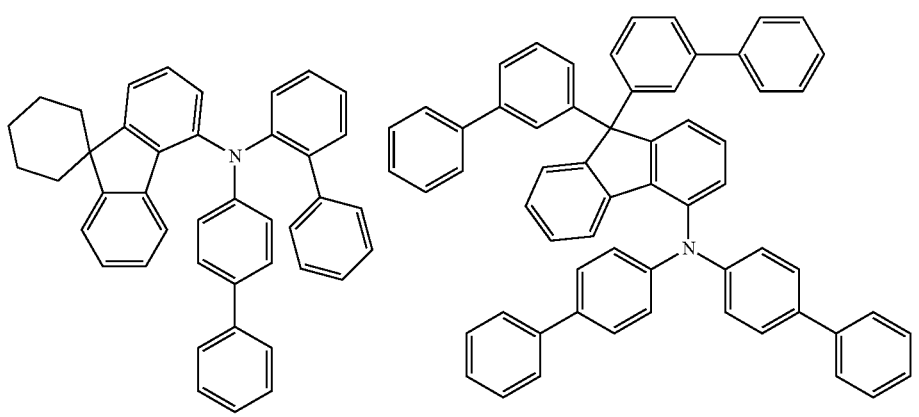

-continued
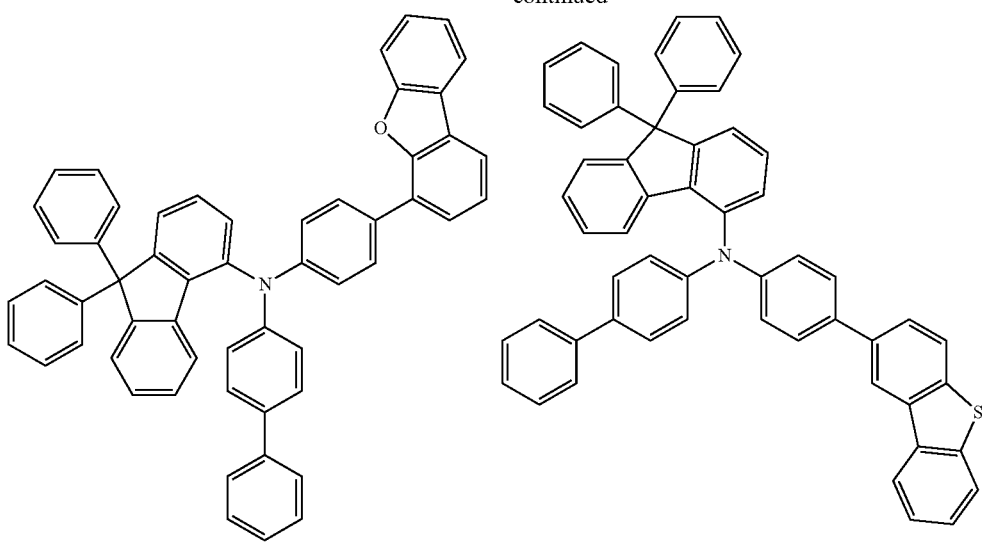
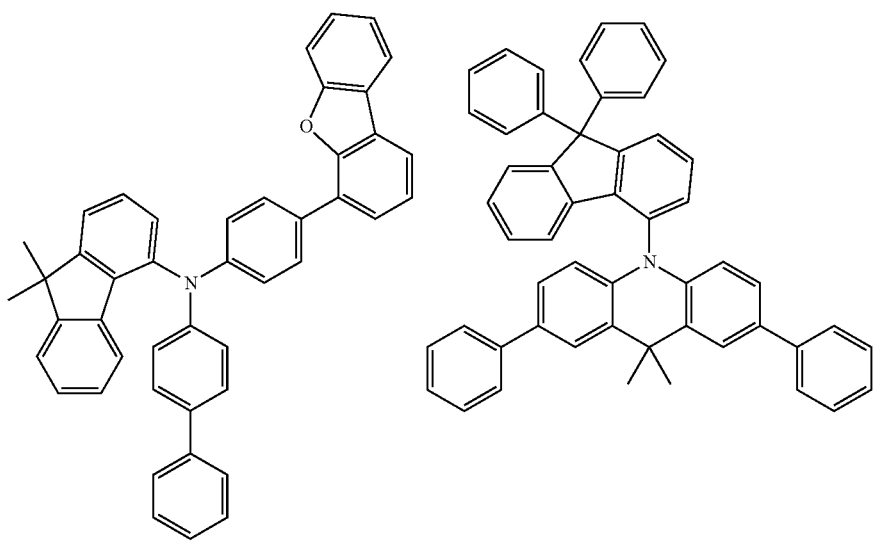
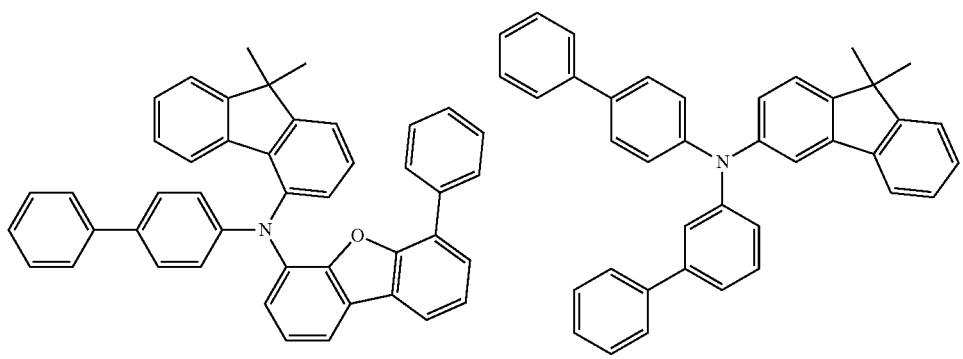

-continued
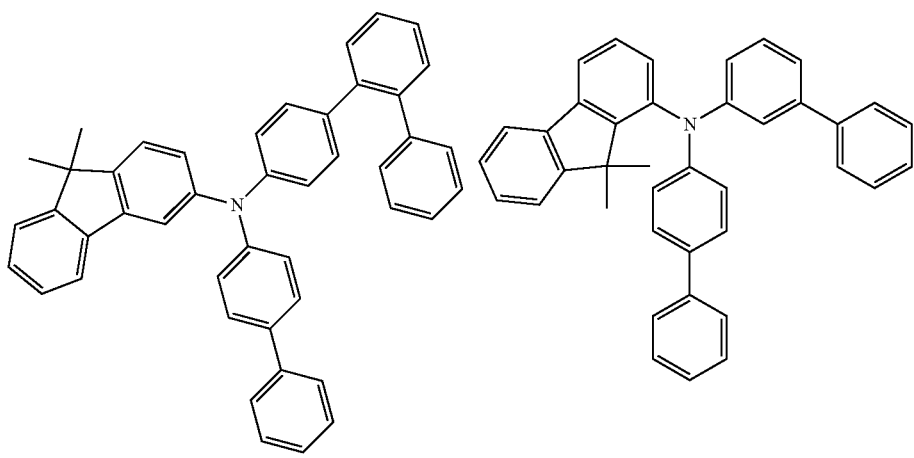
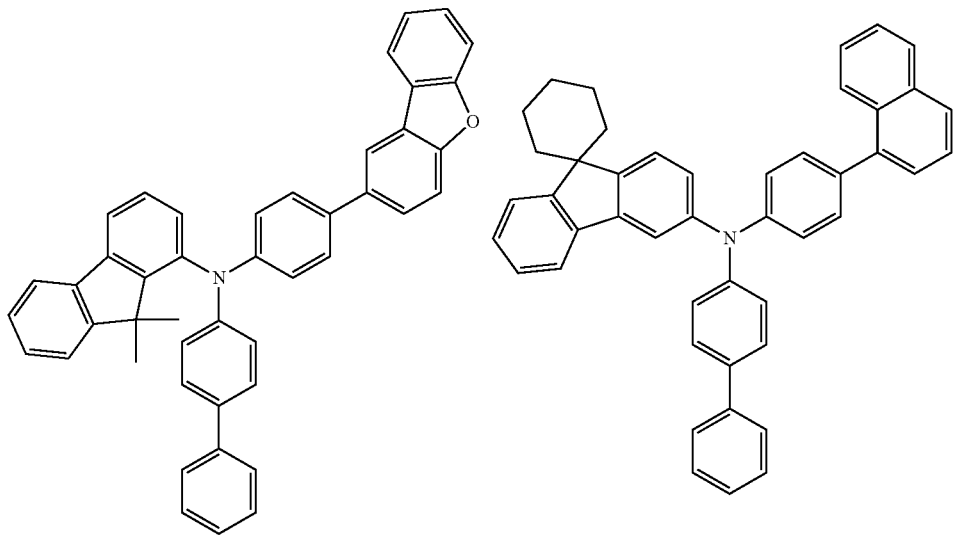
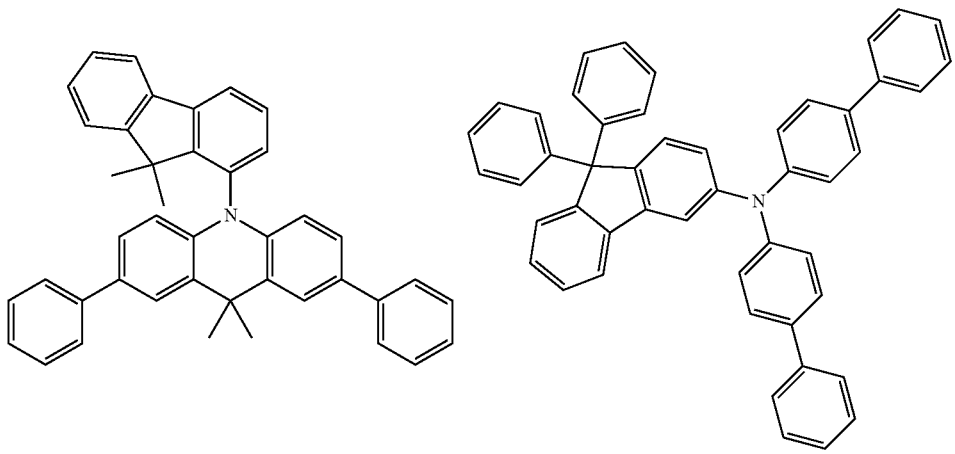

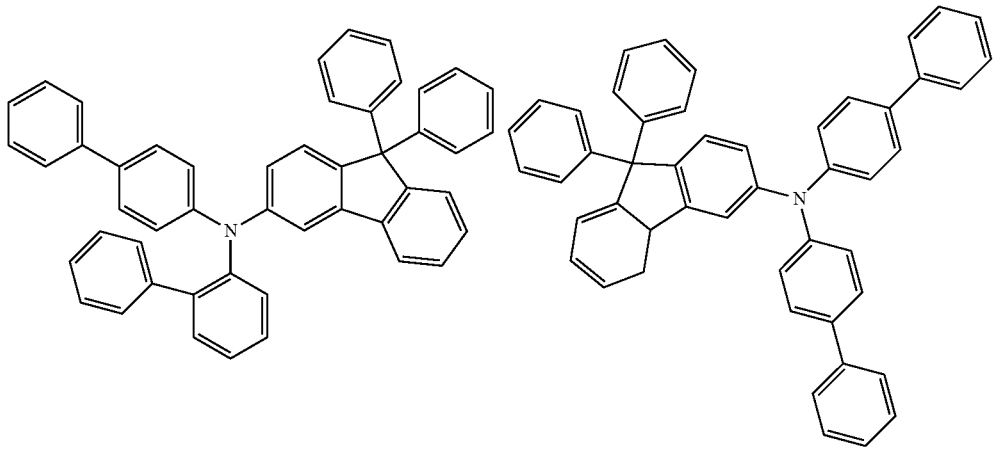
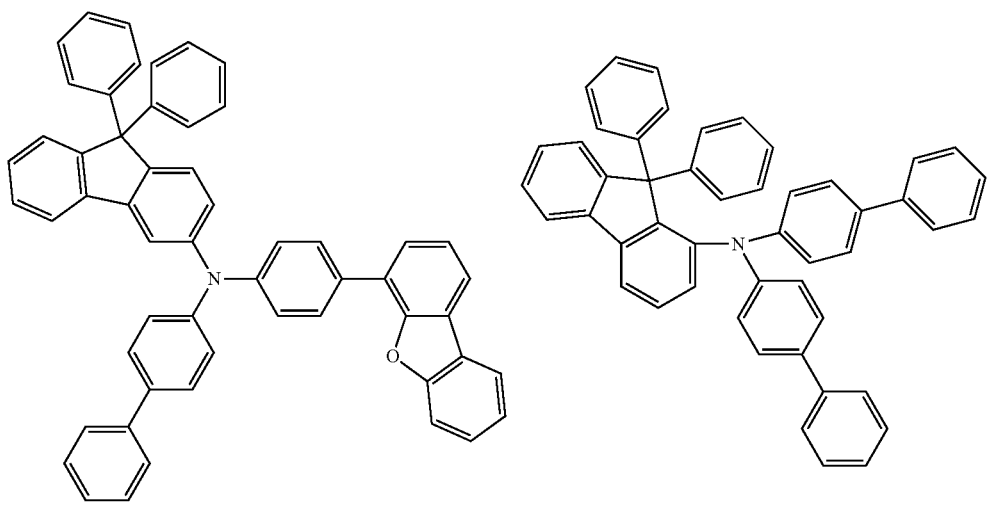
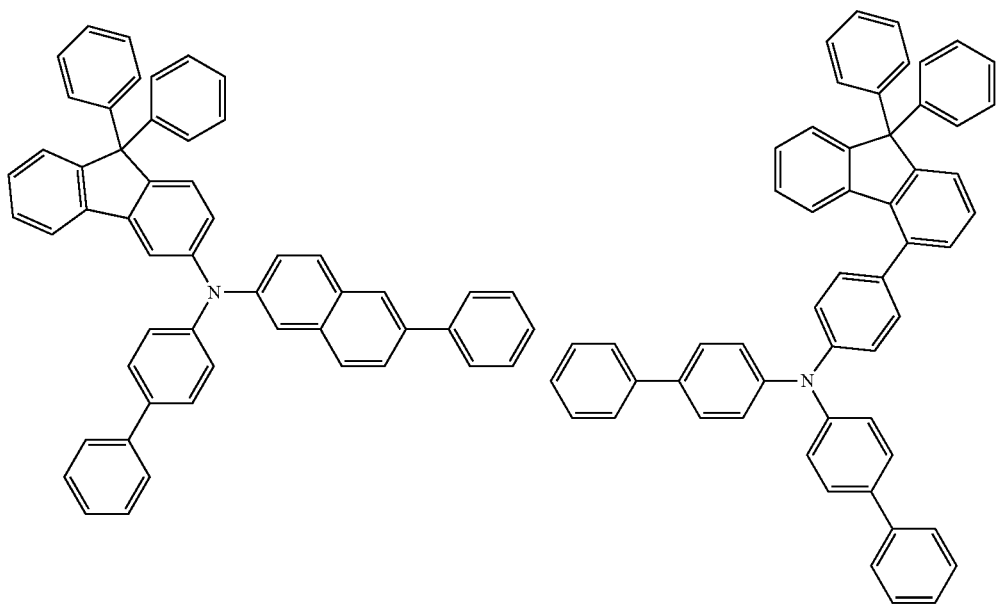

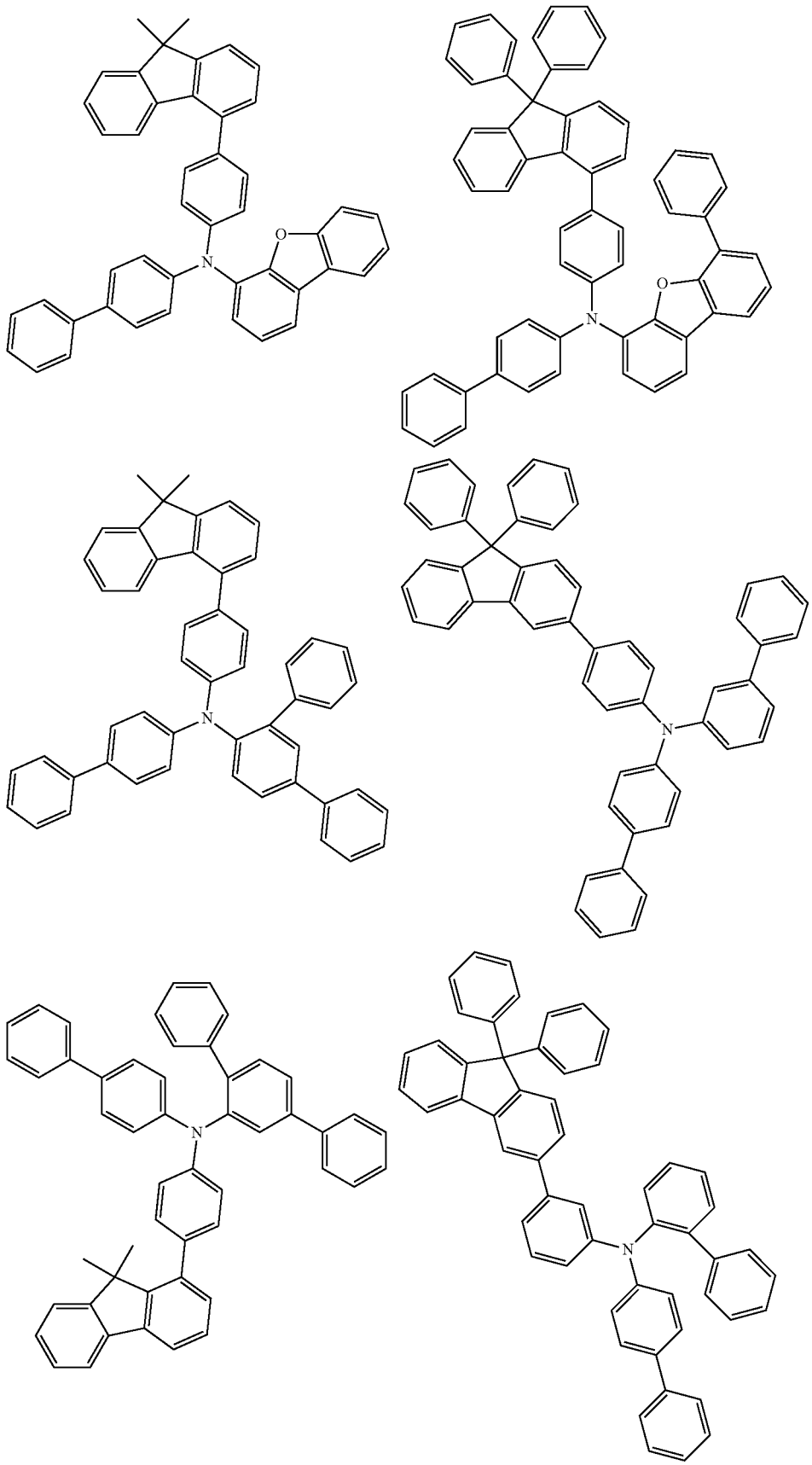

71
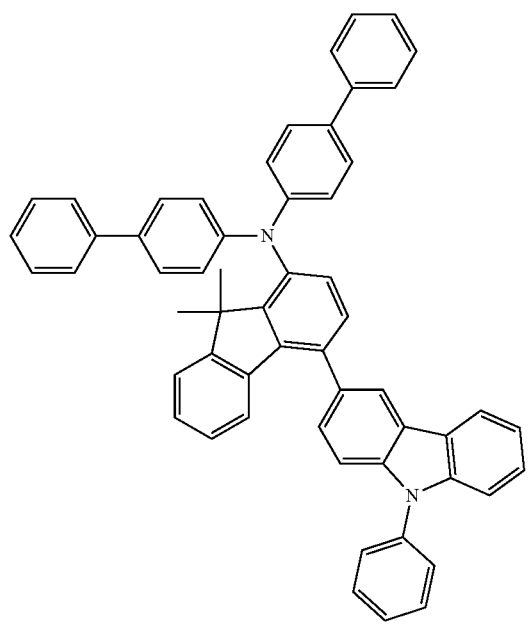
72
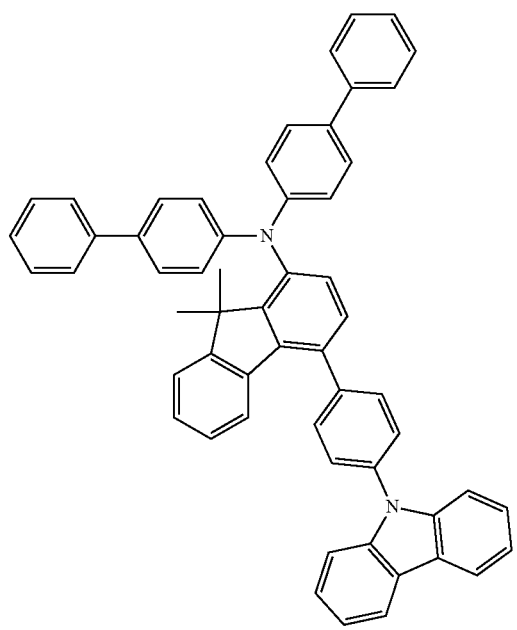
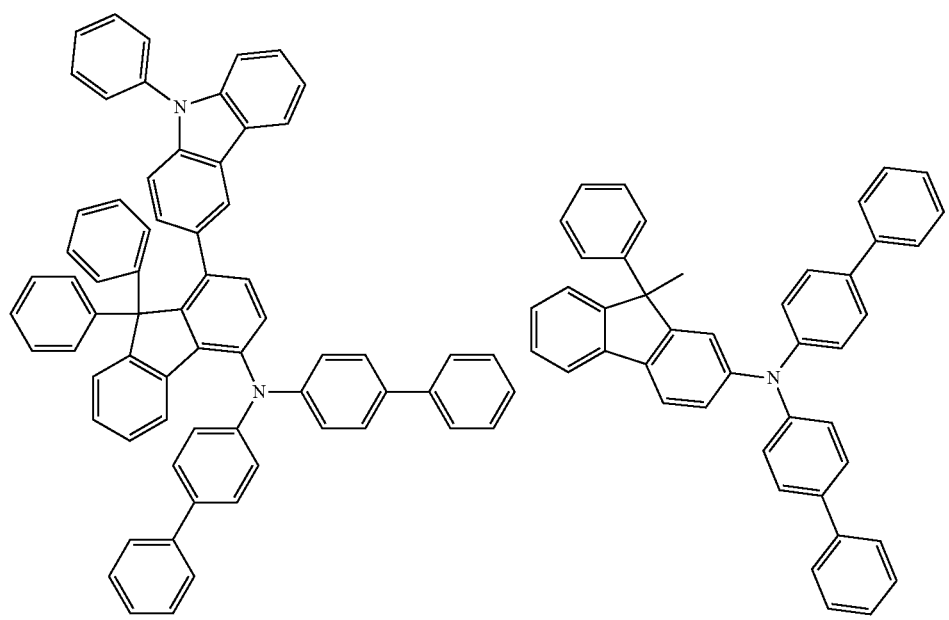

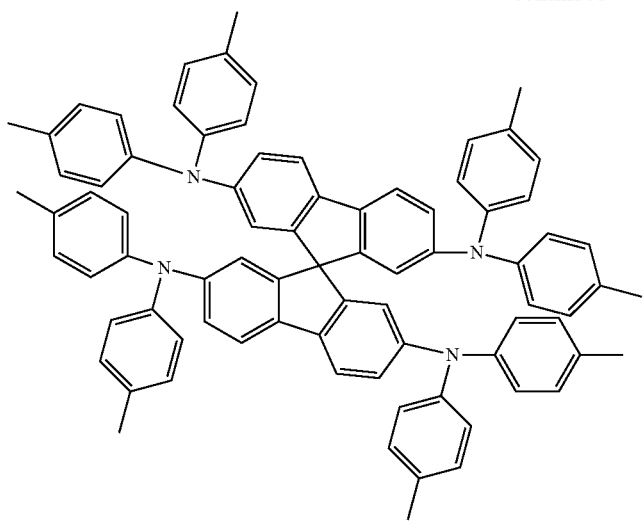
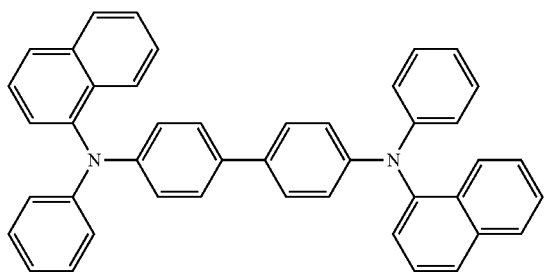
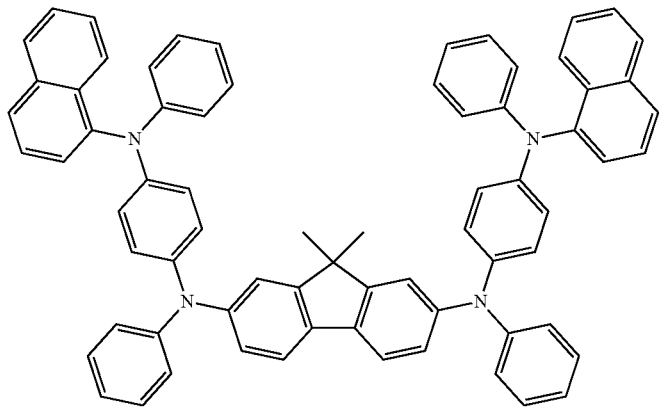
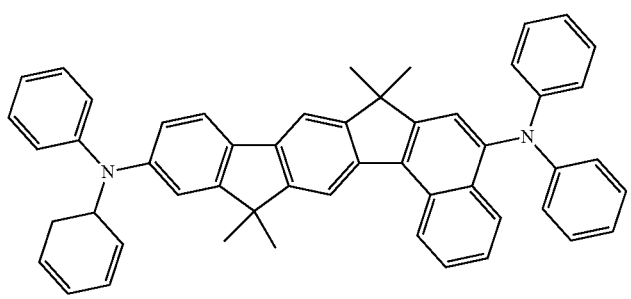

-continued
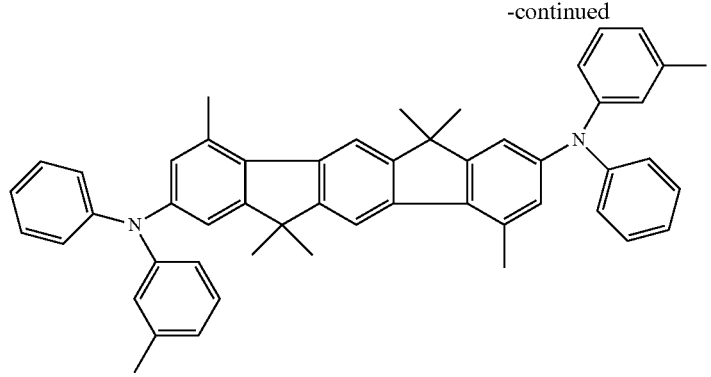
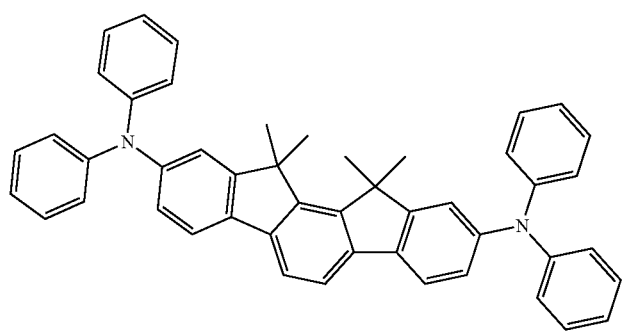
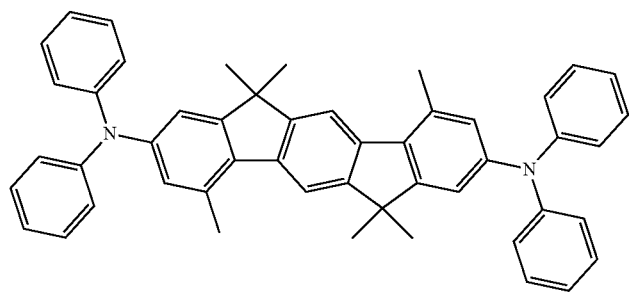
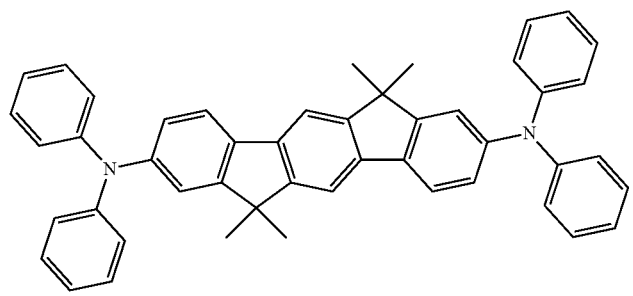

-continued
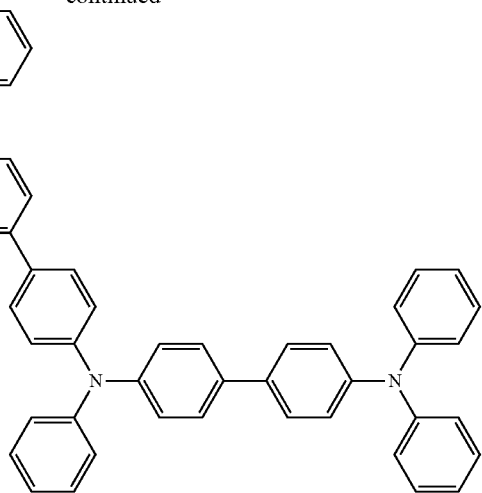
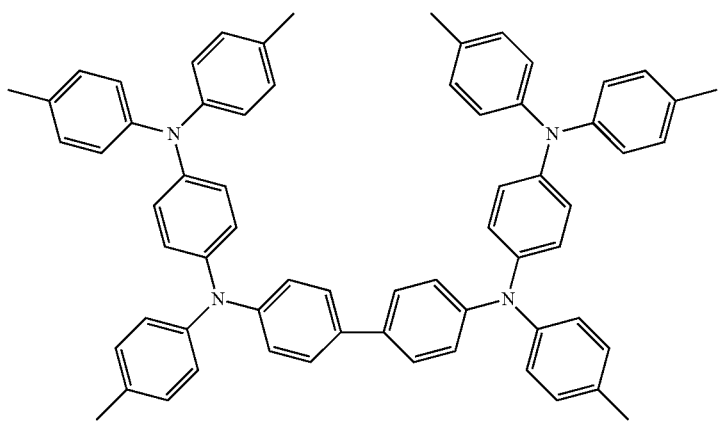
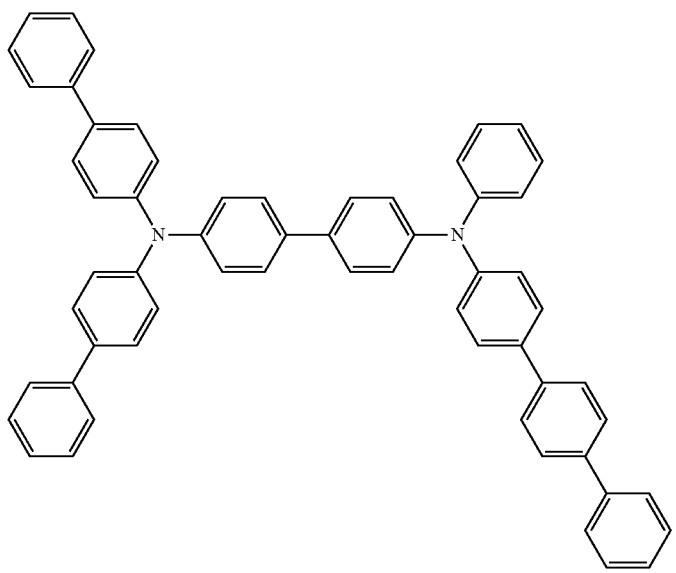

-continued
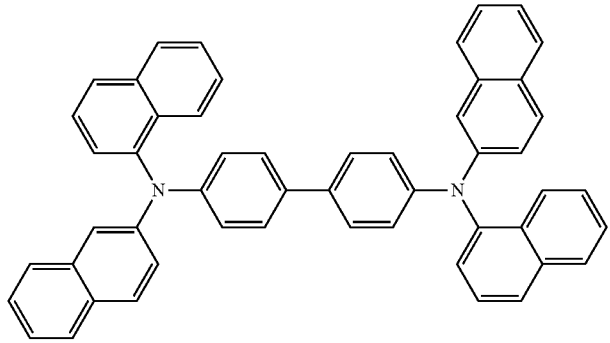
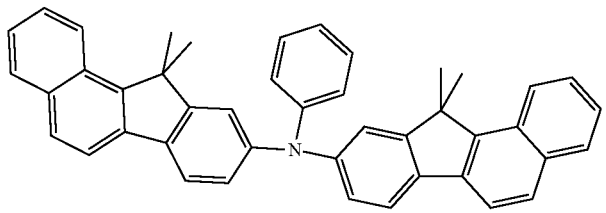
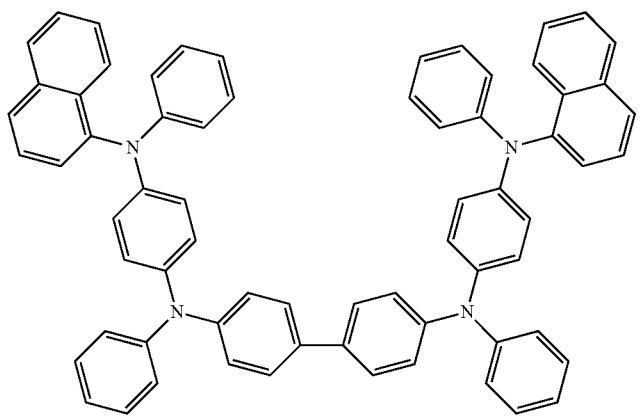
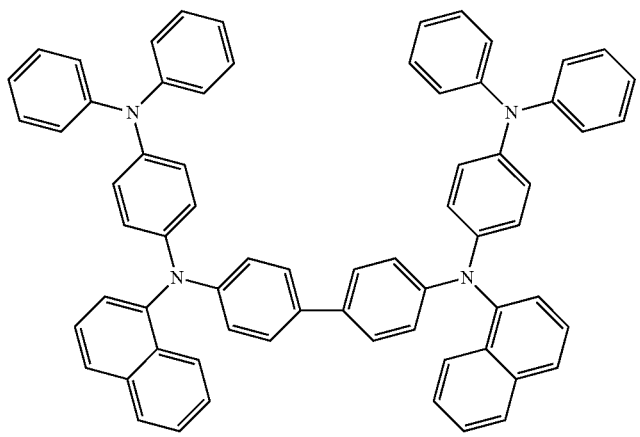

-continued
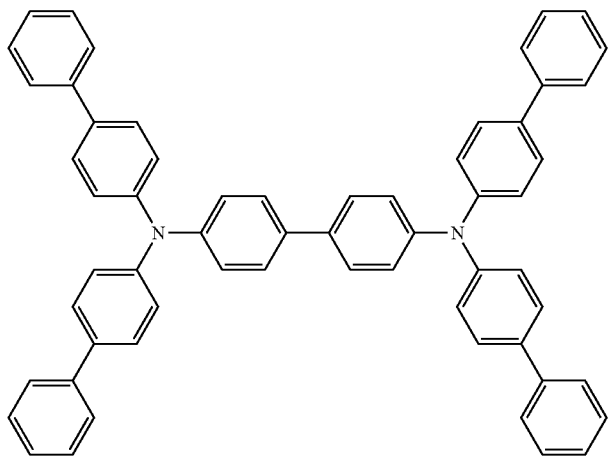
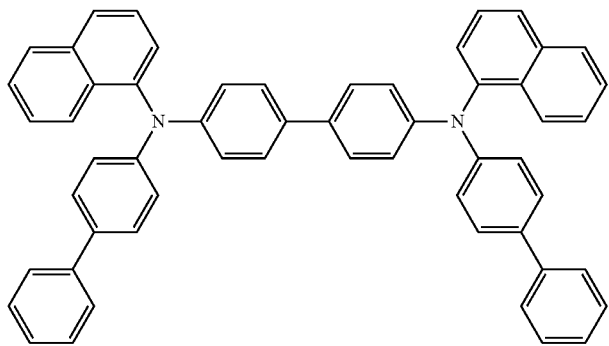
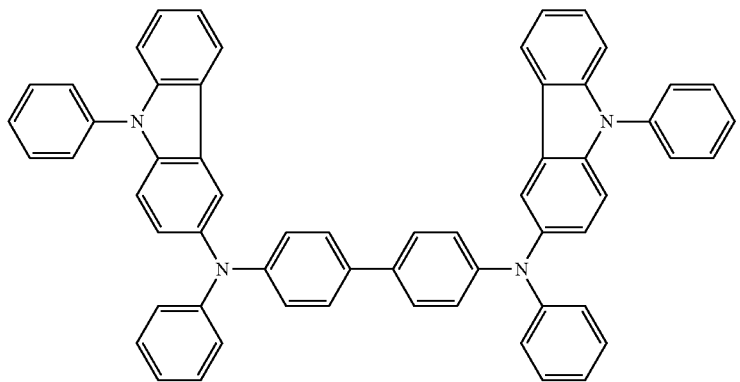
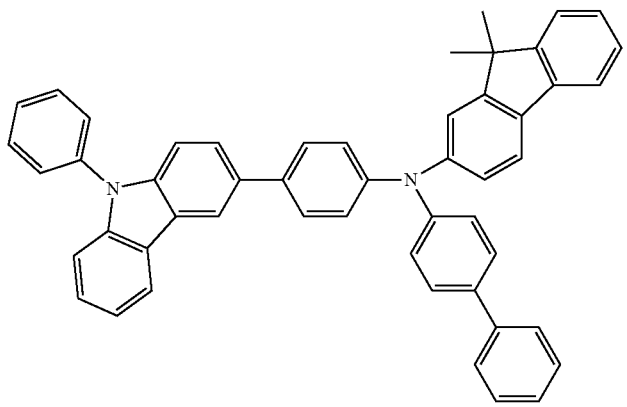

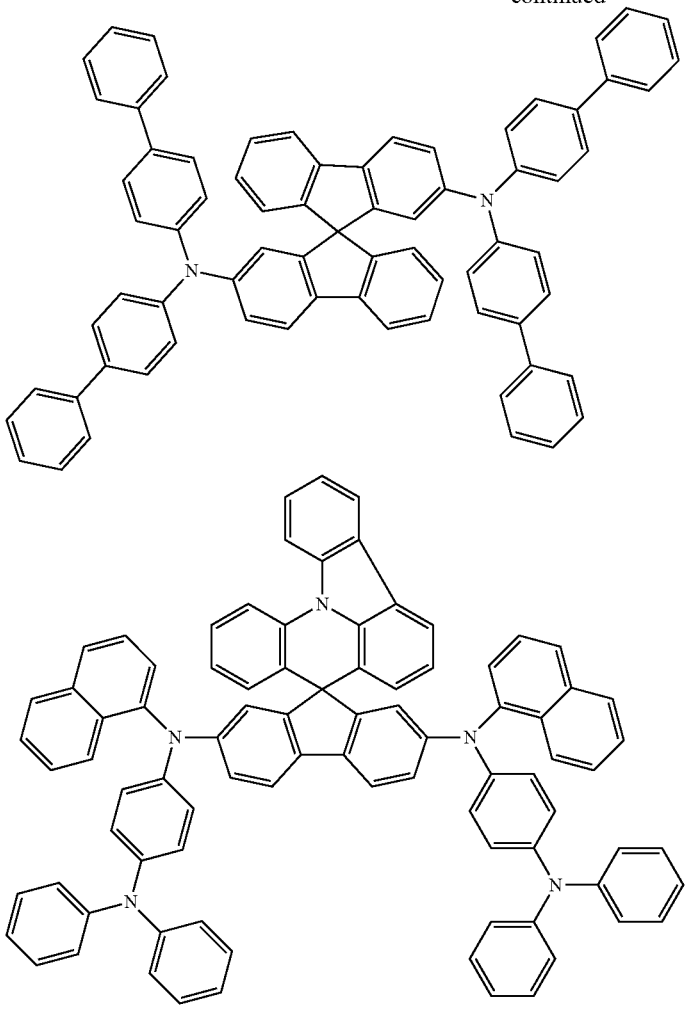

In an alternative, likewise preferred embodiment of the invention, the amine compound is selected from polymers, and among these preferably polymers containing arylamine groups, more preferably polymers containing triarylamine groups.

Preferred polymers containing triarylamine groups comprise at least one structural unit corresponding to the following formula (I):

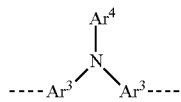

Formula (I)
where:
Ar$^3$, Ar$^4$ is the same or different at each instance and is an aromatic ring system which has 6 to 40 aromatic ring atoms and may be substituted by one or more R$^3$ radicals, or a heteroaromatic ring system which has 5 to 40 aromatic ring atoms and may be substituted by one or more R$^3$ radicals;
R$^3$ is the same or different at each instance and is selected from H, D, F, Cl, Br, I, B(OR$^4$)$_2$, C(=O)R$^1$, CN, Si(R$^4$)$_3$, N(R$^4$)$_2$, P(=O)(R$^1$)$_2$, OR$^4$, S(=O)R$^4$, S(=O)$_2$R$^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R$^3$ radicals may be joined to one another and may form a ring; where the alkyl, alkoxy, alkenyl and alkynyl groups mentioned and the aromatic ring systems and heteroaromatic ring systems mentioned may each be substituted by one or more R$^4$ radicals; and where one or more CH$_2$ groups in the alkyl, alkoxy, alkenyl and alkynyl groups mentioned may be replaced by —R$^4$C=CR$^4$—, —C≡C—, Si(R$^4$)$_2$, C=O, C=NR$^4$, —C(=O)O—, —C(=O)NR$^4$—, NR$^4$, P(=O)(R$^4$), —O—, —S—, SO or SO$_2$;
R$^4$ is the same or different at each instance and is selected from H, D, F, Cl, Br, I, CN, alkyl groups having 1 to 20 carbon atoms, aromatic ring systems having 6 to 40 aromatic ring atoms and heteroaromatic ring systems having 5 to 40 aromatic ring atoms; where two or more R$^4$ radicals may be joined to one another and may form a ring; and where the alkyl groups, aromatic ring systems and heteroaromatic ring systems mentioned may be substituted by F or CN; and the broken lines represent bonds to adjacent structural units in the polymer.

The term "structural unit" in the present application is understood to mean a unit which, proceeding from a monomer unit having at least two, preferably two, reactive groups, by a bond-forming reaction, is incorporated into the polymer base skeleton as a portion thereof and is present thus bonded as a repeat unit within the polymer prepared.

The polymeric compounds according to the invention have preferably 10 to 10 000, more preferably 10 to 5000 and most preferably 10 to 2000 structural units (i.e. repeat units). The oligomeric compounds according to the invention preferably have 3 to 9 structural units. The branching factor of the polymers is between 0 (linear polymer, no branching sites) and 1 (fully branched dendrimer).

The polymers usable in accordance with the invention preferably have a molecular weight $M_w$ in the range from 1000 to 2 000 000 g/mol, more preferably a molecular weight $M_w$ in the range from 10 000 to 1 500 000 g/mol and most preferably a molecular weight $M_w$ in the range from 50 000 to 1 000 000 g/mol. The molecular weight $M_w$ is determined by means of GPC(=gel permeation chromatography) against an internal polystyrene standard.

The polymers according to the invention are conjugated, semi-conjugated or non-conjugated polymers. Preference is given to conjugated or semi-conjugated polymers.

According to the invention, the structural units of the formula (I) may be incorporated into the main chain or side chain of the polymer. Preferably, however, the structural units of the formula (I) are incorporated into the main chain of the polymer. In the case of incorporation into the side chain of the polymer, the structural units of the formula (I) may either be mono- or bivalent, meaning that they have either one or two bonds to adjacent structural units in the polymer.

Preferably, the polymer according to the present invention is a copolymer, meaning that it contains a plurality of different structural units. The different structural units of the polymer may all correspond to the formula (I), or one or more structural units may correspond to a formula other than formula (I). Preferably, one or more structural units of the polymer correspond to a formula other than formula (I).

"Conjugated polymers" in the context of the present application are polymers containing mainly sp$^2$-hybridized (or else optionally sp-hybridized) carbon atoms in the main chain, which may also be replaced by correspondingly hybridized heteroatoms. In the simplest case, this means the alternating presence of double and single bonds in the main chain, but polymers having units such as a meta-bonded phenylene, for example, should also be regarded as conjugated polymers in the context of this application. "Mainly" means that defects that occur naturally (involuntarily) and lead to interrupted conjugation do not make the term "conjugated polymer" inapplicable. Conjugated polymers are likewise considered to be polymers having a conjugated main chain and non-conjugated side chains. In addition, the present application likewise refers to conjugation when, for example, arylamine units, arylphosphine units, particular heterocycles (i.e. conjugation via nitrogen, oxygen or sulphur atoms) and/or organometallic complexes (i.e. conjugation by the metal atom) are present in the main chain. The same applies to conjugated dendrimers. In contrast, units such as simple alkyl bridges, (thio)ether, ester, amide or imide linkages, for example, are unambiguously defined as non-conjugated segments.

A semi-conjugated polymer shall be understood in the present application to mean a polymer containing conjugated regions separated from one another by non-conjugated sections, deliberate conjugation breakers (for example spacer groups) or branches, for example in which comparatively long conjugated sections in the main chain are interrupted by non-conjugated sections, or which contains comparatively long conjugated sections in the side chains of a polymer non-conjugated in the main chain. Conjugated and semi-conjugated polymers may also contain conjugated, semi-conjugated or non-conjugated dendrimers.

The term "dendrimer" in the present application shall be understood to mean a highly branched compound formed from a multifunctional core to which branched monomers are bonded in a regular structure, such that a tree-like structure is obtained. In this case, both the core and the monomers may assume any desired branched structures consisting both of purely organic units and organometallic compounds or coordination compounds. "Dendrimeric" shall generally be understood here as described, for example, by M. Fischer and F. Vögtle (*Angew. Chem., Int. Ed.* 1999, 38, 885).

Preferred Ar$^4$ groups in formula (I) are as follows:

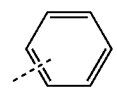

E1

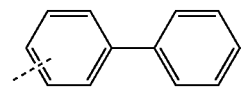

E2

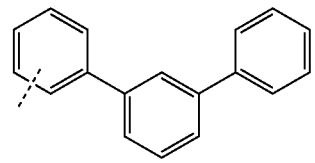

E3

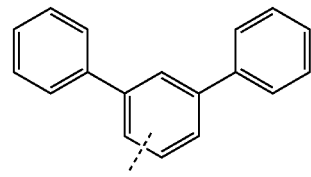

E4

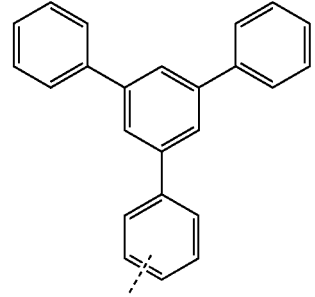

E5

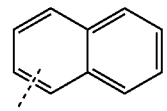

E6

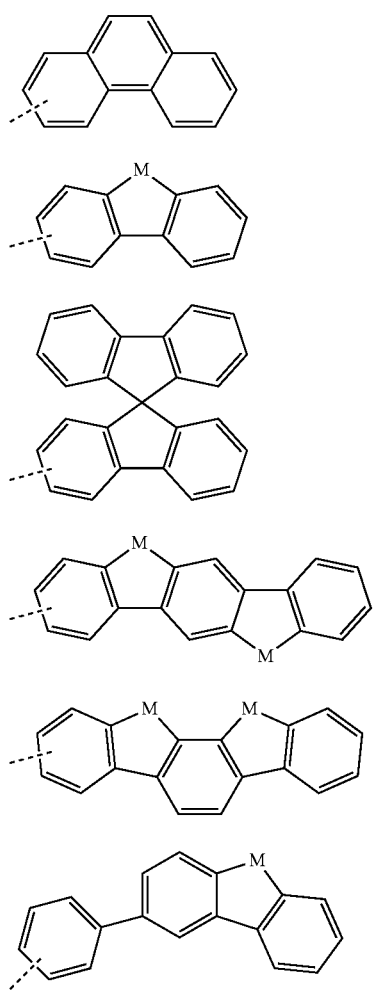
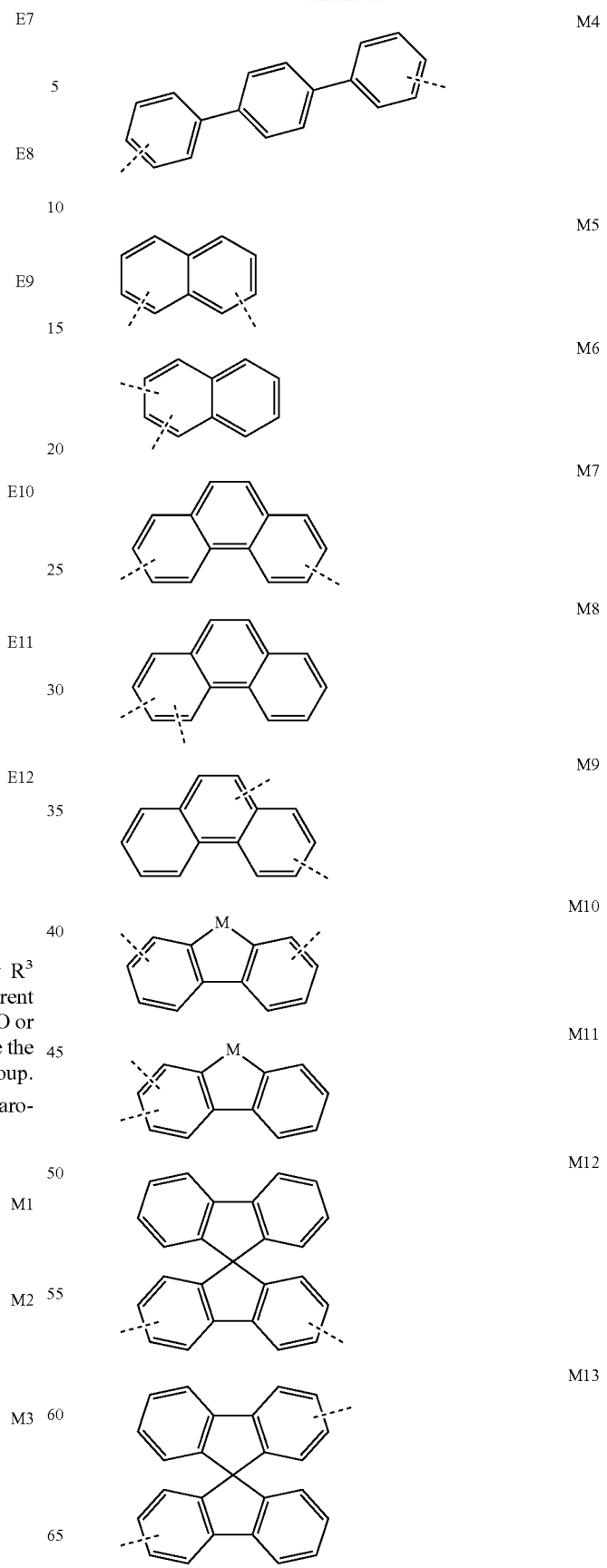

where the groups may optionally be substituted by $R^3$ radicals at any free position, where M is the same or different at each instance and is $C(R^3)_2$, $NR^3$, $Si(R^3)_2$, O, S, C=O or P=O, preferably $C(R^3)_2$, $Si(R^3)_2$, NR, O or S, and where the broken line represents the bonding site to the adjacent group.

Preferred mono- or polycyclic, aromatic or heteroaromatic $Ar^3$ groups in formula (I) are as follows:

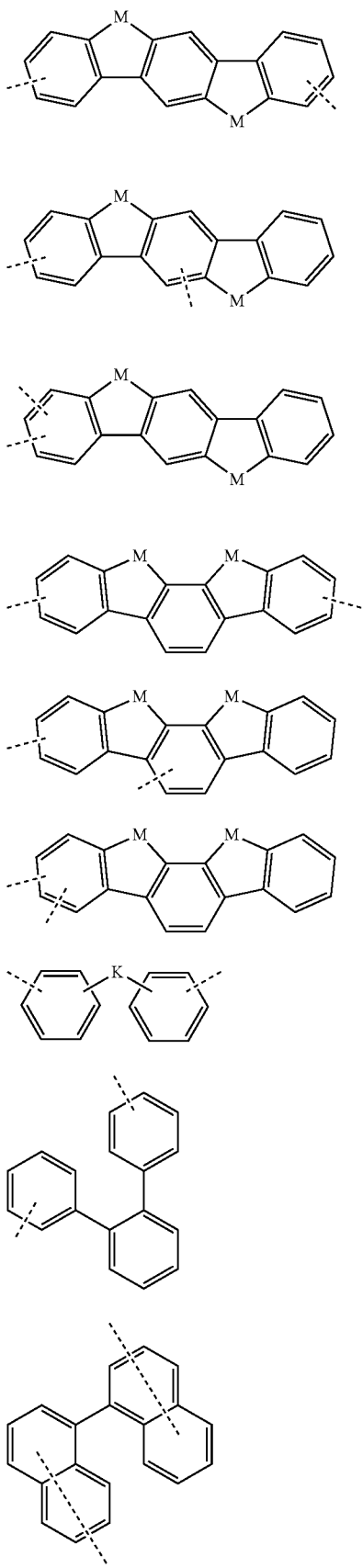

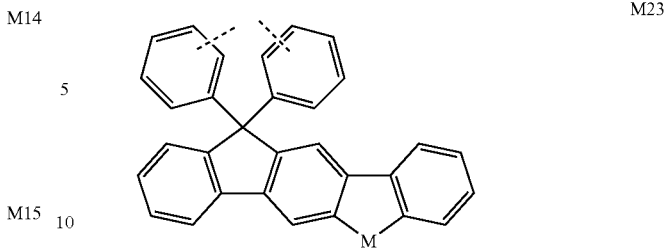

where the groups may optionally be substituted by R³ radicals at any free position, where M is the same or different at each instance and is C(R³)₂, NR³, Si(R³)₂, O, S, C=O or P=O, preferably C(R³)₂, Si(R³)₂, NR, O or S, where K is C(R³)₂, Si(R³)₂, NR³, O, S, a straight-chain alkyl or alkoxy group having 1 to 20 carbon atoms, a branched or cyclic alkyl or alkoxy group having 3 to 20 carbon atoms, an alkenyl or alkynyl group having 2 to 20 carbon atoms, an aromatic ring system having 6 to 40 aromatic ring atoms, or a heteroaromatic ring system having 5 to 40 aromatic ring atoms; where the alkyl, alkoxy, alkenyl and alkynyl groups mentioned and the aromatic ring systems and heteroaromatic ring systems mentioned may each be substituted by one or more R³ radicals; and where one or more CH₂ groups in the alkyl, alkoxy, alkenyl and alkynyl groups mentioned may be replaced by —R³C=CR³—, —C≡C—, Si(R³)₂, C=O, C=NR³, —C(=O)O—, —C(=O)NR³—, NR³, P(=O) (R³), —O—, —S—, SO or SO₂, and where the broken lines represent the bonding sites to the adjacent groups.

It is preferable in accordance with the invention that at least one of the structural units of the formula (I) has at least one crosslinkable Q group.

"Crosslinkable Q group" in the context of the present invention means a functional group capable of entering into a reaction and thus forming an insoluble compound. The reaction may be with a further identical Q group, a further different Q group or any other portion of the same or another polymer chain. The crosslinkable group is thus a reactive group. This affords, as a result of the reaction of the crosslinkable group, a correspondingly crosslinked compound. The chemical reaction can also be conducted in the layer, giving rise to an insoluble layer. The crosslinking can usually be promoted by means of heat or by means of UV radiation, microwave radiation, x-radiation or electron beams, optionally in the presence of an initiator. "Insoluble" in the context of the present invention preferably means that the polymer according to the invention, after the crosslinking reaction, i.e. after the reaction of the crosslinkable groups, has a lower solubility at room temperature in an organic solvent by at least a factor of 3, preferably at least a factor of 10, than that of the corresponding non-crosslinked polymer according to the invention in the same organic solvent.

At least one crosslinkable group in the present application means that a structural unit has one or more crosslinkable groups. Preferably, a structural unit has exactly one crosslinkable group.

If the structural unit of the formula (I) has a crosslinkable group, it may be bonded to $Ar^3$ or $Ar^4$. Preferably, the crosslinkable group is bonded to $Ar^4$.

Q groups used may generally be any groups known for the purpose to the person skilled in the art. The particular function of this group is to join the polymeric compounds according to the invention to one another by a crosslinking reaction, optionally with further reactive polymeric compounds. This leads to a crosslinked compound or, when the reaction is conducted in a layer, to a crosslinked layer. A crosslinked layer in the context of the present invention is understood to mean a layer obtainable by conducting the crosslinking reaction from a layer of the crosslinkable polymeric compound according to the invention. The crosslinking reaction can generally be initiated by means of heat and/or by means of UV radiation, microwave radiation, x-radiation or electron beams and/or by the use of free-radical formers, anions, cations, acids and/or photoacids. The presence of catalysts may likewise be advisable or necessary. Preferably, the crosslinking reaction is a reaction for which no initiator and no catalyst need be added.

Crosslinkable Q groups preferred in accordance with the invention are the following groups:
a) Terminal or cyclic alkenyl or terminal dienyl and alkynyl groups:
   Suitable units are those which contain a terminal or cyclic double bond, a terminal dienyl group or a terminal triple bond, especially terminal or cyclic alkenyl, terminal dienyl or terminal alkynyl groups having 2 to 40 carbon atoms, preferably having 2 to 10 carbon atoms, where individual $CH_2$ groups and/or individual hydrogen atoms may also be replaced by the abovementioned R groups. Additionally suitable are also groups which are to be regarded as precursors and which are capable of in situ formation of a double or triple bond.
b) Alkenyloxy, dienyloxy or alkynyloxy groups:
   Additionally suitable are alkenyloxy, dienyloxy or alkynyloxy groups, preferably alkenyloxy groups.
c) Acrylic acid groups:
   Additionally suitable are acrylic acid units in the broadest sense, preferably acrylic esters, acrylamides, methacrylic esters and methacrylamides. Particular preference is given to $C_{1-10}$-alkyl acrylate and $C_{1-10}$-alkyl methacrylate.
   The crosslinking reaction of the groups mentioned above under a) to c) can be effected via a free-radical, cationic or anionic mechanism, or else via cycloaddition.
   It may be advisable to add an appropriate initiator for the crosslinking reaction. Suitable initiators for the free-radical crosslinking are, for example, dibenzoyl peroxide, AIBN or TEMPO. Suitable initiators for the cationic crosslinking are, for example, $AlCl_3$, $BF_3$, triphenylmethyl perchlorate or tropylium hexachloroantimonate. Suitable initiators for the anionic crosslinking are bases, especially butyllithium.
   In a preferred embodiment of the present invention, the crosslinking, however, is conducted without the addition of an initiator and is initiated exclusively by thermal means. The reason for this preference is that the absence of the initiator prevents contamination of the layer which could lead to worsening of the device properties.
d) Oxetanes and oxiranes:
   A further suitable class of crosslinkable Q groups is that of oxetanes and oxiranes which crosslink cationically via ring opening.
   It may be advisable to add an appropriate initiator for the crosslinking reaction. Suitable initiators are, for example, $AlCl_3$, $BF_3$, triphenylmethyl perchlorate or tropylium hexachloroantimonate. It is likewise possible to add photoacids as initiators.
e) Silanes:
   Additionally suitable as a class of crosslinkable groups are silane groups $SiR_3$ where at least two R groups, preferably all three R groups, are Cl or an alkoxy group having 1 to 20 carbon atoms.
   This group reacts in the presence of water to give an oligo- or polysiloxane.
f) Cyclobutane groups
   The abovementioned crosslinkable Q groups are generally known to those skilled in the art, as are the suitable reaction conditions which are used for reaction of these groups.

The proportion of structural units of the formulae (I) in the polymer is in the range from 1 to 100 mol %, preferably in the range from 25 to 100 mol %, more preferably in the range from 50 to 95 mol %, based on 100 mol % of all the copolymerized monomers present as structural units in the polymer.

Preferably, the polymer comprises at least one further structural unit of the following formula (II) which is different from the structural unit of the formula (I):

Formula (II)

where $Ar^5$ is an aromatic ring system which has 6 to 40 aromatic ring atoms and may be substituted by one or more $R^3$ radicals, or a heteroaromatic ring system which has 5 to 40 aromatic ring atoms and may be substituted by one or more $R^3$ radicals, where $R^3$ is as defined in formula (I).

Preferred $Ar^5$ groups correspond to the abovementioned M1 to M23 groups. In a particularly preferred embodiment, $Ar^5$ is selected from indenofluorenes.

Particularly preferred amine polymers for use as amine compound in the layer applied from solution according to the present invention are as follows:

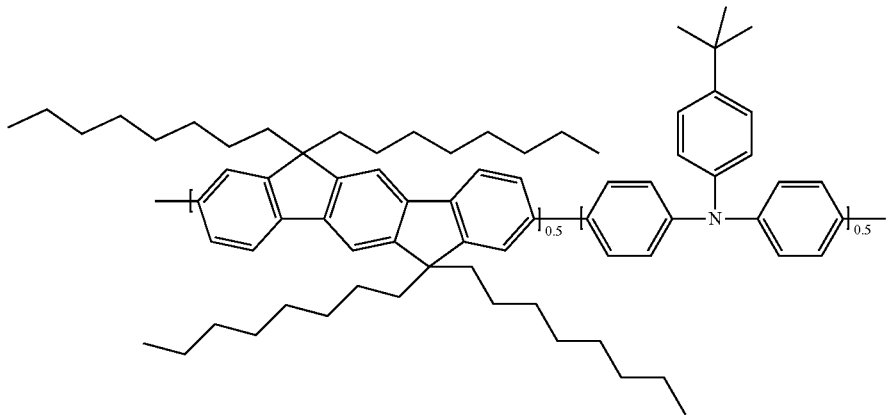

P-1

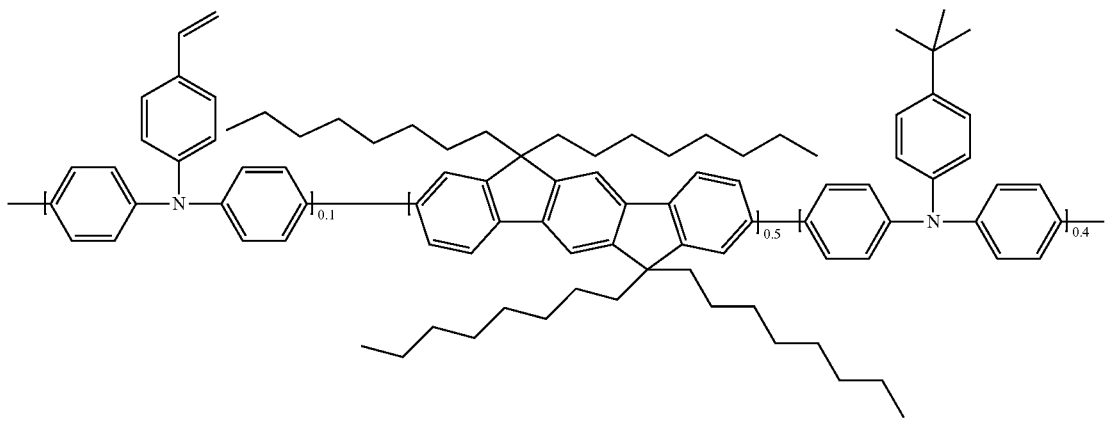

P-2

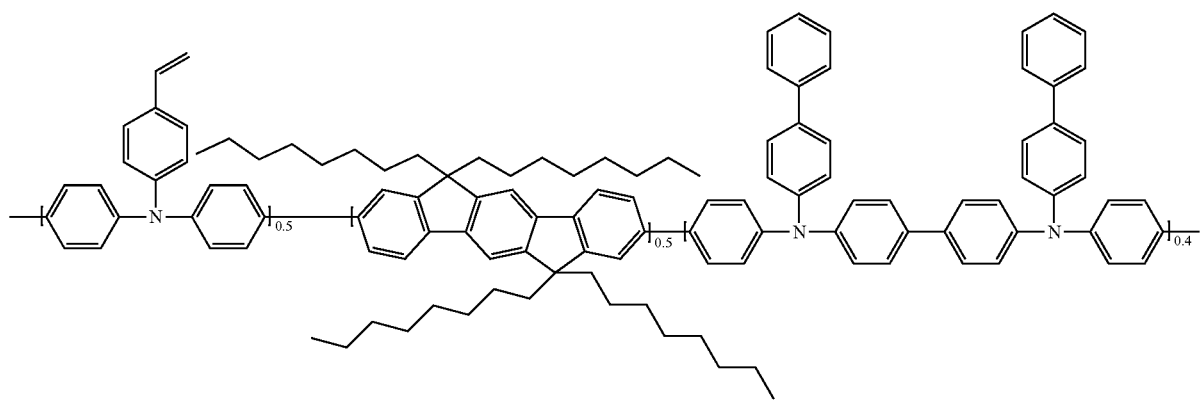

P-3

Preferably, the amine polymer for use as amine compound in the layer applied from solution is not the abovementioned P-3.

The polymers usable in accordance with the invention are generally prepared by polymerization of one or more monomer types, of which at least one monomer in the polymer leads to structural units of the formula (I) and/or (II). Suitable polymerization reactions are known to those skilled in the art and are described in the literature. Particularly suitable and preferred polymerization reactions which lead to C-C and C—N bonds are as follows:

(A) SUZUKI polymerization;
(B) YAMAMOTO polymerization;
(C) STILLE polymerization;
(D) HECK polymerization;
(E) NEGISHI polymerization;
(F) SONOGASHIRA polymerization;
(G) HIYAMA polymerization; and
(H) HARTWIG-BUCHWALD polymerization.

How the polymerization can be conducted by these methods and how the polymers can then be separated from the reaction medium and purified is known to those skilled in the art and is described in detail in the literature, for example in WO 03/048225 A2, WO 2004/037887 A2 and WO 2004/037887 A2. The C—C couplings are preferably selected from the groups of SUZUKI coupling, YAMAMOTO coupling and STILLE coupling; the C—N coupling is preferably a coupling according to HARTWIG-BUCHWALD.

According to the invention, the layer which is disposed between the anode and emitting layer and comprises an amine compound has been applied from solution. The application from solution is preferably effected by spin-coating, or by any printing method, for example screen printing, flexographic printing, nozzle printing or offset printing, but more preferably by LITI (light-induced thermal imaging, thermal transfer printing) or inkjet printing.

For this purpose, a formulation comprising the amine compound and at least one solvent is required.

For production of the formulation, the amine compound and any further compounds present in the layer are dissolved in a suitable solvent.

For this purpose, the individual components of the formulation are preferably mixed and stirred, optionally also with supply of heat. Frequently, the formulation is also degassed or produced with solvents oversaturated with inert gases. Overall, it should be ensured that only solvents and other components of very high purity are used, in order to avoid contamination of the electronic devices with damaging compounds. More particularly, it should be ensured that the water, oxygen and halogen content in the formulation is kept low, since the performance data of organic electroluminescent devices in particular can be greatly impaired by the presence thereof.

A single solvent or a plurality of solvents may be present in the formulation used.

Preferably in accordance with the invention, the solvents are selected from solvents having a surface tension of at least 28 mN/m, preferably at least 30 mN/m, very preferably at least 32 mN/m and even more preferably at least 35 mN/m.

It is further preferable when the boiling or sublimation temperature of the solvents used is less than 300° C. and preferably less than 260° C.

It is very preferable when the viscosity of the solvents is greater than 3 mPa*s and preferably greater than 5 mPa*s.

It is further preferable when the molecular weight of the solvents is less than or equal to 1000 g/mol, preferably less than or equal to 700 g/mol, very preferably less than or equal to 500 g/mol and especially preferably less than or equal to 300 g/mol.

Preferably, the concentration of the amine compound in the formulation, based on the overall formulation, is in the range from 0.5% to 20% by weight, more preferably in the range from 1% to 15% by weight and even more preferably in the range from 1.5% to 10% by weight. For the application of the formulation by means of spin-coating, it is preferable that the concentration of the amine compound in the formulation, based on the overall formulation, is in the range from 0.5% to 5% by weight, more preferably in the range from 1% to 4% by weight.

Preferred solvents are selected from aromatic solvents. Particularly preferred solvents are selected from aromatic hydrocarbons such as toluene, o-, m- or p-xylene, phenoxytoluene, trimethylbenzenes (e.g. 1,2,3-, 1,2,4- and 1,3,5-trimethylbenzene), tetralin, other mono-, di-, tri- and tetraalkylbenzenes (e.g. diethylbenzene, methylcumene, tetramethylbenzenes), aromatic ethers (e.g. anisole, alkylanisoles, e.g. 2, 3 and 4 isomers of methylanisole, 2,3, 2,4, 2,5, 2,6, 3,4 and 3,5 isomers of dimethylanisole), naphthalene derivatives, alkylnaphthalene derivatives (e.g. 1- and 2-methylnaphthalene), and di- and tetrahydronaphthalene derivatives. Likewise preferred are aromatic esters (e.g. alkyl benzoates, aromatic ketones (e.g. acetophenone, propiophenone), alkyl ketones (e.g. cyclohexanone), heteroaromatic solvents (e.g. thiophene, mono-, di- and trialkylthiophenes, 2-alkylthiazoles, benzothiazoles, etc., pyridines), haloarylenes and aniline derivatives. These solvents may contain halogen atoms.

Particularly preferred solvents are aromatic hydrocarbons, especially toluene, phenoxytoluene, dimethylbenzenes (xylenes), trimethylbenzenes, tetralin and methylnaphthalenes, aromatic ethers, especially anisole, and aromatic esters, especially methyl benzoate. Even more preferred are aromatic ethers, especially anisole and derivatives thereof, such as alkylanisoles, and aromatic esters, especially methyl benzoate.

Explicit examples of preferred solvents are toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The inventive device preferably comprises additional layers in addition to the cathode, anode, emitting layer and at least one layer disposed between the anode and emitting layer.

These additional layers are preferably selected from buffer layers, hole injection layers, hole transport layers, hole blocker layers, electron transport layers, electron injection layers, electron blocker layers, exciton blocker layers, interlayers, charge generation layers and/or organic or inorganic p/n junctions. The function and preferred arrangement of these layers are known to those skilled in the art. Additionally known to those skilled in the art are possible compounds for use in the particular layers.

The layers of the inventive device preferably comprise one or more organic compounds. They are more preferably formed essentially from organic compounds, i.e. are organic layers.

Materials used in the layers may be any customarily used in the layers in question according to the prior art.

The sequence of layers in the inventive device is preferably as follows, anode
    optional buffer layer
    layer which comprises an amine compound and has been applied from solution
    optionally further hole transport layers
    optionally electron blocker layer
    emitting layer
    optionally hole blocker layer
    electron transport layer
    optionally further electron transport layers
    optionally electron injection layer
    cathode.

It is additionally possible for further layers to be present in the inventive device.

Preferably, the inventive device does not comprise the following layer sequence:

substrate anode of ITO buffer layer comprising PEDOT:PSS

HTL comprising the abovementioned polymer P-3, applied from solution emitting layer comprising the compounds

IC2

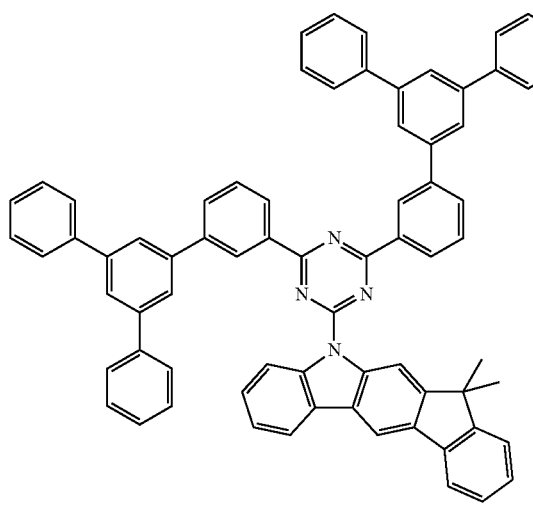

WB1

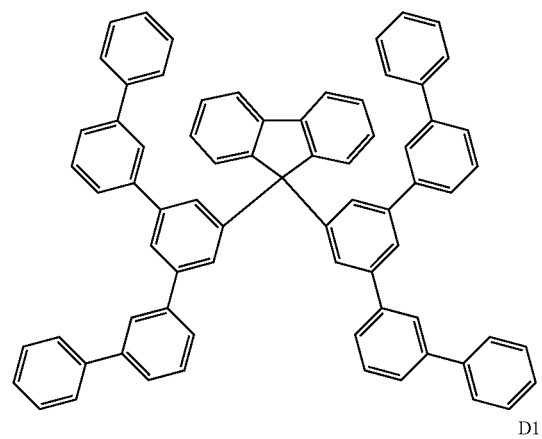

D1

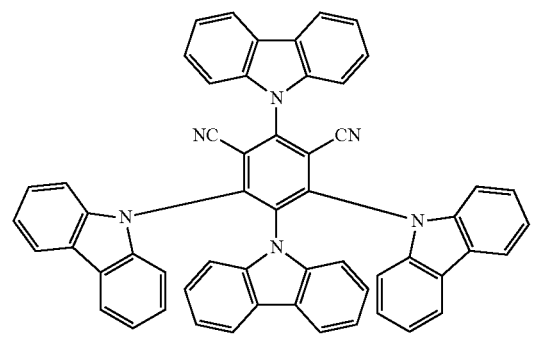

electron transport layer comprising the compound ST1

ST1

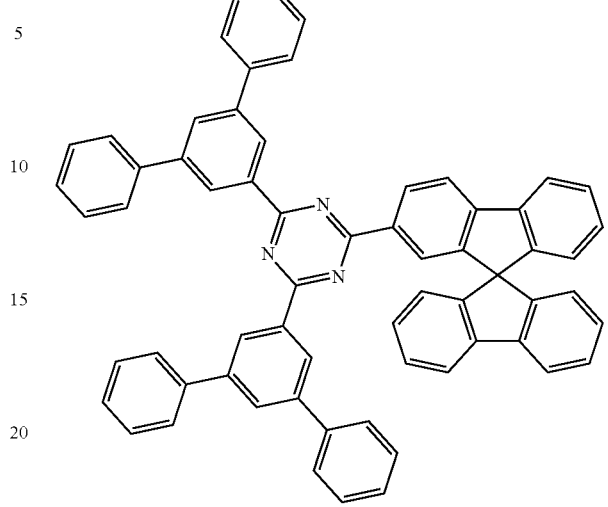

electron injection layer comprising the compounds ST1 and LiQ

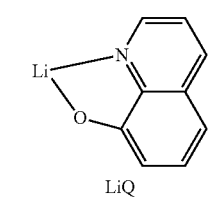

LiQ cathode of aluminium.

Preferably, the inventive device comprises a buffer layer between the anode and the layer that has been applied from solution. This buffer layer preferably comprises a conductive organic polymer, more preferably PEDOT:PSS or PANI (polyaniline). This improves the hole injection and hence the performance data of the OLED. In addition, this increases the reliability, and especially reduces the failure frequency.

In an alternative embodiment which is likewise preferred under particular circumstances, the layer which comprises an amine compound and has been applied from solution is applied to the anode directly, i.e. without an intervening layer. This gives, to an exceptional degree, the advantage of a smoothed surface of the layer comprising an amine compound.

Preferably, the inventive device comprises exactly one emitting layer. However, it is also possible for a plurality of emitting layers to be present, which is of particular interest when the device is to be used as a lighting device. When the inventive device comprises a plurality of emitting layers, the layer which has been applied from solution and comprises an amine compound is preferably disposed between the anode and the closest of the plurality of emitting layers to the anode.

In a preferred embodiment, the hole transport layers are p-doped and/or the electron transport layers are n-doped. A p-doped layer is understood to mean a layer in which a compound present in a small amount (a p-dopant) generates free holes and the conductivity thereof is increased as a result. An n-doped layer is understood to mean a layer in which a compound present in a small amount (an n-dopant) generates free electrons and the conductivity thereof is increased as a result. A comprehensive discussion of doped transport layers in OLEDs can be found in Chem. Rev. 2007, 107, 1233. More preferably, the p-dopant is capable of oxidizing the hole transport material in the hole transport layer, i.e. has a sufficiently high redox potential, especially a higher redox potential than the hole transport material. Suitable p-dopants are in principle any compounds which are electron acceptor compounds and which can increase the conductivity of the organic layer by oxidizing the hole transport material. The person skilled in the art, in the context of his common knowledge in the art, is able to identify suitable compounds without any great effort. The same applies mutatis mutandis to n-dopants.

Preferred cathodes of the organic electroluminescent device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. On the other hand, metal/metal oxide electrodes (e.g. Al/Ni/$NiO_x$, Al/$PtO_x$) may also be preferred. For some applications, at least one of the electrodes has to be transparent or partly transparent in order to enable the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

Preferably, the organic electroluminescent device is used in displays, as a light source in lighting applications and as a light source in medical and/or cosmetic applications (for example in light therapy).

The present application also provides a process for producing an organic electroluminescent device comprising
anode,
cathode,
an emitting layer comprising an emitting compound having a difference between the energies of its $S_1$ and $T_1$ states of not more than 0.15 eV, and
a layer which is disposed between the anode and emitting layer and comprises an amine compound, where the energies of the $S_1$ and $T_1$ states of the emitting compound are determined as specified in the working examples and where the layer which is disposed between the anode and emitting layer and comprises an amine compound has been applied from solution.

For this process, the above-specified preferred embodiments of the device apply correspondingly.

In the application of layers of organic electroluminescent devices, a distinction is made between two fundamentally different methods. In the first method, the relevant compounds are applied by vapour deposition under reduced pressure (gas phase deposition). This method is very inconvenient and costly. However, the performance data of the OLEDs obtained by such methods are typically very good. In the second method, the relevant compounds are applied from solution, as is the case in the inventive device for the layer which is disposed between the anode and emitting layer and comprises an amino compound. The solution-based method has the potential of being very cost-efficient. In addition, the failure rate of the OLEDs obtained, in relative terms, is often lower. However, the performance data of the OLEDs obtained are often less good than in the case of OLEDs where the layers have been produced from solution. Surprisingly, however, it has been found in the present invention that, in the given case, the combination of solution-based application of layers and gas phase-based application of layers results in occurrence of the advantages of both methods, while the disadvantages occur only to a negligible degree. More particularly, the devices obtained have very low failure rates combined with very good performance data.

In a preferred embodiment, apart from the layer which is disposed between the anode and emitting layer and is applied from solution, one or more layers of the organic electroluminescent device are applied from the gas phase.

It is preferable here that all the layers between the anode and emitting layer are applied from solution, and that all the layers between the emitting layer and the cathode are applied from the gas phase. It is particularly preferable here that all the layers between the anode and emitting layer are applied from solution, and that the emitting layer and all the layers between the emitting layer and the cathode are applied from the gas phase. More particularly, it is preferable that the one or more emitting layers are applied from the gas phase, especially that emitting layer comprising an emitting compound having a magnitude of the difference between the energies of its $S_1$ and $T_1$ states of not more than 0.15 eV.

It is preferable that the emitting layer comprising an emitting compound having a magnitude of the difference between the energies of its $S_1$ and $T_1$ states of not more than 0.15 eV is not applied from toluene solution and is preferably not applied from solution at all.

If layers are applied from the gas phase, it is preferable that the materials are applied by vapour deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar. Alternatives to the abovementioned sublimation method are the OVPD (organic vapour phase deposition) method or carrier gas sublimation.

The device is finally structured (according to the application), contact-connected and finally sealed, in order to rule out damaging effects by water and air, especially oxygen.

All the above-specified preferred embodiments relating to the inventive device apply, where applicable, as preferred embodiments to the inventive production process as well.

The working examples which follow serve to further illustrate the invention and its technical effects and should not be interpreted in a restrictive manner.

WORKING EXAMPLES

A) Production and Characterization of OLEDs

A-1) Production of the OLEDs

In the examples which follow, the data for various OLEDs are presented.

Cleaned glass plaques (cleaning in Miele laboratory glass washer, Merck Extran detergent) coated with structured ITO (indium tin oxide) of thickness 50 nm are pretreated with UV ozone for 25 minutes (UVP PR-100 UV ozone generator). These glass plaques form the substrates to which the OLEDs are applied. After the UV ozone treatment, the substrates are processed further within 30 min.

A-2) Characterization of the OLEDs

The OLEDs are characterized in a standard manner. For this purpose, the electroluminescence spectra, voltage and external quantum efficiency (EQE, measured in percent) are determined. The EQE is calculated from the current efficiency (in cd/A) in forward direction, assuming Lambertian radiation characteristics. The current efficiency is determined from luminance and current density. The luminance is measured with a calibrated photodiode. The electroluminescence spectra are determined at a luminance of 1000 cd/m$^2$, and the CIE 1931 x and y colour coordinates are calculated therefrom. The parameter U1000 refers to the voltage which is required for a luminance of 1000 cd/m$^2$. EQE1000 refers to the external quantum efficiency at an operating luminance of 1000 cd/m$^2$.

Example 1

The substrate is coated with 20 nm of PEDOT:PSS (poly(3,4-ethylenedioxythiophene) poly(styrenesulphonate), purchased as CLEVIOS™ P VP AI 4083 from Heraeus Precious Metals GmbH Deutschland, spun on from aqueous solution) and then baked at 180° C. for 10 min.

Subsequently, the following layers are applied by thermal vapour deposition in a vacuum chamber in the sequence specified: a 15 nm-thick emission layer consisting to an extent of 85% by volume of substance IC1 and to an extent of 15% by volume of substance D1, a 10 nm-thick layer of substance IC1, a 40 nm-thick layer of substance ST1, a 3 nm-thick layer of substance LiQ, a 100 nm-thick layer of aluminium as cathode.

Subsequently, the OLEDs are encapsulated.

The emission layer exhibits a PLQE of 81% (excitation wavelength 350 nm) and a decay time of $t_a$=4.8 µs ($t_d$=7 µs). These values also apply to Example 2 and Inventive Examples 1-4.

64 of these OLEDs are produced. If they are operated at a current density of 20 mA/cm$^2$, six (i.e. about 9%) of them fail after operation for 200 h. The OLEDs exhibit CIE x,y colour coordinates of 0.32/0.56, EQE1000=8.4%, U1000=3.6 V.

Example 2

A 20 nm-thick hole transport layer of the material SpMA1 is applied to the substrate by thermal evaporation in a vacuum chamber.

The same layers as in Example 1 are applied thereto by vacuum evaporation (15 nm layer having 85% by volume of IC1 and 15% by volume of D1, 10 nm of IC1, 40 nm of ST1, 3 nm of LiQ, 100 nm of aluminium).

Subsequently, the OLEDs are encapsulated.

64 of these OLEDs are produced. If they are operated at a current density of 20 mA/cm$^2$, 17 (i.e. about 27%) of them fail after operation for 200 h. The OLEDs exhibit CIE x,y colour coordinates of 0.34/0.58, EQE1000=12.8%, U1000=3.3 V.

Inventive Example 1

A crosslinkable hole transport layer is applied to the substrate. It consists of a polymer of the following structural formula:

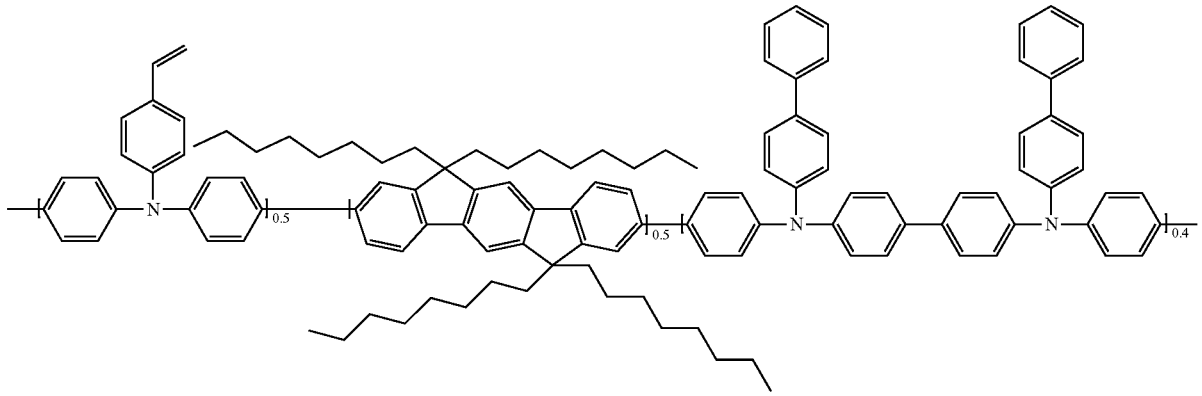

which has been synthesized according to WO 2010/097155. The material is dissolved in toluene. The solids content of the solution is 5 g/l. The layer is spun on in an inert gas atmosphere, argon in the present case, and baked at 180° C. for 60 minutes. The layer thickness is 20 nm.

The same layers as in Example 1 are applied thereto by vacuum evaporation (15 nm layer having 85% by volume of IC1 and 15% by volume of D1, 10 nm of IC1, 40 nm of ST1, 3 nm of LiQ, 100 nm of aluminium).

Subsequently, the OLEDs are encapsulated.

64 of these OLEDs are produced. If they are operated at a current density of 20 mA/cm$^2$, five (i.e. about 8%) of them fail after operation for 200 h, i.e. a comparable number to that in Example 1 and much fewer than in Example 2. The OLEDs exhibit CIE x,y colour coordinates of 0.34/0.59, EQE1000=12.2%, U1000=3.4 V. The performance data are thus much better than in Example 1 and comparable with Example 2.

Inventive Example 2

A hole transport layer is applied to the substrate. It consists of the material SpMA1. The material is dissolved in toluene. The solids content of the solution is 10 g/l. The layer is spun on in an inert gas atmosphere, argon in the present case, and baked at 1500° C. for 10 minutes. The layer thickness is 20 nm.

The same layers as in Example 1 are applied thereto by vacuum evaporation (15 nm layer having 85% by volume of IC1 and 15% by volume of D1, 10 nm of IC1, 40 nm of ST1, 3 nm of LiQ, 100 nm of aluminium).

Subsequently, the OLEDs are encapsulated.

64 of these OLEDs are produced. If they are operated at a current density of 20 mA/cm², nine (i.e. about 14%) of them fail after operation for 200 h, i.e. a comparable number to that in Example 1 and much fewer than in Example 2. The OLEDs exhibit CIE x,y colour coordinates of 0.34/0.58, EQE1000=13.1%, U1000=3.2 V. The performance data are thus much better than in Example 1 and comparable with Example 2.

Inventive Example 3

The OLED corresponds to Inventive Example 1, except that there is a 20 nm-thick PEDOT:PSS layer between the substrate and hole transport layer, which is applied according to Example 1.

64 of these OLEDs are produced. If they are operated at a current density of 20 mA/cm², two (i.e. about 3%) of them fail after operation for 200 h, i.e. much fewer than in Examples 1 and 2. The OLEDs exhibit CIE x,y colour coordinates of 0.33/0.58, EQE1000=13.6%, U1000=3.3 V. The performance data are thus much better than in Example 1 and somewhat better than in Example 2.

Inventive Example 4

The OLED corresponds to Inventive Example 2, except that there is a 20 nm-thick PEDOT:PSS layer between the substrate and hole transport layer, which is applied according to Example 1.

64 of these OLEDs are produced. If they are operated at a current density of 20 mA/cm², three (i.e. about 5%) of them fail after operation for 200 h, i.e. much fewer than in Examples 1 and 2. The OLEDs exhibit CIE x,y colour coordinates of 0.34/0.58, EQE1000=14.3%, U1000=3.1 V. The performance data are thus much better than in Example 1 and somewhat better than in Example 2.

TABLE 1

Structural formulae of the materials for the OLEDs

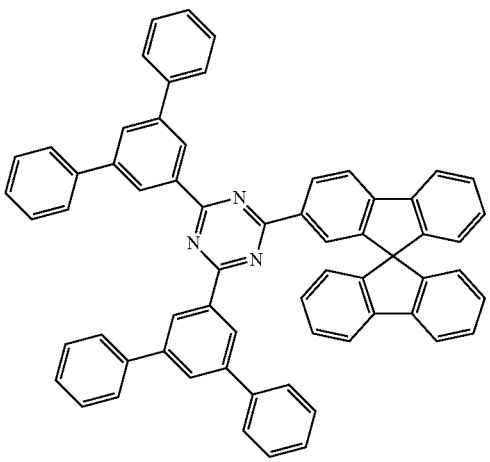 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]

ST1

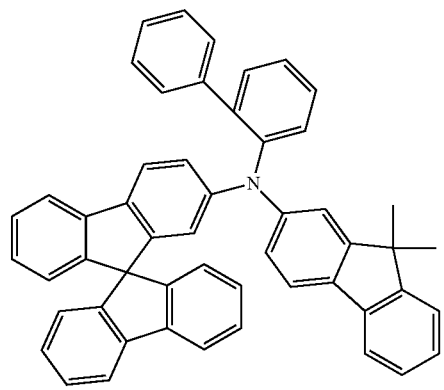 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

SpMA1

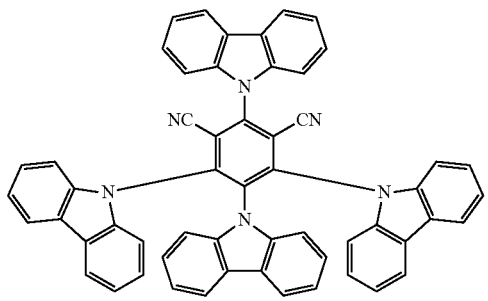 [SMILES: N#Cc1c(-n2c3ccccc3c3ccccc32)c(C#N)c(-n2c3ccccc3c3ccccc32)c(-n2c3ccccc3c3ccccc32)c1-n1c2ccccc2c2ccccc21]

D1

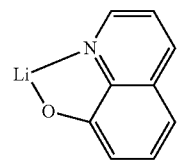

LiQ

TABLE 1-continued

Structural formulae of the materials for the OLEDs

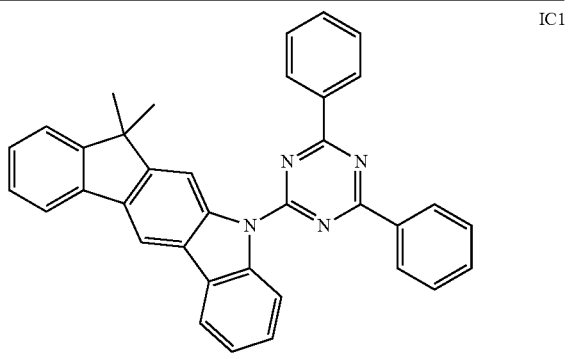

IC1

B) Method for Determining Measurements Used (Parameters)

B-1) Quantum-Chemical Method for Determining Orbital Energies and Electronic States The HOMO and LUMO energies and the triplet level and singlet levels of the materials are determined via quantum-chemical calculations. For this purpose, in the present case, the "Gaussian09, Revision D.01" software package (Gaussian Inc.) is used. For calculation of organic substances without metals (referred to as the "org." method), a geometry optimization is first conducted by the semi-empirical method AM1 (Gaussian input line "# AM1 opt") with charge 0 and multiplicity 1. Subsequently, on the basis of the optimized geometry, a single-point energy calculation is effected for the electronic ground state and the triplet level. This is done using the TDDFT (time dependent density functional theory) method B3PW91 with the 6-31G(d) basis set (Gaussian input line "# B3PW91/6-31G(d) td=(50-50, nstates=4)") (charge 0, multiplicity 1). For organometallic compounds (referred to as the "M-org." method), the geometry is optimized by the Hartree-Fock method and the LanL2MB basis set (Gaussian input line "#HF/LanL2MB opt") (charge 0, multiplicity 1). The energy calculation is effected, as described above, analogously to that for the organic substances, except that the "LanL2DZ" basis set is used for the metal atom and the "6-31G(d)" basis set for the ligands (Gaussian input line "#B3PW91/gen pseudo=lanl2 td=(50-50,nstates=4)"). From the energy calculation, the HOMO is obtained as the last orbital occupied by two electrons (alpha occ. eigenvalues) and LUMO as the first unoccupied orbital (alpha virt. eigenvalues) in Hartree units, where HEh and LEh represent the HOMO energy in Hartree units and the LUMO energy in Hartree units respectively. This is used to determine the HOMO and LUMO value in electron volts, calibrated by cyclic voltammetry measurements, as follows:

$$HOMO(eV)=((HEh*27.212)-0.9899)/1.1206$$

$$LUMO(eV)=((LEh*27.212)-2.0041)/1.385$$

These values are to be regarded as HOMO and as LUMO of the materials in the context of this application.

The triplet level $T_1$ of a material is defined as the relative excitation energy (in eV) of the triplet state having the lowest energy which is found by the quantum-chemical energy calculation.

The singlet level $S_1$ of a material is defined as the relative excitation energy (in eV) of the singlet state having the second-lowest energy which is found by the quantum-chemical energy calculation.

The energetically lowest singlet state is referred to as $S_0$.

The method described herein is independent of the software package used and always gives the same results. Examples of frequently utilized programs for this purpose are "Gaussian09" (Gaussian Inc.) and Q-Chem 4.1 (Q-Chem, Inc.). In the present case, the energies are calculated using the software package "Gaussian09, Revision D.01".

Table 2 states the HOMO and LUMO energy levels and $S_1$ and $T_1$ of the various materials. Table 1 shows the structural formulae of the materials used.

TABLE 2

HOMO, LUMO, $T_1$, $S_1$ of the materials

| Material | Method | HOMO (eV) | LUMO (eV) | $S_1$ (eV) | $T_1$ (eV) |
|---|---|---|---|---|---|
| D1 | org. | −6.11 | −3.40 | 2.50 | 2.41 |
| IC1 | org. | −5.79 | −2.83 | 3.09 | 2.69 |
| SpMA1 | org. | −5.25 | −2.18 | 3.34 | 2.58 |
| ST1 | org. | −6.03 | −2.82 | 3.32 | 2.68 |
| LiQ | M-org. | −5.17 | −2.39 | 2.85 | 2.13 |

B-2) Determination of Photoluminescence Quantum Efficiency (PLQE)

A 50 nm-thick film of the emission layers used in the different OLEDs is applied to a suitable transparent substrate, preferably quartz, meaning that the layer contains the same materials in the same concentrations as in the OLED. This is done using the same production conditions as in the production of the emission layer for the OLEDs. An absorption spectrum of this film is measured in the wavelength range of 350-500 nm. For this purpose, the reflection spectrum R(λ) and the transmission spectrum T(λ) of the sample are determined at an angle of incidence of 6° (i.e. incidence virtually at right angles). The absorption spectrum in the context of this application is defined as A(λ)=1−R(λ)−T(λ).

If A(λ)≤0.3 in the range of 350-500 nm, the wavelength corresponding to the maximum of the absorption spectrum in the range of 350-500 nm is defined as $\lambda_{exc}$. If, for any wavelength, A(λ)>0.3, $\lambda_{exc}$ is defined as being the greatest wavelength at which A(λ) changes from a value of less than 0.3 to a value of greater than 0.3 or from a value of greater than 0.3 to a value of less than 0.3.

The PLQE is determined using a Hamamatsu C9920-02 measurement system. The principle is based on the excitation of the sample with light of a defined wavelength and the measurement of the radiation absorbed and emitted. During the measurement, the sample is within an Ulbricht sphere ("integrating sphere"). The spectrum of the excitation light is approximately Gaussian with a half-height width of <10 nm and a peak wavelength $\lambda_{exc}$ as defined above.

The PLQE is determined by the evaluation method customary for said measurement system. It should be strictly ensured that the sample does not come into contact with oxygen at any time, since the PLQE of materials having a small energy gap between $S_1$ and $T_1$ is very greatly reduced by oxygen (H. Uoyama et al., Nature 2012, Vol. 492, 234).

B-3) Determination of Decay Time

The decay time is determined using a sample which is produced as described above under "Determination of the PL quantum efficiency (PLQE)". The sample is excited at a temperature of 295 K by a laser pulse (wavelength 266 nm, pulse duration 1.5 ns, pulse energy 200 μJ, beam diameter 4 mm). At this time, the sample is under reduced pressure (<10$^{-5}$ mbar). After excitation (defined as t=0), the profile of the intensity of the photoluminescence emitted against time is measured. The photoluminescence exhibits a steep drop at the start, which is attributable to the prompt fluorescence of the TADF compound. Later on, a slower drop is observed, delayed fluorescence (see, for example, H. Uoyama et al., Nature, vol. 492, no. 7428, pp. 234-238, 2012 and K. Masui et al., Organic Electronics, vol. 14, no. 11, pp. 2721-2726, 2013). The decay time $t_a$ in the context of this application is the decay time of the delayed fluorescence and is determined as follows: A time $t_d$ at which the prompt fluorescence has abated to well below the intensity of the delayed fluorescence (<1%) is chosen, such that the determination of the decay time that follows is not affected thereby. This choice can be made by a person skilled in the art. For the measurement data from the time $t_d$, the decay time $t_a=t_e-t_d$ is determined. In this formula, $t_e$ is that time after t=$t_d$ at which the intensity has for the first time dropped to 1/e of its value at t=$t_d$.

The invention claimed is:

1. An organic electroluminescent device comprising
an anode,
a cathode,
an emitting layer comprising an emitting compound having a magnitude of the difference between the energies of its $S_1$ and $T_1$ states of not more than 0.15 eV, and
a layer which is disposed between the anode and the emitting layer and comprises an amine compound and has been applied from solution, and wherein the amine compound is selected from a polymer containing triarylamine groups comprises at least one structural unit corresponding to the following formula (I):

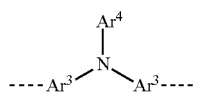

Formula (I)

where:
Ar3, Ar4 is the same or different at each instance and is an aromatic ring system which has 6 to 40 aromatic ring atoms and may be substituted by one or more R3 radicals, or a heteroaromatic ring system which has 5 to 40 aromatic ring atoms and may be substituted by one or more R3 radicals;
R3 is the same or different at each instance and is selected from H, D, F, Cl, Br, I, B(OR4)2, C(=O)R4, CN, Si(R4)3, N(R4)2, P(=O)(R4)2, OR4, S(=O)R4, S(=O)2R4, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R3 radicals may be joined to one another and may form a ring; where the alkyl, alkoxy, alkenyl and alkynyl groups mentioned and the aromatic ring systems and heteroaromatic ring systems mentioned may each be substituted by one or more R4 radicals; and where one or more CH2 groups in the alkyl, alkoxy, alkenyl and alkynyl groups mentioned may be replaced by —R4C=CR4-, —C≡C—, Si(R4)2, C=O, C=NR4, —C(=O)O—, —C(=O)NR4-, NR4, P(=O)(R4), —O—, —S—, SO or SO2;
R4 is the same or different at each instance and is selected from H, D, F, Cl, Br, I, CN, alkyl groups having 1 to 20 carbon atoms, aromatic ring systems having 6 to 40 aromatic ring atoms and heteroaromatic ring systems having 5 to 40 aromatic ring atoms; where two or more R4 radicals may be joined to one another and may form a ring; and where the alkyl groups, aromatic ring systems and heteroaromatic ring systems mentioned may be substituted by F or CN; and
the broken lines represent bonds to adjacent structural units in the polymer;
where the energies of the $S_1$ and $T_1$ states of the emitting compound are determined via quantum-chemical calculations.

2. The organic electroluminescent device according to claim 1, wherein the emitting compound is a luminescent compound, and in that it has a luminescence quantum efficiency, measured as specified in the working examples, of at least 50%.

3. The organic electroluminescent device according to claim 1, wherein the emitting compound has a magnitude of the difference between the energies of its $S_1$ and $T_1$ states of not more than 0.05 eV.

4. The organic electroluminescent device according to claim 1, wherein the emitting compound has both at least one donor substituent and at least one acceptor substituent, with only minor spatial overlap between the Lowest Unoccupied Molecular Orbital (LUMO) and Highest Occupied Molecular Orbital (HOMO) of the compound.

5. The organic electroluminescent device according to claim 4, wherein the at least one donor substituent is chosen from diaryl- or diheteroarylamino groups and carbazole groups or carbazole derivatives, each preferably bonded to an aromatic compound via N, where the groups may also have further substitution, and/or in that the at least one acceptor substituent is chosen from cyano groups and electron-deficient heteroaryl groups which may also have further substitution.

6. The organic electroluminescent device according to claim 1, wherein the layer which is disposed between the anode and emitting layer and has been applied from solution and comprises the amine compound has a thickness of more than 30 nm.

7. The organic electroluminescent device according to claim 1, wherein at least one of the structural units of the formula (I) has at least one crosslinkable group.

8. The organic electroluminescent device according to claim 1, wherein the crosslinkable group is chosen from terminal or cyclic alkenyl groups, terminal dienyl groups, terminal alkynyl groups, alkenyloxy groups, dienyloxy groups, alkynyloxy groups, acrylic acid groups, oxetanes, oxiranes, silanes and cyclobutane groups.

9. The organic electroluminescent device according to claim 1, wherein the layer comprising the amine compound is applied from solution by a method chosen from spin-coating and printing methods, for example screen printing, flexographic printing, nozzle printing, offset printing, LITI (light-induced thermal imaging, thermal transfer printing) or inkjet printing.

10. The organic electroluminescent device according to claim 1, wherein the layer which has been applied from solution and comprises the amine compound has been applied directly to the anode.

11. The organic electroluminescent device according to claim 1, wherein all the layers between the anode and emitting layer have been applied from solution, and in that the emitting layer and all the layers between the emitting layer and the cathode have been applied from the gas phase.

12. A method comprising utilizing the organic electroluminescent device according to claim 1 in displays, as a light source in lighting applications or as a light source in medical or cosmetic applications.

13. A process for producing an organic electroluminescent device comprising
an anode,
a cathode,
an emitting layer comprising an emitting compound having a difference between the energies of its $S_1$ and $T_1$ states of not more than 0.15 eV, and
a layer which is disposed between the anode and the emitting layer and comprises an amine compound, and wherein the amine compound is selected from a polymer containing triarylamine groups comprises at least one structural unit corresponding to the following formula (I):

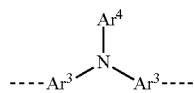

Formula (I)

where:
Ar3, Ar4 is the same or different at each instance and is an aromatic ring system which has 6 to 40 aromatic ring atoms and may be substituted by one or more R3 radicals, or a heteroaromatic ring system which has 5 to 40 aromatic ring atoms and may be substituted by one or more R3 radicals;
R3 is the same or different at each instance and is selected from H, D, F, Cl, Br, I, B(OR4)2, C(=O)R4, CN, Si(R4)3, N(R4)2, P(=O)(R4)2, OR4, S(=O)R4, S(=O)2R4, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R3 radicals may be joined to one another and may form a ring; where the alkyl, alkoxy, alkenyl and alkynyl groups mentioned and the aromatic ring systems and heteroaromatic ring systems mentioned may each be substituted by one or more R4 radicals; and where one or more CH2 groups in the alkyl, alkoxy, alkenyl and alkynyl groups mentioned may be replaced by —R4C=CR4-, —C≡C—, Si(R4)2, C=O, C=NR4, —C(=O)O—, —C(=O)NR4-, NR4, P(=O)(R4), —O—, —S—, SO or SO2;
R4 is the same or different at each instance and is selected from H, D, F, Cl, Br, I, CN, alkyl groups having 1 to 20 carbon atoms, aromatic ring systems having 6 to 40 aromatic ring atoms and heteroaromatic ring systems having 5 to 40 aromatic ring atoms; where two or more R4 radicals may be joined to one another and may form a ring; and where the alkyl groups, aromatic ring systems and heteroaromatic ring systems mentioned may be substituted by F or CN; and
the broken lines represent bonds to adjacent structural units in the polymer;
where the energies of the $S_1$ and $T_1$ states of the emitting compound are determined via quantum-chemical calculations and
where the layer which is disposed between the anode and emitting layer and comprises an amine compound has been applied from solution.

* * * * *